US012599475B2

(12) United States Patent
Hildebrand et al.

(10) Patent No.: US 12,599,475 B2
(45) Date of Patent: Apr. 14, 2026

(54) ACCOMMODATING INTRAOCULAR LENSES AND METHODS OF MANUFACTURING

(71) Applicant: Alcon Inc., Fribourg (CH)

(72) Inventors: Daniel Hildebrand, Santa Cruz, CA (US); Terah Whiting Smiley, Davis, CA (US); Nathan Lewis, San Jose, CA (US); Robert Demitri Angelopoulos, San Jose, CA (US)

(73) Assignee: Alcon Inc., Fribourg (CH)

( * ) Notice: Subject to any disclaimer, the term of this patent is extended or adjusted under 35 U.S.C. 154(b) by 6 days.

(21) Appl. No.: 17/813,851

(22) Filed: Jul. 20, 2022

(65) Prior Publication Data

US 2022/0346942 A1      Nov. 3, 2022

Related U.S. Application Data

(63) Continuation of application No. 15/760,640, filed as application No. PCT/US2016/060799 on Nov. 7, 2016, now Pat. No. 11,426,270.

(Continued)

(51) Int. Cl.
*A61F 2/16* (2006.01)
*G02B 3/12* (2006.01)
*G02B 3/04* (2006.01)

(52) U.S. Cl.
CPC .......... *A61F 2/1601* (2015.04); *A61F 2/1635* (2013.01); *A61F 2/164* (2015.04);
(Continued)

(58) Field of Classification Search
CPC ...... A61F 2/1601; A61F 2/164; A61F 2/1635; A61F 2002/16901; A61F 2240/001;
(Continued)

(56) References Cited

U.S. PATENT DOCUMENTS

| 3,915,172 | A | 10/1975 | Wichterle et al. |
| 4,111,995 | A | 9/1978 | Nelson |

(Continued)

FOREIGN PATENT DOCUMENTS

| AU | 2014202532 | 7/2014 |
| CN | 1283974 | 2/2001 |

(Continued)

OTHER PUBLICATIONS

Baughman et al. "Negative poisson's ratios for extreme states fo matter," *Science*, vol. 288, pp. 2018-2022, Jun. 16, 2000.

(Continued)

*Primary Examiner* — Leslie A Lopez
(74) *Attorney, Agent, or Firm* — Levine Bagade Han LLP

(57) ABSTRACT

An intraocular lens is disclosed that includes an optic body with a projection extending radially outwards from a peripheral surface of the optic body. The projection comprises a haptic contact surface facing radially outward, wherein the entire haptic contact surface is a flat surface. A haptic having a free distal end and a proximal portion is secured to the projection along the haptic contact surface, wherein the projection and the proximal portion interface at a butt joint without the haptic extending into the projection and without the projection extending into the haptic. The haptic also includes a haptic fluid chamber.

6 Claims, 33 Drawing Sheets

Section A-A

Related U.S. Application Data

(60) Provisional application No. 62/377,402, filed on Aug. 19, 2016, provisional application No. 62/357,785, filed on Jul. 1, 2016, provisional application No. 62/321,678, filed on Apr. 12, 2016, provisional application No. 62/321,684, filed on Apr. 12, 2016, provisional application No. 62/321,704, filed on Apr. 12, 2016, provisional application No. 62/321,665, filed on Apr. 12, 2016, provisional application No. 62/321,666, filed on Apr. 12, 2016, provisional application No. 62/321,670, filed on Apr. 12, 2016, provisional application No. 62/321,705, filed on Apr. 12, 2016, provisional application No. 62/252,260, filed on Nov. 6, 2015.

(52) U.S. Cl.
CPC ............... *G02B 3/12* (2013.01); *A61F 2/167* (2013.01); *A61F 2002/1681* (2013.01); *A61F 2002/1682* (2015.04); *A61F 2002/16901* (2015.04); *A61F 2240/001* (2013.01); *G02B 3/04* (2013.01)

(58) Field of Classification Search
CPC .......... A61F 2/167; A61F 2/16–2/1659; A61F 2002/1681–2002/169053; A61F 2230/0017–2230/0021; A61F 2230/0023; A61F 2250/0003
See application file for complete search history.

(56) References Cited

U.S. PATENT DOCUMENTS

| | | | |
|---|---|---|---|
| 4,134,161 A * | 1/1979 | Bayers | A61F 2/16 623/6.43 |
| 4,251,887 A | 2/1981 | Anis | |
| 4,253,199 A | 3/1981 | Banko | |
| 4,254,509 A | 3/1981 | Tennant | |
| 4,304,895 A | 12/1981 | Loshaek | |
| 4,373,218 A | 2/1983 | Schachar | |
| 4,409,691 A | 10/1983 | Levy | |
| 4,423,809 A | 1/1984 | Mazzocco | |
| 4,435,855 A | 3/1984 | Pannu | |
| 4,435,856 A | 3/1984 | L'Esperance | |
| 4,466,705 A | 8/1984 | Michelson | |
| 4,490,860 A | 1/1985 | Rainin | |
| 4,494,254 A | 1/1985 | Lopez | |
| 4,512,040 A | 4/1985 | Mcclure | |
| 4,528,311 A | 7/1985 | Beard et al. | |
| 4,575,373 A | 3/1986 | Johnson | |
| 4,585,457 A | 4/1986 | Kalb | |
| 4,604,295 A | 8/1986 | Humphreys | |
| 4,615,701 A | 10/1986 | Woods | |
| 4,617,715 A | 10/1986 | Koistinen et al. | |
| 4,620,954 A | 11/1986 | Singer et al. | |
| 4,634,418 A | 1/1987 | Binder | |
| 4,685,921 A | 8/1987 | Peyman | |
| 4,685,922 A | 8/1987 | Peyman | |
| 4,693,717 A | 9/1987 | Michelson | |
| 4,720,286 A | 1/1988 | Bailey et al. | |
| 4,731,078 A | 3/1988 | Stoy et al. | |
| 4,731,079 A | 3/1988 | Stoy | |
| 4,731,080 A | 3/1988 | Galin | |
| 4,764,423 A | 8/1988 | Yamaguchi et al. | |
| 4,784,485 A | 11/1988 | Ho | |
| 4,787,903 A | 11/1988 | Grendahl | |
| 4,790,847 A | 12/1988 | Woods | |
| 4,813,956 A | 3/1989 | Gupta | |
| 4,816,031 A | 3/1989 | Pfoff | |
| 4,836,201 A | 6/1989 | Patton et al. | |
| 4,842,601 A | 6/1989 | Smith | |
| 4,848,343 A | 7/1989 | Wallsten et al. | |
| 4,863,457 A | 9/1989 | Lee | |
| 4,888,012 A | 12/1989 | Horn et al. | |
| 4,892,543 A | 1/1990 | Turley | |
| 4,902,293 A | 2/1990 | Feaster | |
| 4,913,536 A | 4/1990 | Barnea | |
| 4,919,151 A | 4/1990 | Grubbs et al. | |
| 4,932,966 A | 6/1990 | Christie et al. | |
| 4,946,469 A | 8/1990 | Sarfarazi | |
| 4,950,289 A | 8/1990 | Krasner | |
| 4,963,148 A | 10/1990 | Sulc et al. | |
| 4,994,082 A | 2/1991 | Richards et al. | |
| 4,995,879 A | 2/1991 | Dougherty | |
| 4,995,880 A | 2/1991 | Galib | |
| 5,015,254 A | 5/1991 | Greite | |
| 5,035,710 A | 7/1991 | Nakada et al. | |
| 5,047,051 A | 9/1991 | Cumming | |
| 5,061,914 A | 10/1991 | Busch et al. | |
| 5,066,301 A | 11/1991 | Wiley | |
| 5,078,740 A | 1/1992 | Walman | |
| 5,145,884 A | 9/1992 | Yamamoto et al. | |
| 5,145,935 A | 9/1992 | Hayashi | |
| 5,152,789 A | 10/1992 | Willis | |
| 5,169,920 A | 12/1992 | Okawa | |
| 5,171,266 A | 12/1992 | Wiley et al. | |
| 5,180,390 A * | 1/1993 | Drews | A61F 2/1616 623/6.4 |
| 5,190,552 A | 3/1993 | Kelman | |
| 5,200,430 A | 4/1993 | Federman | |
| 5,201,763 A | 4/1993 | Brady et al. | |
| 5,203,788 A | 4/1993 | Wiley | |
| 5,213,579 A | 5/1993 | Yamada et al. | |
| 5,224,957 A | 7/1993 | Gasser et al. | |
| 5,235,003 A | 8/1993 | Ward et al. | |
| 5,246,452 A | 9/1993 | Sinnott | |
| 5,251,993 A | 10/1993 | Sigourney | |
| 5,275,623 A | 1/1994 | Sarfarazi | |
| 5,275,624 A | 1/1994 | Hara et al. | |
| 5,288,293 A | 2/1994 | O'donnell | |
| 5,290,892 A | 3/1994 | Namdaran et al. | |
| 5,326,347 A | 7/1994 | Cumming | |
| 5,391,590 A | 2/1995 | Gerace et al. | |
| 5,405,386 A | 4/1995 | Rheinish et al. | |
| 5,426,166 A | 6/1995 | Usifer et al. | |
| 5,443,506 A | 8/1995 | Garabet | |
| 5,444,106 A | 8/1995 | Zhou et al. | |
| 5,444,135 A | 8/1995 | Cheradame et al. | |
| 5,476,514 A | 12/1995 | Cumming | |
| 5,489,302 A | 2/1996 | Skottun | |
| 5,496,366 A | 3/1996 | Cumming | |
| 5,506,300 A | 4/1996 | Ward et al. | |
| 5,512,609 A | 4/1996 | Yang | |
| 5,567,365 A | 10/1996 | Weinschenk et al. | |
| 5,571,189 A | 11/1996 | Kuslich | |
| 5,578,081 A | 11/1996 | Mcdonald | |
| 5,585,049 A | 12/1996 | Grisoni et al. | |
| 5,593,436 A | 1/1997 | Langerman | |
| 5,607,472 A | 3/1997 | Thompson | |
| 5,628,795 A | 5/1997 | Langerman | |
| 5,633,504 A | 5/1997 | Collins et al. | |
| 5,665,822 A | 9/1997 | Bitler et al. | |
| 5,674,282 A | 10/1997 | Cumming | |
| 5,676,669 A | 10/1997 | Colvard | |
| 5,676,944 A | 10/1997 | Alvarado et al. | |
| 5,693,095 A | 12/1997 | Freeman et al. | |
| 5,697,973 A | 12/1997 | Peyman et al. | |
| 5,702,441 A | 12/1997 | Zhou | |
| 5,767,669 A | 6/1998 | Hansen et al. | |
| 5,774,273 A | 6/1998 | Bornhorst | |
| 5,776,191 A | 7/1998 | Mazzocco | |
| 5,776,192 A | 7/1998 | Mcdonald | |
| 5,792,099 A | 8/1998 | Decamp et al. | |
| 5,800,533 A | 9/1998 | Eggleston et al. | |
| 5,843,188 A | 12/1998 | Mcdonald | |
| 5,891,931 A | 4/1999 | Leboeuf et al. | |
| 5,928,282 A | 7/1999 | Nigam | |
| 5,964,802 A | 10/1999 | Anello et al. | |
| 5,968,095 A | 10/1999 | Norrby | |
| 5,984,962 A | 11/1999 | Anello et al. | |
| 6,013,101 A | 1/2000 | Israel | |
| 6,015,842 A | 1/2000 | Leboeuf et al. | |

(56)     References Cited

U.S. PATENT DOCUMENTS

| | | |
|---|---|---|
| 6,102,539 A | 8/2000 | Tucker |
| 6,117,171 A | 9/2000 | Skottun |
| 6,124,980 A | 9/2000 | Cerbell |
| 6,139,576 A | 10/2000 | Doyle et al. |
| 6,152,918 A | 11/2000 | Padilla et al. |
| 6,160,084 A | 12/2000 | Langer et al. |
| 6,176,878 B1 | 1/2001 | Gwon et al. |
| 6,180,687 B1 | 1/2001 | Hammer et al. |
| 6,188,526 B1 | 2/2001 | Sasaya et al. |
| 6,190,410 B1 | 2/2001 | Lamielle et al. |
| 6,195,807 B1 | 3/2001 | Chou |
| 6,197,059 B1 | 3/2001 | Cumming |
| 6,214,961 B1 | 4/2001 | Aoki |
| 6,217,612 B1 | 4/2001 | Woods |
| 6,225,367 B1 | 5/2001 | Chaouk et al. |
| 6,229,641 B1 | 5/2001 | Kosaka |
| 6,299,641 B1 | 10/2001 | Woods |
| 6,302,911 B1 | 10/2001 | Hanna |
| 6,302,912 B1 | 10/2001 | Bernau |
| 6,322,589 B1 | 11/2001 | Cumming |
| 6,342,073 B1 | 1/2002 | Cumming et al. |
| 6,348,437 B1 | 2/2002 | Avery et al. |
| 6,387,126 B1 | 5/2002 | Cumming |
| 6,388,043 B1 | 5/2002 | Langer et al. |
| 6,406,494 B1 | 6/2002 | Laguette et al. |
| 6,413,262 B2 | 7/2002 | Saishin et al. |
| 6,423,094 B1 | 7/2002 | Sarfarazi |
| 6,436,092 B1 | 8/2002 | Peyman |
| 6,443,985 B1 | 9/2002 | Woods |
| 6,450,642 B1 | 9/2002 | Jethmalani et al. |
| 6,464,725 B2 | 10/2002 | Skotton |
| 6,488,708 B2 | 12/2002 | Sarfarazi |
| 6,493,151 B2 | 12/2002 | Schachar |
| 6,503,276 B2 | 1/2003 | Lang et al. |
| 6,517,577 B1 | 2/2003 | Callahan et al. |
| 6,528,602 B1 | 3/2003 | Freeman et al. |
| 6,551,354 B1 | 4/2003 | Ghazizadeh et al. |
| 6,552,860 B1 | 4/2003 | Alden |
| 6,554,859 B1 | 4/2003 | Lang et al. |
| 6,585,768 B2 | 7/2003 | Hamano et al. |
| 6,589,550 B1 | 7/2003 | Hodd et al. |
| 6,592,621 B1 | 7/2003 | Domino |
| 6,599,317 B1 | 7/2003 | Weinschenk et al. |
| 6,601,956 B1 | 8/2003 | Jean et al. |
| 6,610,350 B2 | 8/2003 | Suzuki et al. |
| 6,616,691 B1 | 9/2003 | Tran |
| 6,616,692 B1 | 9/2003 | Glick et al. |
| 6,638,304 B2 | 10/2003 | Azar |
| 6,638,305 B2 | 10/2003 | Laguette |
| 6,638,306 B2 | 10/2003 | Cumming |
| 6,645,245 B1 | 11/2003 | Preussner |
| 6,645,246 B1 | 11/2003 | Weinschenk et al. |
| 6,656,223 B2 | 12/2003 | Brady |
| 6,660,035 B1 | 12/2003 | Lang et al. |
| 6,692,525 B2 | 2/2004 | Brady et al. |
| 6,695,881 B2 | 2/2004 | Peng et al. |
| 6,709,108 B2 | 3/2004 | Levine et al. |
| 6,712,848 B1 | 3/2004 | Wolf et al. |
| 6,730,123 B2 | 5/2004 | Klopotek |
| 6,743,388 B2 | 6/2004 | Sridharan et al. |
| 6,749,632 B2 | 6/2004 | Sandstedt et al. |
| 6,749,634 B2 | 6/2004 | Hanna |
| 6,786,934 B2 | 9/2004 | Zadno-Azizi et al. |
| 6,818,158 B2 | 11/2004 | Pham et al. |
| 6,827,738 B2 | 12/2004 | Willis et al. |
| 6,836,374 B2 | 12/2004 | Esch et al. |
| 6,860,601 B2 | 3/2005 | Shadduck |
| 6,878,320 B2 | 4/2005 | Alderson et al. |
| 6,884,261 B2 | 4/2005 | Zadno-Azizi et al. |
| 6,899,732 B2 | 5/2005 | Zadno-Azizi et al. |
| 6,899,850 B2 | 5/2005 | Haywood et al. |
| 6,914,247 B2 | 7/2005 | Duggan et al. |
| 6,926,736 B2 | 8/2005 | Peng et al. |
| 6,935,743 B2 | 8/2005 | Shadduck |
| 6,949,093 B1 | 9/2005 | Peyman |
| 6,966,649 B2 | 11/2005 | Shadduck |
| 6,969,403 B2 | 11/2005 | Peng et al. |
| 7,001,374 B2 | 2/2006 | Peyman |
| 7,060,094 B2 | 6/2006 | Shahinpoor et al. |
| 7,068,439 B2 | 6/2006 | Esch et al. |
| 7,070,276 B2 | 7/2006 | Koretz |
| 7,074,227 B2 | 7/2006 | Portney |
| 7,122,053 B2 | 10/2006 | Esch |
| 7,144,423 B2 | 12/2006 | Mcdonald |
| 7,217,288 B2 | 5/2007 | Esch et al. |
| 7,241,312 B2 | 7/2007 | Lai et al. |
| 7,247,168 B2 * | 7/2007 | Esch ..................... A61F 2/1635 |
| | | 623/6.37 |
| 7,247,689 B2 | 7/2007 | Makker et al. |
| 7,261,737 B2 | 8/2007 | Esch et al. |
| 7,264,351 B2 | 9/2007 | Shadduck |
| 7,276,619 B2 | 10/2007 | Kunzler et al. |
| 7,278,739 B2 | 10/2007 | Shadduck |
| 7,311,194 B2 | 12/2007 | Jin et al. |
| 7,354,451 B2 | 4/2008 | Koch |
| 7,378,382 B2 | 5/2008 | Serobian et al. |
| 7,416,300 B2 | 8/2008 | Wei et al. |
| 7,438,723 B2 | 10/2008 | Esch |
| 7,453,646 B2 | 11/2008 | Lo |
| 7,485,144 B2 | 2/2009 | Esch |
| 7,494,505 B2 | 2/2009 | Kappelhof et al. |
| 7,637,947 B2 | 12/2009 | Smith et al. |
| 7,675,686 B2 | 3/2010 | Lo et al. |
| 7,753,953 B1 | 7/2010 | Yee |
| 7,759,408 B2 | 7/2010 | Schorzman et al. |
| 7,763,069 B2 | 7/2010 | Brady et al. |
| 7,776,088 B2 | 8/2010 | Shadduck |
| 7,867,205 B2 | 1/2011 | Bergheim et al. |
| 7,878,655 B2 | 2/2011 | Salvati et al. |
| 7,971,997 B2 | 7/2011 | Hiramatsu et al. |
| 7,988,290 B2 | 8/2011 | Campbell et al. |
| 7,988,292 B2 | 8/2011 | Neal et al. |
| 7,988,293 B2 | 8/2011 | Raymond et al. |
| 8,048,155 B2 | 11/2011 | Shadduck |
| 8,158,712 B2 | 4/2012 | Your |
| 8,162,927 B2 | 4/2012 | Peyman |
| 8,241,355 B2 | 8/2012 | Brady et al. |
| 8,303,656 B2 | 11/2012 | Shadduck |
| 8,314,927 B2 | 11/2012 | Choi et al. |
| 8,328,869 B2 | 12/2012 | Smiley et al. |
| 8,361,145 B2 | 1/2013 | Scholl et al. |
| 8,377,125 B2 | 2/2013 | Kellan |
| 8,425,599 B2 | 4/2013 | Shadduck |
| 8,447,086 B2 | 5/2013 | Hildebrand et al. |
| 8,454,688 B2 | 6/2013 | Esch et al. |
| 8,480,734 B2 | 7/2013 | Kellan et al. |
| 8,523,941 B2 | 9/2013 | Ichinohe et al. |
| 8,574,239 B2 | 11/2013 | Ichinohe et al. |
| 8,613,766 B2 | 12/2013 | Richardson et al. |
| 8,632,589 B2 | 1/2014 | Helmy |
| 8,641,748 B2 | 2/2014 | Hebert et al. |
| 8,668,734 B2 | 3/2014 | Hildebrand et al. |
| 8,721,656 B2 | 5/2014 | De Juan et al. |
| 8,900,298 B2 | 12/2014 | Anvar et al. |
| 8,956,408 B2 | 2/2015 | Smiley et al. |
| 8,968,396 B2 | 3/2015 | Matthews et al. |
| 8,992,609 B2 | 3/2015 | Shadduck |
| 9,005,282 B2 | 4/2015 | Chang et al. |
| 9,034,035 B2 | 5/2015 | Betser et al. |
| 9,044,317 B2 | 6/2015 | Hildebrand et al. |
| 9,066,783 B2 | 6/2015 | Euteneuer et al. |
| 9,226,852 B2 | 1/2016 | Schieber et al. |
| 9,277,987 B2 | 3/2016 | Smiley et al. |
| 9,326,846 B2 | 5/2016 | Devita Gerardi et al. |
| 9,329,306 B2 | 5/2016 | Huang et al. |
| 9,456,895 B2 | 10/2016 | Shadduck |
| 9,610,155 B2 | 4/2017 | Matthews |
| 9,622,855 B2 | 4/2017 | Portney et al. |
| 9,693,858 B2 | 7/2017 | Hildebrand et al. |
| 9,795,473 B2 | 10/2017 | Smiley et al. |
| 9,848,979 B2 | 12/2017 | Vilupuru et al. |
| 9,855,137 B2 | 1/2018 | Smiley et al. |
| 9,855,139 B2 | 1/2018 | Matthews et al. |
| 9,872,762 B2 | 1/2018 | Scholl et al. |

(56)  References Cited

U.S. PATENT DOCUMENTS

| | | | |
|---|---|---|---|
| 9,872,763 B2 | 1/2018 | Smiley et al. | |
| 10,406,025 B2 | 9/2019 | Wardle et al. | |
| 11,426,270 B2 | 8/2022 | Hildebrand et al. | |
| 11,737,862 B2 | 8/2023 | Anvar et al. | |
| 11,931,248 B2 * | 3/2024 | Collins | A61F 2/1694 |
| 11,980,542 B2 | 5/2024 | Peyman et al. | |
| 12,059,342 B2 | 8/2024 | Hajela et al. | |
| 2001/0001836 A1 | 5/2001 | Cumming | |
| 2001/0010019 A1 | 7/2001 | Schachar | |
| 2001/0016771 A1 | 8/2001 | Cumming | |
| 2001/0039449 A1 | 11/2001 | Johnson et al. | |
| 2001/0051826 A1 | 12/2001 | Bogaert et al. | |
| 2002/0010278 A1 | 1/2002 | Garcia-Franco et al. | |
| 2002/0013572 A1 | 1/2002 | Berlin | |
| 2002/0046783 A1 | 4/2002 | Johnson et al. | |
| 2002/0055777 A1 | 5/2002 | Cumming et al. | |
| 2002/0072795 A1 | 6/2002 | Green | |
| 2002/0095212 A1 | 7/2002 | Boehm | |
| 2002/0107568 A1 | 8/2002 | Zadno-Azizi et al. | |
| 2002/0111678 A1 | 8/2002 | Zadno-Azizi et al. | |
| 2002/0116057 A1 | 8/2002 | Ting et al. | |
| 2002/0116058 A1 | 8/2002 | Zadno-Azizi et al. | |
| 2002/0116059 A1 | 8/2002 | Zadno-Azizi et al. | |
| 2002/0116060 A1 | 8/2002 | Nguyen et al. | |
| 2002/0116061 A1 | 8/2002 | Zadno-Azizi et al. | |
| 2002/0116062 A1 * | 8/2002 | Portney | A61F 2/1602 |
| | | | 623/6.46 |
| 2002/0133228 A1 | 9/2002 | Sarver | |
| 2002/0161434 A1 | 10/2002 | Laguette et al. | |
| 2002/0161435 A1 | 10/2002 | Portney | |
| 2002/0177896 A1 | 11/2002 | Israel | |
| 2002/0193725 A1 | 12/2002 | Odrich | |
| 2002/0193876 A1 | 12/2002 | Lang et al. | |
| 2003/0003295 A1 | 1/2003 | Dreher et al. | |
| 2003/0004569 A1 | 1/2003 | Haefliger | |
| 2003/0018384 A1 | 1/2003 | Valyunin et al. | |
| 2003/0042176 A1 | 3/2003 | Alderson et al. | |
| 2003/0050695 A1 | 3/2003 | Lin et al. | |
| 2003/0050696 A1 | 3/2003 | Cumming | |
| 2003/0060878 A1 | 3/2003 | Shadduck | |
| 2003/0060881 A1 | 3/2003 | Glick et al. | |
| 2003/0078656 A1 | 4/2003 | Nguyen | |
| 2003/0078657 A1 | 4/2003 | Zadno-Azizi et al. | |
| 2003/0078658 A1 | 4/2003 | Zadno-Azizi | |
| 2003/0083744 A1 | 5/2003 | Khoury | |
| 2003/0109925 A1 | 6/2003 | Ghazizadeh et al. | |
| 2003/0109926 A1 | 6/2003 | Portney | |
| 2003/0120200 A1 | 6/2003 | Bergheim | |
| 2003/0130732 A1 | 7/2003 | Sarfarazi | |
| 2003/0135272 A1 | 7/2003 | Brady et al. | |
| 2003/0135273 A1 | 7/2003 | Callahan et al. | |
| 2003/0158599 A1 | 8/2003 | Brady et al. | |
| 2003/0171808 A1 | 9/2003 | Phillips | |
| 2003/0171809 A1 * | 9/2003 | Phillips | A61F 2/1629 |
| | | | 623/6.46 |
| 2003/0183960 A1 | 10/2003 | Buazza et al. | |
| 2003/0187505 A1 | 10/2003 | Liao | |
| 2003/0199977 A1 | 10/2003 | Cumming | |
| 2003/0236376 A1 | 12/2003 | Kindt-larsen et al. | |
| 2004/0001180 A1 | 1/2004 | Epstein | |
| 2004/0006386 A1 | 1/2004 | Valint et al. | |
| 2004/0006387 A1 | 1/2004 | Kelman | |
| 2004/0008419 A1 | 1/2004 | Schachar | |
| 2004/0015236 A1 | 1/2004 | Sarfarazi | |
| 2004/0039446 A1 | 2/2004 | Mcnicholas | |
| 2004/0054408 A1 | 3/2004 | Glick et al. | |
| 2004/0059343 A1 | 3/2004 | Shearer et al. | |
| 2004/0066489 A1 | 4/2004 | Benedikt et al. | |
| 2004/0082993 A1 | 4/2004 | Woods | |
| 2004/0082994 A1 | 4/2004 | Woods et al. | |
| 2004/0085511 A1 | 5/2004 | Uno et al. | |
| 2004/0085515 A1 | 5/2004 | Roffman et al. | |
| 2004/0088050 A1 | 5/2004 | Norrby et al. | |
| 2004/0111151 A1 | 6/2004 | Paul et al. | |
| 2004/0111152 A1 | 6/2004 | Kelman | |
| 2004/0111153 A1 | 6/2004 | Woods et al. | |
| 2004/0127984 A1 | 7/2004 | Paul et al. | |
| 2004/0162612 A1 | 8/2004 | Portney et al. | |
| 2004/0181279 A1 | 9/2004 | Nun | |
| 2004/0230203 A1 | 11/2004 | Yaguchi | |
| 2005/0021139 A1 | 1/2005 | Shadduck | |
| 2005/0090612 A1 | 4/2005 | Soane et al. | |
| 2005/0096741 A1 * | 5/2005 | Cumming | B29D 11/026 |
| | | | 623/6.37 |
| 2005/0113911 A1 | 5/2005 | Peyman | |
| 2005/0125000 A1 | 6/2005 | Tourrette et al. | |
| 2005/0131535 A1 | 6/2005 | Woods | |
| 2005/0154443 A1 | 7/2005 | Linder et al. | |
| 2005/0165410 A1 | 7/2005 | Zadno-Azizi et al. | |
| 2005/0251253 A1 | 11/2005 | Gross | |
| 2005/0264756 A1 | 12/2005 | Esch | |
| 2006/0069433 A1 | 3/2006 | Nun | |
| 2006/0100703 A1 | 5/2006 | Evans et al. | |
| 2006/0116763 A1 | 6/2006 | Simpson | |
| 2006/0134173 A1 | 6/2006 | Liu et al. | |
| 2006/0158611 A1 | 7/2006 | Piers et al. | |
| 2006/0183041 A1 | 8/2006 | Erk et al. | |
| 2006/0184181 A1 | 8/2006 | Cole et al. | |
| 2006/0200167 A1 | 9/2006 | Peterson et al. | |
| 2006/0241752 A1 | 10/2006 | Israel | |
| 2006/0253196 A1 | 11/2006 | Woods | |
| 2007/0004886 A1 | 1/2007 | Schorzman et al. | |
| 2007/0005136 A1 | 1/2007 | Richardson | |
| 2007/0021831 A1 | 1/2007 | Clarke | |
| 2007/0027538 A1 | 2/2007 | Aharoni et al. | |
| 2007/0050023 A1 | 3/2007 | Bessiere et al. | |
| 2007/0078515 A1 | 4/2007 | Brady | |
| 2007/0088433 A1 | 4/2007 | Esch et al. | |
| 2007/0100445 A1 | 5/2007 | Shadduck | |
| 2007/0106377 A1 | 5/2007 | Smith et al. | |
| 2007/0118147 A1 | 5/2007 | Smedley et al. | |
| 2007/0118216 A1 | 5/2007 | Pynson | |
| 2007/0129801 A1 | 6/2007 | Cumming | |
| 2007/0156236 A1 | 7/2007 | Stenger | |
| 2007/0162112 A1 | 7/2007 | Burriesci et al. | |
| 2007/0213817 A1 | 9/2007 | Esch et al. | |
| 2007/0244561 A1 | 10/2007 | Ben nun | |
| 2007/0254005 A1 | 11/2007 | Pathak et al. | |
| 2007/0260157 A1 | 11/2007 | Norrby | |
| 2008/0004699 A1 | 1/2008 | Ben nun | |
| 2008/0015689 A1 | 1/2008 | Esch et al. | |
| 2008/0027537 A1 * | 1/2008 | Gerlach | A61L 27/50 |
| | | | 623/6.22 |
| 2008/0033449 A1 | 2/2008 | Cole et al. | |
| 2008/0035243 A1 | 2/2008 | Breitenkamp et al. | |
| 2008/0046074 A1 | 2/2008 | Smith et al. | |
| 2008/0046075 A1 | 2/2008 | Esch et al. | |
| 2008/0097460 A1 | 4/2008 | Boukhny et al. | |
| 2008/0139769 A1 | 6/2008 | Iwamoto et al. | |
| 2008/0179770 A1 | 7/2008 | Rooney et al. | |
| 2008/0188930 A1 | 8/2008 | Mentak et al. | |
| 2008/0243247 A1 | 10/2008 | Poley et al. | |
| 2008/0269887 A1 | 10/2008 | Cumming | |
| 2008/0269891 A1 | 10/2008 | Hong et al. | |
| 2008/0300680 A1 | 12/2008 | Joshua | |
| 2008/0306587 A1 | 12/2008 | Your | |
| 2008/0306588 A1 | 12/2008 | Smiley et al. | |
| 2009/0005865 A1 | 1/2009 | Smiley et al. | |
| 2009/0076602 A1 | 3/2009 | Ho et al. | |
| 2009/0082863 A1 | 3/2009 | Schieber et al. | |
| 2009/0124773 A1 | 5/2009 | Zhou et al. | |
| 2009/0149952 A1 | 6/2009 | Shadduck | |
| 2009/0171327 A1 | 7/2009 | Kurtz et al. | |
| 2009/0228101 A1 | 9/2009 | Zadno-Azizi | |
| 2009/0234449 A1 | 9/2009 | De juan et al. | |
| 2009/0248154 A1 * | 10/2009 | Dell | A61F 2/1629 |
| | | | 623/6.46 |
| 2009/0264998 A1 | 10/2009 | Mentak et al. | |
| 2009/0281620 A1 | 11/2009 | Sacharoff et al. | |
| 2009/0292293 A1 | 11/2009 | Bogaert et al. | |
| 2009/0312836 A1 | 12/2009 | Pinchuk et al. | |
| 2009/0319040 A1 | 12/2009 | Khoury | |
| 2010/0016963 A1 | 1/2010 | Park | |
| 2010/0039709 A1 | 2/2010 | Lo | |

(56) References Cited

U.S. PATENT DOCUMENTS

| | | |
|---|---|---|
| 2010/0063588 A1 | 3/2010 | Park |
| 2010/0069522 A1 | 3/2010 | Linhardt et al. |
| 2010/0094412 A1 | 4/2010 | Wensrich |
| 2010/0131058 A1 | 5/2010 | Shadduck |
| 2010/0131061 A1 | 5/2010 | Callahan et al. |
| 2010/0140114 A1 | 6/2010 | Pruitt et al. |
| 2010/0161049 A1 | 6/2010 | Inoue |
| 2010/0179653 A1 | 7/2010 | Argento et al. |
| 2010/0228344 A1 | 9/2010 | Shadduck |
| 2010/0228346 A1 | 9/2010 | Esch |
| 2011/0118834 A1 | 5/2011 | Lo et al. |
| 2011/0153015 A1 | 6/2011 | Simonov et al. |
| 2011/0313522 A1 | 12/2011 | Hayes |
| 2011/0313523 A1 | 12/2011 | Hayes |
| 2012/0035525 A1 | 2/2012 | Silvestrini |
| 2012/0078363 A1 | 3/2012 | Lu |
| 2012/0078364 A1 | 3/2012 | Stenger |
| 2012/0116506 A1 | 5/2012 | Compertore |
| 2012/0179249 A1 | 7/2012 | Coleman |
| 2012/0221102 A1 | 8/2012 | Tanaka et al. |
| 2012/0226351 A1 | 9/2012 | Peyman |
| 2012/0253458 A1 | 10/2012 | Geraghty et al. |
| 2012/0253459 A1 | 10/2012 | Reich et al. |
| 2012/0296425 A1 | 11/2012 | Cumming |
| 2012/0303119 A1 | 11/2012 | Callahan et al. |
| 2012/0330415 A1 | 12/2012 | Callahan et al. |
| 2013/0053953 A1 | 2/2013 | Silvestrini |
| 2013/0053954 A1 | 2/2013 | Rao et al. |
| 2013/0060331 A1 | 3/2013 | Shadduck |
| 2013/0128368 A1 | 5/2013 | Costache et al. |
| 2013/0131794 A1 | 5/2013 | Smiley et al. |
| 2013/0184816 A1 | 7/2013 | Hayes |
| 2013/0250239 A1 | 9/2013 | Hildebrand et al. |
| 2013/0268070 A1 | 10/2013 | Esch et al. |
| 2013/0317607 A1 | 11/2013 | Deboer et al. |
| 2014/0012279 A1 | 1/2014 | De Juan et al. |
| 2014/0121768 A1 | 5/2014 | Simpson |
| 2014/0142587 A1 | 5/2014 | Walter et al. |
| 2014/0227437 A1 | 8/2014 | Deboer et al. |
| 2014/0228949 A1 | 8/2014 | Argento et al. |
| 2014/0257478 A1 | 9/2014 | Mccafferty |
| 2014/0275362 A1 | 9/2014 | Fenn et al. |
| 2014/0330375 A1 | 11/2014 | Mccafferty |
| 2014/0336757 A1 | 11/2014 | Simonov et al. |
| 2014/0378886 A1 | 12/2014 | De Juan et al. |
| 2014/0379078 A1 | 12/2014 | Trindade |
| 2015/0087743 A1 | 3/2015 | Anvar et al. |
| 2015/0151021 A1 | 6/2015 | Jiang et al. |
| 2015/0202041 A1 | 7/2015 | Shadduck |
| 2015/0238310 A1 | 8/2015 | Matthews et al. |
| 2015/0282982 A1 | 10/2015 | Schieber et al. |
| 2016/0008126 A1 | 1/2016 | Salahieh et al. |
| 2016/0038278 A1 | 2/2016 | Matthews |
| 2016/0058552 A1 | 3/2016 | Argal et al. |
| 2016/0058553 A1* | 3/2016 | Salahieh ............... A61F 2/1629 |
| | | 623/6.13 |
| 2016/0106534 A1 | 4/2016 | Deboer et al. |
| 2016/0113761 A1 | 4/2016 | Nishi et al. |
| 2016/0128826 A1 | 5/2016 | Silvestrini et al. |
| 2016/0128827 A1 | 5/2016 | Zhao |
| 2016/0157996 A1 | 6/2016 | Dolla et al. |
| 2016/0184089 A1 | 6/2016 | Dudee et al. |
| 2016/0184092 A1 | 6/2016 | Smiley et al. |
| 2016/0262875 A1 | 9/2016 | Smith et al. |
| 2016/0324630 A1* | 11/2016 | McCafferty ........... A61F 2/1635 |
| 2017/0020662 A1 | 1/2017 | Shadduck |
| 2017/0049561 A1 | 2/2017 | Smiley et al. |
| 2017/0127941 A1 | 5/2017 | Ostermeier et al. |
| 2017/0239272 A1 | 8/2017 | Ambati et al. |
| 2017/0258581 A1 | 9/2017 | Borja et al. |
| 2017/0290658 A1 | 10/2017 | Hildebrand et al. |
| 2017/0348093 A1 | 12/2017 | Deacon et al. |
| 2018/0028308 A1 | 2/2018 | Smiley et al. |
| 2018/0125640 A1 | 5/2018 | Smiley et al. |
| 2018/0132997 A1 | 5/2018 | Smiley et al. |
| 2018/0147051 A1 | 5/2018 | Scholl et al. |
| 2018/0153682 A1 | 6/2018 | Hajela et al. |
| 2018/0256315 A1 | 9/2018 | Hildebrand et al. |
| 2020/0015955 A1 | 1/2020 | Bos et al. |
| 2021/0030530 A1 | 2/2021 | Smiley et al. |
| 2021/0100650 A1 | 4/2021 | Smiley et al. |
| 2021/0100652 A1 | 4/2021 | Walz et al. |
| 2022/0267571 A1 | 8/2022 | Fihri et al. |
| 2023/0054347 A1 | 2/2023 | Snyder |
| 2023/0240834 A1 | 8/2023 | Micheletti et al. |
| 2023/0314838 A1 | 10/2023 | Portney et al. |
| 2023/0355375 A1 | 11/2023 | Anvar et al. |
| 2024/0035025 A1 | 2/2024 | Angel et al. |
| 2024/0231128 A1 | 7/2024 | Peyman |

FOREIGN PATENT DOCUMENTS

| | | |
|---|---|---|
| CN | 1367667 | 9/2002 |
| CN | 1378440 | 11/2002 |
| CN | 1384727 | 12/2002 |
| CN | 101039635 | 9/2007 |
| CN | 101277659 | 10/2008 |
| CN | 100471898 | 3/2009 |
| CN | 101547958 | 9/2009 |
| CN | 101678149 | 3/2010 |
| CN | 101795642 | 8/2010 |
| CN | 102271622 | 12/2011 |
| CN | 202288610 | 7/2012 |
| CN | 103561786 | 2/2014 |
| CN | 104244867 | 11/2017 |
| DE | 202023107196 | 3/2024 |
| EP | 0898972 | 3/1999 |
| EP | 2060243 | 5/2009 |
| EP | 2192934 | 6/2010 |
| FR | 2655841 | 6/1991 |
| FR | 2784575 | 12/2000 |
| JP | 05-043699 | 2/1993 |
| JP | 07-044938 | 5/1995 |
| JP | 07-196946 | 8/1995 |
| JP | 08-034855 | 2/1996 |
| JP | 08-501715 | 2/1996 |
| JP | 08-224295 | 9/1996 |
| JP | 08-239479 | 9/1996 |
| JP | 09-165449 | 6/1997 |
| JP | 09-294754 | 11/1997 |
| JP | 10-206609 | 8/1998 |
| JP | 11-047168 | 2/1999 |
| JP | 11-056998 | 3/1999 |
| JP | 1999-056998 | 3/1999 |
| JP | 11-169391 | 6/1999 |
| JP | 11-276509 | 10/1999 |
| JP | 11-332903 | 12/1999 |
| JP | 2001-502592 | 2/2001 |
| JP | 2003-144387 | 5/2003 |
| JP | 2003-144538 | 5/2003 |
| JP | 2003-524503 | 8/2003 |
| JP | 2003-530978 | 10/2003 |
| JP | 2005-517802 | 6/2005 |
| JP | 2006-341094 | 12/2006 |
| JP | 2007-513715 | 5/2007 |
| JP | 2007-518447 | 7/2007 |
| JP | 2008-531069 | 8/2008 |
| JP | 2008-307394 | 12/2008 |
| JP | 2008-544817 | 12/2008 |
| JP | 2009-034451 | 2/2009 |
| JP | 2010-514507 | 5/2010 |
| JP | 2010-518948 | 6/2010 |
| JP | 2010-534519 | 11/2010 |
| JP | 2010-534520 | 11/2010 |
| JP | 2012-515019 | 7/2012 |
| JP | 2013-520291 | 6/2013 |
| JP | 2014-533175 | 12/2014 |
| JP | 2015-003049 | 1/2015 |
| SU | 1810052 | 4/1993 |
| WO | WO 1995/002378 | 1/1995 |
| WO | WO 1997/006751 | 2/1997 |
| WO | WO 2000/041650 | 7/2000 |
| WO | WO 2000/064655 | 11/2000 |
| WO | WO 2001/060286 | 8/2001 |

(56)  References Cited

FOREIGN PATENT DOCUMENTS

| WO | WO 2001/089435 | 11/2001 |
| WO | WO 2001/097742 | 12/2001 |
| WO | WO 2002/051338 | 7/2002 |
| WO | WO 2003/071339 | 8/2003 |
| WO | WO 2004/010895 | 2/2004 |
| WO | WO 2004/046768 | 6/2004 |
| WO | WO 2004/072689 | 8/2004 |
| WO | WO 2005/018504 | 3/2005 |
| WO | WO 2005/084588 | 9/2005 |
| WO | WO 2006/004707 | 1/2006 |
| WO | WO 2006/047383 | 5/2006 |
| WO | WO 2006/088440 | 8/2006 |
| WO | WO 2007/005529 | 1/2007 |
| WO | WO 2007/005692 | 1/2007 |
| WO | WO 2007/030095 | 3/2007 |
| WO | WO 2007/061688 | 5/2007 |
| WO | WO 2007/128423 | 11/2007 |
| WO | WO 2007/138564 | 12/2007 |
| WO | WO 2009/015161 | 1/2009 |
| WO | WO 2009/015226 | 1/2009 |
| WO | WO 2009/100322 | 8/2009 |
| WO | WO 2009/154455 | 12/2009 |
| WO | WO 2011/106435 | 9/2011 |
| WO | WO 2011/119334 | 9/2011 |
| WO | WO 2012/006186 | 1/2012 |
| WO | WO 2013/070924 | 5/2013 |
| WO | WO 2013/142323 | 9/2013 |
| WO | WO 2014/095611 | 6/2014 |
| WO | WO 2014/152017 | 9/2014 |
| WO | WO 2016/201351 | 12/2016 |
| WO | WO 2017/079733 | 5/2017 |
| WO | WO 2023/022958 | 2/2023 |

OTHER PUBLICATIONS

Baughman, "Avoiding the shrink," *Nature*, vol. 425, pp. 667, Oct. 16, 2003.

Conlisk, A. T. et al. "Mass Transfer and Flow in Electrically Charged Micro- and Nano-channels," *Analytical Chemistry*, vol. 74; iss. 9; pp. 2139-2150; May 2002.

DIY Extra, "Creating Butt Joints," https://www.diy-extra.co.uk/butt-joints.html, 2021, accessed Nov. 18, 2021.

Dubbelman et al. "The Thickness of the Aging Human Lens Obtained from Corrected Scheimpflug Images," *Optometry & Vision Science*; vo. 78; iss. 6; pp. 411-416; Jun. 2001.

Gorder, P. F.; Electricity can pump medicine in implanted medical devices; Ohio State Research News; 3 pgs.; May 2, 2002 (printed from internet Aug. 19, 2010).

Gordon, "Applications of shape memory polyurethanes," *Proceedings of the First Intl Conf. on Shape Memory and Superelastic Tech.*, Asilomar Conference Center, Pacific Grove, CA, USA, pp. 115-120, Mar. 1994.

Gruber et al. "Exhaustive soxhlet extraction for the complete removal of residual compounds," *Journal of Biomedical Materials Research*, vol. 53; No. 5; pp. 445-448; Mar. 2000.

Jeon et al., "Shape memory and nanostructure in poly(norbornyl-POSS) copolymers," *Polymer International*, vol. 49, pp. 453-457, May 2000.

Kim et al., "Polyurethanes having shape memory effects," *Polymer*, vol. 37, No. 26, pp. 5781-5793, Dec. 1996.

Lakes et al., "Dramatically stiffer elastic composite materials due to negative stiffness phase?," *Journal of the Mechanics and Physics of Solids*, vol. 50, pp. 979-1009, May 2002.

Lakes et al., "Extreme damping in composite materials with negative-stiffness inclusions," *Nature*, vol. 410, pp. 565-567, Mar. 29, 2001.

Lakes et al., "Microbuckling instability in elastomeric cellular sollids," *J. Materials Science*, vol. 28, pp. 4667-4672, Jan. 1993.

Lakes, "A broader view of membranes," *Nature*, vol. 414, pp. 503-504, Nov. 29, 2001.

Lakes, "Deformations in extreme matter," *Science*; perspectives; vol. 288; No. 5473; pp. 1976-1977; Jun. 16, 2000.

Lakes, "Extreme damping in compliant composites with a negative-stiffness phase," *Philosophical Magazine Letters*, vol. 81, No. 2, pp. 95-100, Feb. 2001.

Lakes, "Extreme damping in composite materials with a negative stiffness phase," *Physical Review Letters*, vol. 86, No. 13, pp. 2897-2900, Mar. 26, 2001.

Lakes, "Negative poisson's ratio materials," *Science*, vol. 238, pp. 551, Oct. 23, 1987.

Lakes, "No contractile obligations," *Nature*, vol. 358, pp. 713-714, Dec. 31, 1992.

Langenbucher et al., "Computerized calculation scheme for toric intraocular lenses," *Acta Ophthalmologica Scandinavica*, vol. 82, No. 3, pp. 270-276, Jun. 2004.

Lendlein et al., "Biodegradable, elastic shape-memory polymers for potential biomedical applications", *Science*; vol. 296; pp. 1673-1676; May 31, 2002.

Lendlein et al., "Shape-memory polymers," *Angew. Chem. Int. Ed.*; vol. 41; pp. 2034-2057; Jun. 2002.

Li et al., "Crystallinity and morphology of segmented polyurethanes with different soft-segment length," *Journal of Applied Polymer Science*, vol. 62, pp. 631-638, Oct. 1996.

Liu et al., "Thermomechanical characterization of a tailored series of shape memory polymers," *Journal of Applied Medical Polymers*, vol. 6, No. 2, Dec. 2002.

Mather et al., "Strain recovery in POSS hybrid thermoplastics," *Polymer Preprints*, vol. 41, No. 1, pp. 528-529, Feb. 2000.

Metcalfe et al., "Cold hibernated elastic memory foams for endovascular interventions," Biomaterials, vol. 24, pp. 491-497, Feb. 2003.

Qiao et al.; Bio-inspired accommodating fluidic intraocular lens; *Optics Letters*; vol. 34; No. 20; pp. 3214-3216; Oct. 15, 2009.

Rosales et al.; Pentacam Scheimpflug QuantitativeImaging of the Crystalline Lens andIntraocular Lens; J. Refractive Surgery; vol. 25; pp. 421-428; May 2009.

Takahashi et al., "Structure and properties of shape-memory polyurethane block copolymers," *Journal of Applied Polymer Science*, vol. 60, pp. 1061-1069, May 1996.

Tehrani et al. "Capsule measuring ring to predict capsular bag diameter and follow its course after foldable intraocular lens implantation," *J Cataract Refract Surg.*; vol. 29; No. 11; pp. 2127-2134; Nov. 29, 2003.

Tobushi et al., "Thermomechanical properties of shape memory polymers of polyurethane series and their applications," *Journal de Physique IV, Colloque C1*, vol. 6, pp. 377-384, Aug. 1996.

Vass et al. "Prediction of pseudophakic capsular bag diameter based on biometric variables," *J Cataract Refract Surg.*; vol. 25; pp. 1376-1381; Oct. 1999.

Wang et al., "Deformation of extreme viscoelastic metals and composites," *Materials Science and Enginerring A*, vol. 370, pp. 41-49, Apr. 15, 2004.

Wang et al., "Extreme stiffness systems due to negative stiffness elements," *American Journal of Physics*, vol. 72, No. 1, pp. 40-50, Jan. 2004.

Wang et al., "Stable extremely-high-damping discrete viscoelastic systems due to native stiffness elements," *Applied Physics Letters*, vol. 84, No. 22, pp. 4451-4453, May 31, 2004.

Wyant et al.; "Basic Wavefront Aberration Theory for Optical Metrology," *Applied Optics and Optical Engineering*, vol. XI, pp. 1, 28-39, Aug. 10, 1992.

Xu et al., "Making negative poisson's ratio microstructures by soft lithography," *Advanced Materials*, vol. 11, No. 14, pp. 1186-1189, Jun. 1999.

Arkles, B. Grignard Reagents and Silanes, Reprinted from G. Silverman and P. Rakita. *Handbook of Grignard Reagents*, pp. 667-675 (10 pages), 1996, Marcel Dekker Inc.

Cella, J. et al. "Procedures for the preparation of silanols," *Journal of Organometallic Chemistry*, vol. 480, No. 1-2, pp. 23-26, Oct. 1994.

Hofmann, R. et al. "Fifty years of hydrosilylation in polymer science: A review of current trends of low-cost transition-metal and metal-free catalysts, non-thermally triggered hydrosilylation reactions, and industrial applications," *Polymers*, vol. 9, No. 10, 534, 37 pages, Oct. 20, 2017.

(56) References Cited

OTHER PUBLICATIONS

Naganawa, Y. et al. "Hydrosilylation reactions of functionalized alkenes," *Tetrahedron Letters*, vol. 61, No. 11, pp. 151513, Mar. 12, 2020.

Product Description EGM-2, Devely, 2022, 1 page, retrieved from internet: https://www.develycn.com/sale-7836042-ethylene-glycol-dimethacrylate-egdma.html.

Suzuki, T. et al. "Miscibility and transesterification in bisphenol A polycarbonate/poly (ethylene terephthalate) blends," *Polymer*, vol. 30, No. 7 pp. 1287-1297, Jul. 1989.

Zhao, H. et al., "The effect of chromatic dispersion on pseudophakic optical performance," *Br J Opthalmol*, vol. 91, pp. 1225-1229, May 2, 2007.

* cited by examiner

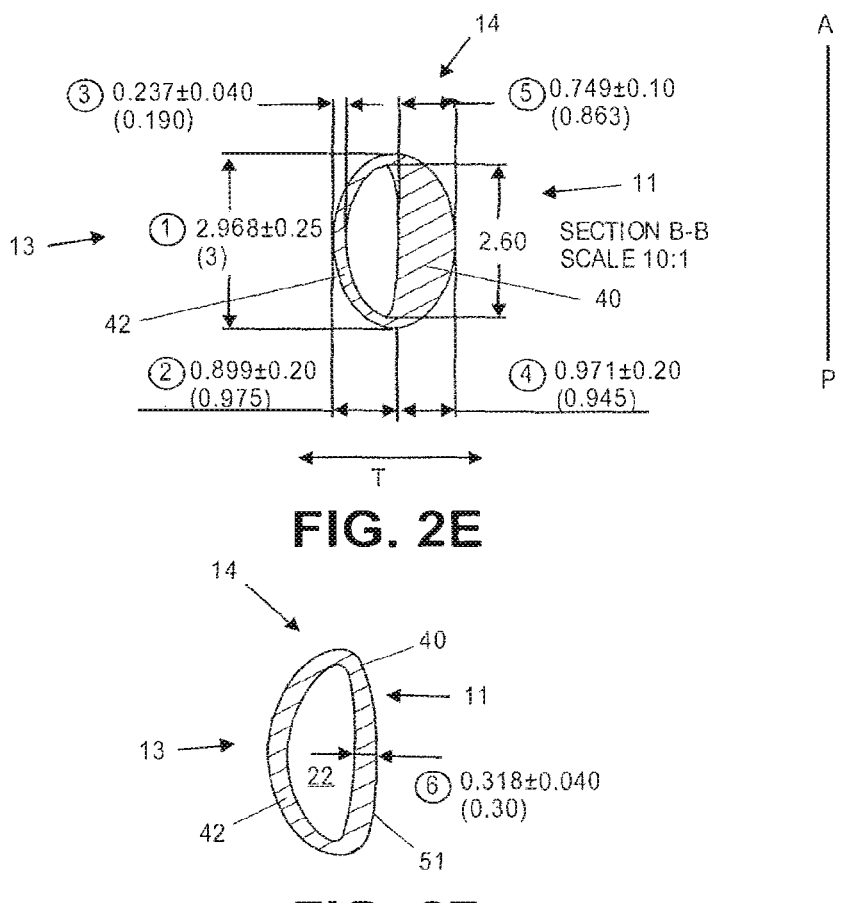
③ 0.237±0.040
(0.190)
⑤ 0.749±0.10
(0.863)
14
① 2.968±0.25
(3)
13
2.60
SECTION B-B
SCALE 10:1
11
42
40
② 0.899±0.20
(0.975)
④ 0.971±0.20
(0.945)
A
P
T
FIG. 2E
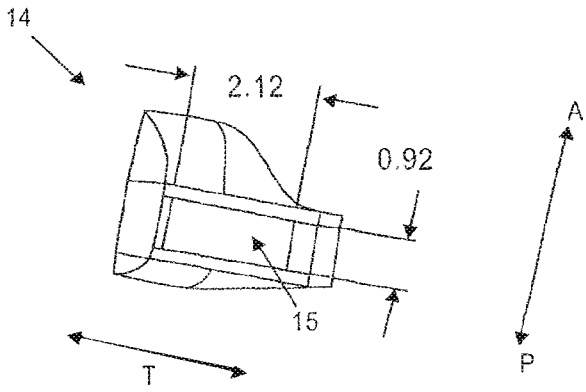
14
40
11
13
22
42
⑥ 0.318±0.040
(0.30)
51
FIG. 2F
14
2.12
0.92
15
A
P
T
FIG. 2G Section A-A Section A-A

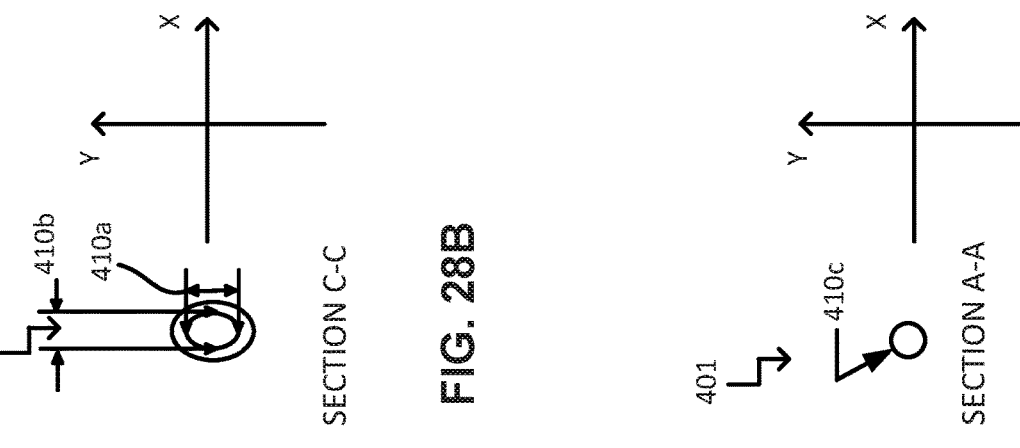
SECTION C-C
FIG. 28B
SECTION A-A
FIG. 28D
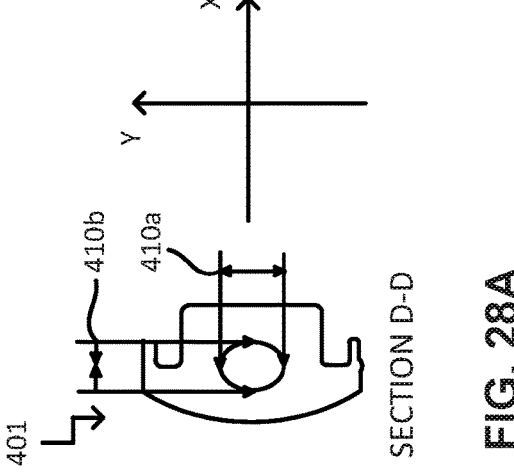
SECTION D-D
FIG. 28A
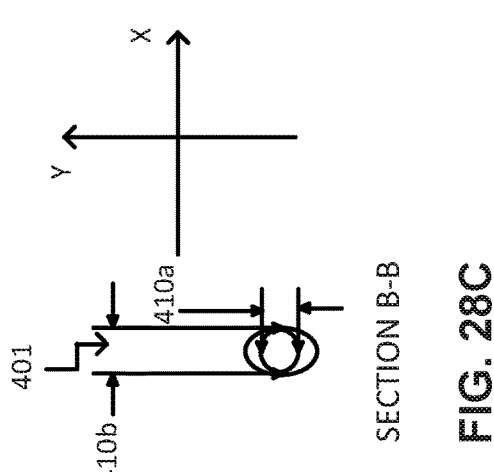
SECTION B-B
FIG. 28C

ACCOMMODATING INTRAOCULAR LENSES AND METHODS OF MANUFACTURING

CROSS REFERENCE TO RELATED APPLICATIONS

This application is a continuation of U.S. patent application Ser. No. 15/760,640 filed on Mar. 16, 2018, now U.S. Pat. No. 11,426,270, which is a U.S. national application filed under 35 U.S.C. 371 to PCT International Application No. PCT/US2016/060799 filed Nov. 7, 2016, which claims priority to U.S. Provisional Patent Application Nos. 62/252,260 filed on Nov. 6, 2015; 62/321,678 filed on Apr. 12, 2016; 62/357,785 filed on Jul. 1, 2016; 62/321,704 filed on Apr. 12, 2016; 62/321,666 filed on Apr. 12, 2016; 62/321,665 filed on Apr. 12, 2016; 62/321,705 filed on Apr. 12, 2016; 62/321,684 filed on Apr. 12, 2016; 62/321,670 filed on Apr. 12, 2016 and 62/377,402 filed on Aug. 19, 2016; the contents of which are incorporated herein by reference in their entireties.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Fluid-driven, accommodating intraocular lenses have been described. This disclosure describes a wide variety of aspects of exemplary intraocular lenses that may provide benefits to some fluid-driven, accommodating intraocular lenses. For example, it may be beneficial for a fluid-driven intraocular lens to have an aspherical configuration after it has been manufactured.

SUMMARY

One aspect of the disclosure is a method of manufacturing an optic of an accommodating intraocular lens to have an aspheric lens surface, comprising: providing an optic comprising an anterior element and a posterior element that at least partially define an optic fluid chamber, wherein at least one of the anterior element and the posterior element has an external surface that is spherical; and prior to inserting the accommodating intraocular lens into an eye, changing the shape of the at least one of the anterior element and the posterior element from the spherical configuration to an aspherical configuration.

In some embodiments changing the shape of the at least one of the anterior element and the posterior element from the spherical configuration to an aspherical configuration comprises adding fluid to the optic fluid chamber so as to increase the fluid pressure within the optic chamber and cause the at least one of the anterior element and the posterior element to deform from the spherical configuration to the aspherical configuration. Prior to adding fluid, the method can include securing at least one haptic to the optic.

In some embodiments providing the optic comprises bonding the anterior element to the posterior element.

In some embodiments the method also includes machining at least one of the anterior element and the posterior element.

In some embodiments, prior to changing the shape of the at least one of the anterior element and the posterior element from the spherical configuration to an aspherical configuration, the optic has a 10-15 D base state.

One aspect of the disclosure is a fluid-filled intraocular lens, comprising: an optic portion comprising an anterior element with an anterior optical surface and a posterior element with a posterior optical surface, the anterior element and the posterior element defining an optic fluid chamber, wherein at least one of the anterior optical surface and the posterior optical surface has an aspherical configuration in an as-manufactured state, prior to insertion in an eye.

One aspect of the disclosure is an intraocular lens, comprising: an optic portion; and a peripheral portion including a peripheral fluid chamber, the peripheral portion having a cross section, in a plane passing through an optical axis of the optic portion, in which the fluid chamber is disposed in a radially outer portion of the peripheral portion, and wherein a radially inner portion of the peripheral chamber is non-fluid.

One aspect of the disclosure is an intraocular lens, comprising: an optic portion; and a peripheral portion including a peripheral fluid chamber, the peripheral portion, in a cross section of a plane passing through an optical axis of the optic portion, and in a direction orthogonal to an optical axis of the optic portion through a midpoint of the peripheral portion, having a radially inner fluid chamber wall thickness that is between four and twenty times the thickness of a radially outer fluid chamber wall thickness.

One aspect of the disclosure is an intraocular lens, comprising: an optic portion; and a peripheral portion including a peripheral fluid chamber, the peripheral portion, in a cross section of a plane passing through an optical axis of the optic portion, has an outer surface that is not symmetrical about every axis passing through the peripheral portion and parallel to an optical axis of the optic portion, and wherein the peripheral portion has, in a direction orthogonal to an optical axis of the optic portion through a midpoint of the peripheral portion, having a radially inner fluid chamber wall thickness greater than a radially outer fluid chamber wall thickness.

One aspect of the disclosure is an intraocular lens, comprising: an optic portion; and a peripheral portion including a peripheral fluid chamber, the peripheral portion, in a cross section of a plane passing through an optical axis of the optic portion, having a height dimension measured in an anterior to posterior direction, wherein the greatest height of the peripheral portion in a radially outer half of the peripheral portion is greater than the greatest height of the peripheral portion in a radially inner half of the peripheral portion.

One aspect of the disclosure is an intraocular lens, comprising: an optic portion coupled to a peripheral portion at a coupling, the coupling comprising a radially inner surface of the peripheral portion interfacing a radially outer peripheral edge of the optic portion.

In some embodiments the radially inner surface of the peripheral portion has a first end with a configuration that is different than a second end of the inner surface. The peripheral portion can include a haptic with a coupled end and a free end, the first end being closer to the haptic free end than the coupled end. The haptic can have a configuration that follows a radially outer peripheral curvature of the optic from the haptic coupled end to the free end.

In some embodiments the first end has a greater surface area than the second end of the radially inner surface. The first end can have a tapered end configuration, wherein the taper is toward a free end of the peripheral portion.

In some embodiments the radially inner surface of the peripheral portion defines a peripheral portion fluid port.

One aspect of the disclosure is an intraocular lens, comprising an optic body, a projection extending radially outwards from a peripheral surface of the optic body, and a peripheral non-optic body having a first portion secured to the projection.

In some embodiments a radially inner surface of the first portion of the peripheral non-optic body follows a radially peripheral surface of the projection.

In some embodiments the projection and the first portion interface at a butt joint, with optionally flat or curved relative surfaces.

In some embodiments a radially peripheral surface of the projection comprises a flat surface, optionally entirely flat. A radially inner surface of the first portion of the peripheral non-optic body can comprise a flat surface, optionally entirely flat.

In some embodiments a radially peripheral surface of the projection comprises a curved surface, optionally entirely curved. A radially inner surface of the first portion of the peripheral non-optic body can comprise a curved surface, optionally entirely curved.

In some embodiments a radially peripheral surface of the projection is between 10 microns and 1 mm, optionally, 10 microns to 500 microns, farther away radially from a center of the optic body than the peripheral surface of the optic body.

In some embodiments the projection extends between 10 microns and 1 mm, optionally between 10 microns and 500 microns, from the peripheral surface of the optic body.

In some embodiments the optic body and the projection are a single integral body.

In some embodiments the projection is attached to the optic body.

In some embodiments the optic body comprises a posterior element and an anterior element, optionally defining a fluid chamber therebetween. The posterior element can comprise the projection. The anterior element may comprise the projection.

In some embodiments the peripheral non-optic body further comprises a free second portion disposed away from the first portion.

In some embodiments the peripheral non-optic body comprises a peripheral fluid chamber.

In some embodiments the projection comprises at least one channel, and optionally at least two channels, in fluid communication with a peripheral fluid chamber in the peripheral non-optic body.

In some embodiments the peripheral non-optic body has a radially inner surface, optionally with a slight curve, coupled to the projection, wherein the projection is disposed on a radially outer peripheral edge of the optic body.

In some embodiments the peripheral non-optic body is adapted to deform in response to forces on the peripheral non-optic body due to ciliary muscle movement to thereby move a fluid between a peripheral fluid chamber in the peripheral non-optic body and an optic fluid chamber in the optic body to change an optical parameter of the intraocular lens.

In some embodiments the peripheral non-optic body comprises an opening configured to interface with the projection.

In some embodiments the projection is sized and configured to be disposed within and interface with an opening in the peripheral non-optic body.

One aspect of the disclosure is an intraocular lens comprising an optic body and a peripheral non-optic body, the optic body having, in a top view, an outer edge at least a portion of which is an arc, and wherein the peripheral non-optic body is coupled to the optic body projection at a location radially outward relative to the curve of the arc.

One aspect of the disclosure an intraocular lens wherein an adhesive between first and second components has a modulus of elasticity of between about 0.4 and 1000 MPa, such as between about 1 MPa and 600 MPa.

One aspect of the disclosure is an intraocular lens wherein an adhesive is 50-85% of a cross linkable polymer of a first polymeric material of the intraocular lens.

One aspect of the disclosure is an intraocular lens wherein an adhesive comprises between 7.5% and 30% of a reactive acrylic monomer diluent.

One aspect of the disclosure is an intraocular lens wherein the adhesive includes lauryl methacrylate or similar material in an amount between 2.5% and 30%.

One aspect of the disclosure is an intraocular lens, optionally, accommodating, comprising an optic portion; a peripheral portion; and at least one ridge extending along at least a portion of the length of the peripheral portion.

One aspect of the disclosure is an intraocular lens, wherein a tip of a first haptic overlays, optionally tapered, a second haptic, in a top view.

One aspect of the disclosure is an intraocular lens, optionally accommodating, including an optic portion; and a peripheral portion coupled to the optic portion, the peripheral portion comprising a first haptic and a second haptic, wherein the first haptic and the second haptic are configured to be closely fit together to reduce gaps therebetween, optionally overlapping in a top view.

One aspect of the disclosure is an intraocular lens, optionally, accommodating, comprising an optic portion comprising an opaque periphery around at least a portion of the optic portion; and a peripheral non-optic portion secured to the optic portion and disposed radially outward relative to the optic portion.

One aspect of the disclosure a method of air removal during loading of an intraocular lens, comprising: providing an intraocular lens; loading the intraocular lens into a cartridge; inserting a viscoelastic delivery device over the intraocular lens; injecting a fluid from the viscoelastic delivery device; and removing air from over a portion of the intraocular lens and away from the intraocular lens.

One aspect of the disclosure is a loading carrier for loading an intraocular lens and removing air over a portion of the intraocular lens in preparation for delivering the intraocular lens into an eye, comprising a base member comprising an intraocular lens receiving region; a loading member configured to advance the intraocular lens towards a delivery lumen; and an opening configured to allow insertion of a viscoelastic delivery device over a portion of the intraocular lens to remove air away from the intraocular lens.

One aspect of the disclosure is a method of air venting in a delivery system of an intraocular lens, comprising: providing a loading carrier for a intraocular lens; loading the intraocular lens into a cartridge from the loading carrier, mounting a plunger assemble to the cartridge; injecting a viscoelastic fluid from the plunger assemble; and removing air out of the plunger assembly.

One aspect of the disclosure is a method of removing air from an area adjacent an intraocular lens, comprising: providing an intraocular lens within a loading device in a loaded configuration; and delivering a viscoelastic material, optionally with a syringe, in the vicinity of the intraocular lens to remove air bubbles proximate the intraocular lens.

One aspect of the disclosure is an apparatus for delivering an intraocular lens into an eye, comprising: a distal tip adapted to deliver an intraocular lens into an eye; and a lumen extending from the proximal region to the distal tip, the lumen comprising a cross section having a first axis and a second axis of an internal ellipse; a first portion configured to fold the intraocular lens without stretching the intraocular lens out, a second portion configured to form a substantial seal between an inner wall and the intraocular lens, and a third portion configured to compress the intraocular lens to extend the intraocular lens in length.

One aspect of the disclosure is a method for delivering an intraocular lens into an eye, comprising: engaging a delivery device to a loading carrier to accept the intraocular lens; folding the intraocular lens without stretching the intraocular lens out; forming a seal between an inner wall of the delivery device and the intraocular lens; compressing the intraocular lens to extend the intraocular lens in length; and delivering the intraocular lens into the eye.

One aspect of the disclosure a delivery device for delivering an intraocular lens into an eye, comprising a delivery lumen configured to deform therein an intraocular lens during delivery out of a distal port; wherein in a first cross section the inner lumen has an elliptical shape, and in a second cross section distal to the first cross section, the inner lumen has an elliptical shape, wherein in the first cross section the elliptical shape has a major axis and minor axis, and wherein in the second cross section the elliptical shape has a major axis and minor axis, wherein the major axis of the first cross section is perpendicular to the major axis of the second cross section.

BRIEF DESCRIPTION OF THE DRAWINGS

FIGS. 2D, 2E, and 2F illustrate sectional views of the haptic from FIG. 2A.

FIG. 2G illustrates an opening in a first end of the haptic from FIGS. 2A-2C.

FIGS. 28A, 28B, 28C, and 28D illustrate exemplary internal cross sections of the cartridge in FIG. 27.

DETAILED DESCRIPTION

The disclosure relates generally to accommodating intraocular lenses. In some embodiments the accommodating intraocular lenses described herein are adapted to be positioned within a native capsular bag in which a native lens has been removed. In these embodiments a peripheral non-optic portion (i.e., a portion not specifically adapted to focus light on the retina) is adapted to respond to capsular bag reshaping due to ciliary muscle relaxation and contraction. The response is a deformation of the peripheral portion that causes a fluid to be moved between the peripheral portion and an optic portion to change an optical parameter (e.g., power) of the intraocular lens.

Figure 1A:
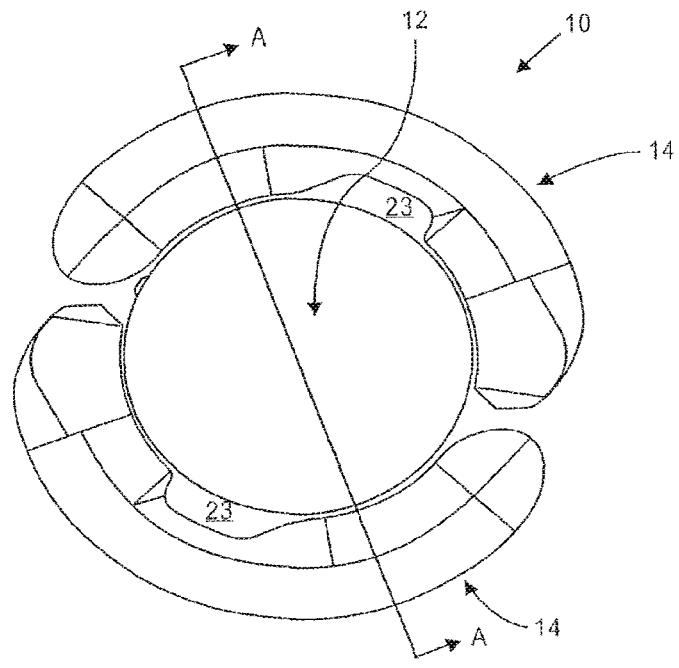
FIGS. 1A and 1B illustrate an exemplary accommodating intraocular lens.
Figure 1B:
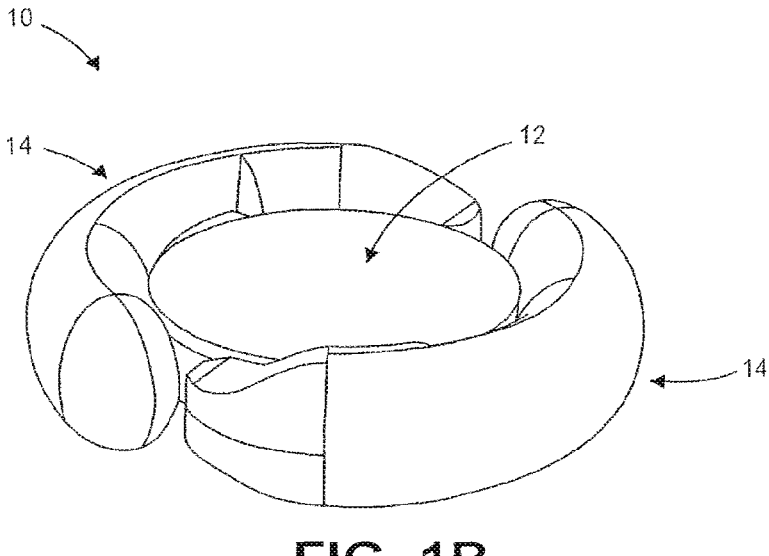

FIG. 1A is a top view illustrating accommodating intraocular lens 10 that includes optic portion 12 and a peripheral portion that in this embodiment includes first and second haptics 14 coupled to and extending peripherally from optic portion 12. Optic portion 12 is adapted to refract light that enters the eye onto the retina. Haptics 14 are configured to engage a capsular bag and are adapted to deform in response to ciliary muscle related capsular bag reshaping. FIG. 1B is a perspective view of intraocular lens 10 showing optic portion 12 and haptics 14 coupled to optic portion 12.

The haptics are in fluid communication with the optic portion. Each haptic has a fluid chamber that is in fluid communication with an optic chamber in the optic portion. The haptics are formed of a deformable material and are adapted to engage the capsular bag and deform in response to ciliary muscle related capsular bag reshaping. When the haptics deform the volume of the haptic fluid chamber changes, causing a fluid disposed in the haptic fluid chambers and the optic fluid chamber to either move into the optic fluid chamber from the haptic fluid chambers, or into the haptic fluid chambers from the optic fluid chamber. When the volume of the haptic fluid chambers decreases, the fluid is moved into the optic fluid chamber. When the volume of the haptic fluid chamber increases, fluid is moved into the haptic fluid chambers from the optic fluid chamber. The fluid flow into and out of the optic fluid chamber changes the configuration of the optic portion and the power of the intraocular lens.

Figure 1C:
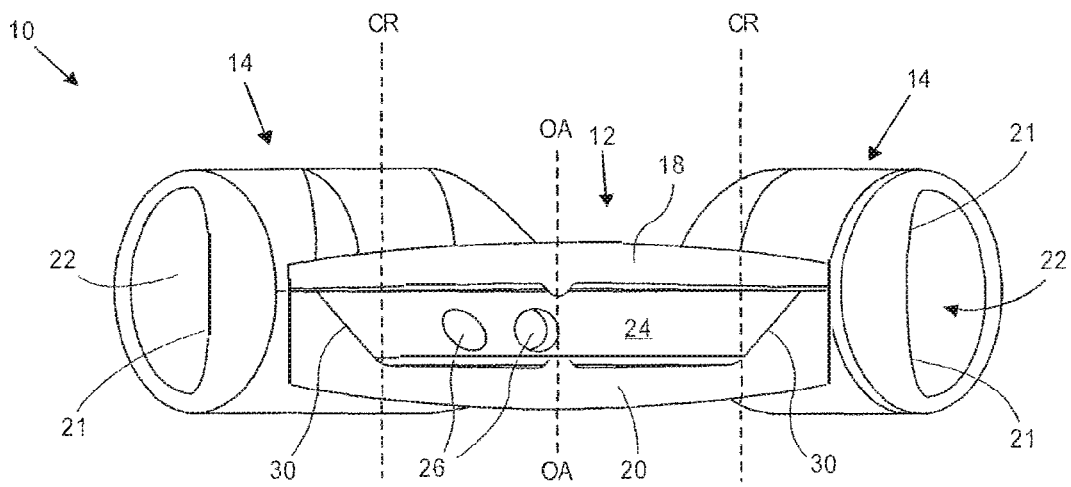
FIG. 1C illustrates a sectional view of the accommodating intraocular lens from FIGS. 1A and 1B.

FIG. 1C is a side sectional view through Section A-A indicated in FIG. 1A. Optic portion 12 includes deformable anterior element 18 secured to deformable posterior element 20. Each haptic 14 includes a fluid chamber 22 that is in fluid communication with optic fluid chamber 24 in optic portion 12. Only the coupling between the haptic 14 to the left in the figure and option portion 12 is shown (although obscured) in the sectional view of FIG. 1C. The haptic fluid chamber 22 to the left in the figure is shown in fluid communication with optic fluid chamber 24 via two apertures 26, which are formed in posterior element 20. The haptic 14 to the right in FIG. 1C is in fluid communication with optic chamber 24 via two additional apertures also formed in posterior element (not shown) substantially 180 degrees from the apertures shown.

Figure 1D:
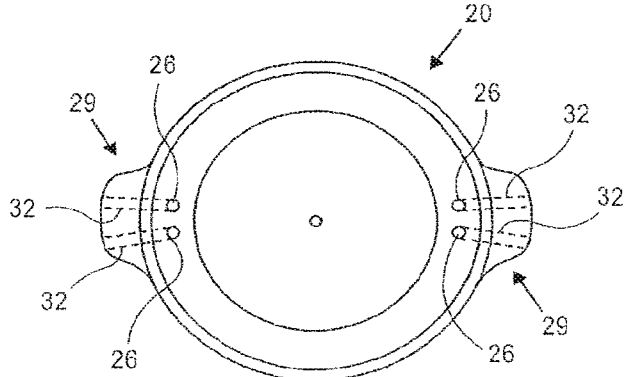
FIG. 1D is a top view of an exemplary posterior element of an accommodating intraocular lens.

FIG. 1D is a top view of posterior element 20 (anterior element 18 and haptics 14 not shown). Posterior element 20 includes buttress portions 29 in which channels 32 are formed. Channels 32 provide fluid communication between optic portion 12 and haptics 14. Apertures 26 are disposed at one end of channels 32. The optic fluid chamber 24 is therefore in fluid communication with a single haptic via two fluid channels. Buttress portions 29 are configured and sized to be disposed within an opening formed in haptics 14 that defines one end of the haptic fluid chamber, as described below. Each of buttress portions 29 includes two channels formed therein. A first channel in a first buttress is in alignment with a first channel in the second buttress. The second channel in the first buttress is in alignment with the second channel in the second buttress.

There are exemplary advantages to having two channels in each buttress as opposed to one channel. A design with two channels rather than one channel helps maintain dimensional stability during assembly, which can be important when assembling flexible and thin components. Additionally, it was observed through experimentation that some one-channel designs may not provide adequate optical quality throughout the range of accommodation. In particular, lens astigmatism may occur in some one-channel designs, particularly as the intraocular lens accommodated. It was discovered that the two-channel buttress designs described herein can help reduced astigmatism or the likelihood of astigmatism, particularly as the lens accommodated. Astigmatism is reduced in these embodiments because the stiffness of the buttress is increased by the rib portion between the two channels. The additional stiffness results in less deflection due to pressure changes in the channels. Less deflection due to the pressure changes in the channels results in less astigmatism. In some embodiments the channels are between about 0.4 mm and about 0.6 mm in diameter. In some embodiments the channels are about 0.5 mm in diameter. In some embodiments the distance between the apertures is about 0.1 mm to about 1.0 mm.

Figure 1E:
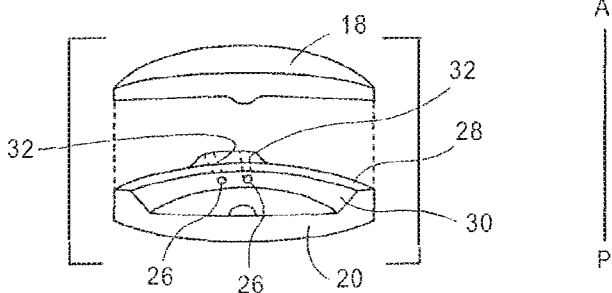
FIG. 1E is a sectional assembly view of an exemplary optic portion of an accommodating intraocular lens.

FIG. 1E is a side assembly view through section A-A of optic portion 12, which includes anterior element 18 and posterior element 20 (haptics not shown for clarity). By including fluid channels 32 in posterior element 20, posterior element 20 needs to have enough structure through which the channels 32 can be formed. Buttress portions 29 provide that structures in which channels 32 can be formed. At its peripheral-most portion posterior element 20 is taller than anterior element 18 in the anterior-to-posterior direction. In alternative embodiments, the channels can be formed in anterior element 18 rather than posterior element 20. The anterior element would include buttress portions 29 or other similar structure to provide structure in which the channels can be formed. In these alternative embodiments the posterior element could be formed similarly to anterior element 18.

As shown in FIG. 1E, posterior element 20 is secured to anterior element 18 at peripheral surface 28, which extends around the periphery of posterior element 20 and is a flat surface. Elements 18 and 20 can be secured together using known biocompatible adhesives. Anterior element 18 and posterior element 20 can also be formed from one material to eliminate the need to secure two elements together. In some embodiments the diameter of the region at which anterior element 18 and posterior element 20 are secured to one another is about 5.4 mm to about 6 mm in diameter.

In some embodiments the thickness of anterior element 18 (measured in the anterior-to-posterior direction) is greater along the optical axis ("OA" in FIG. 1C) than at the periphery. In some embodiments the thickness increases continuously from the periphery towards the thickest portion along the optical axis.

In some embodiments the thickness of posterior element 20 decreases from the location along the optical axis towards the edge of central region "CR" identified in FIG. 1C. The thickness increases again radially outward of central region CR towards the periphery, as can be seen in FIG. 1C. In some particular embodiments central region CR is about 3.75 mm in diameter. The apertures are formed in beveled surface 30.

In some embodiments the thickness of posterior element 20 along the optical axis is between about 0.45 mm and about 0.55 mm and the thickness at the periphery of posterior element 20 is between about 1.0 mm and about 1.3.

In some embodiments the thickness of posterior element 20 along the optical axis is about 0.5 mm and the thickness at the periphery of posterior element 20 is about 1.14 mm.

In some embodiments the thickness of anterior element 18 along the optical axis is between about 0.45 mm to about 0.55 mm, and in some embodiments is between about 0.50 mm to about 0.52 mm. In some embodiments the thickness at the periphery of anterior element 18 is between about 0.15 mm and about 0.4 mm, and in some embodiments is between about 0.19 mm and about 0.38 mm.

In one particular embodiment the thickness of anterior element 18 along the optical axis is about 0.52 mm and the thickness of the periphery of anterior element 18 is about 0.38 mm, and the thickness of posterior element 20 along the optical axis is about 0.5 mm and the thickness at the periphery of posterior element 20 is about 1.14 mm.

In one particular embodiment the thickness of anterior element 18 along the optical axis is about 0.5 mm and the thickness of the periphery of anterior element 18 is about 0.3 mm, and the thickness of posterior element 20 along the optical axis is about 0.5 mm and the thickness at the periphery of posterior element 20 is about 1.14 mm.

In one particular embodiment the thickness of anterior element 18 along the optical axis is about 0.51 mm and the thickness of the periphery of anterior element 18 is about 0.24 mm, and the thickness of posterior element 20 along the optical axis is about 0.5 mm and the thickness at the periphery of posterior element 20 is about 1.14 mm.

In one particular embodiment the thickness of anterior element 18 along the optical axis is about 0.52 mm and the thickness of the periphery of anterior element 18 is about 0.19 mm, and the thickness of posterior element 20 along the optical axis is about 0.5 mm and the thickness at the periphery of posterior element 20 is about 1.14 mm.

The optic portion is adapted to maintain optical quality throughout accommodation. This ensures that as the accommodating intraocular lens transitions between the dis-accommodated and accommodated configurations, the optic portion maintains optical quality. A number of factors contribute to this beneficial feature of the accommodating intraocular lenses herein. These factors include the peripheral region at which anterior element 18 is secured to posterior element 20, the shape profile of the anterior element 18 and posterior element 20 inside central region CR of the optic portion (see FIG. 1C), and the thickness profiles of anterior element 18 and posterior element 20. These contributing factors ensure that both the anterior and posterior elements flex in such a way as to maintain the shape necessary to maintain optical quality across a range of optical powers.

Figure 1F:
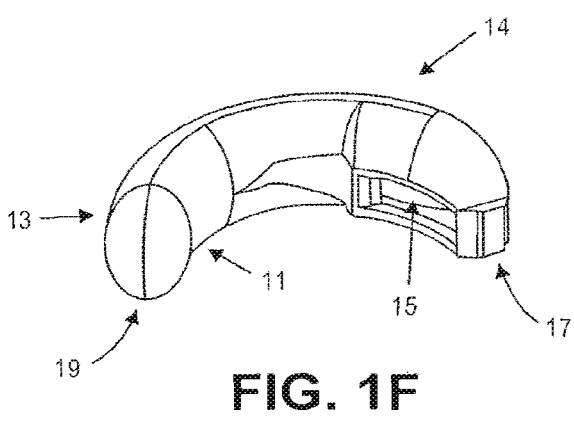
FIGS. 1F and 1G illustrate an exemplary haptic.

FIG. 1F illustrates one haptic 14 from intraocular lens 10 (optic portion 12 and the second haptic not shown for clarity). Haptic 14 includes radially outer portion 13 adapted to face the direction of the zonules, and radially inner portion 11, which faces the periphery of the optic (not shown). Haptic 14 includes a first end region 17 which is secured to optic portion 12, and second end region 19 that is closed. Haptic 14 also includes opening 15 in first end region 17 that provides the fluid communication with the haptic. In this embodiment opening 15 is sized and configured to receive buttress portion 29 of optic portion 12 therein.

Figure 1G:
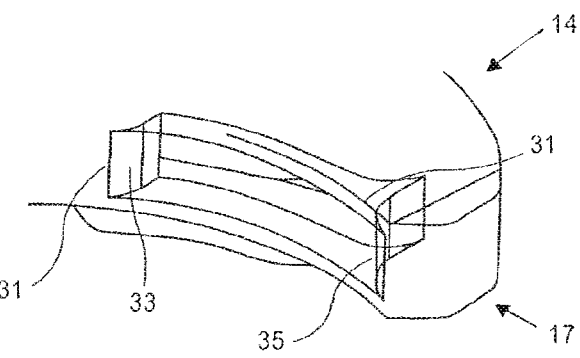

FIG. 1G is a close up view of opening 15 in haptic 14, which is adapted to receive buttress portion 29 therein. The opening 15 has curved surfaces 33 and 35 that are shaped to mate with curved surfaces on the optic buttress 29. Surface 31 surrounds opening 15 and provides a surface to which a corresponding surface of the optic can be secured.

Figure 1H:
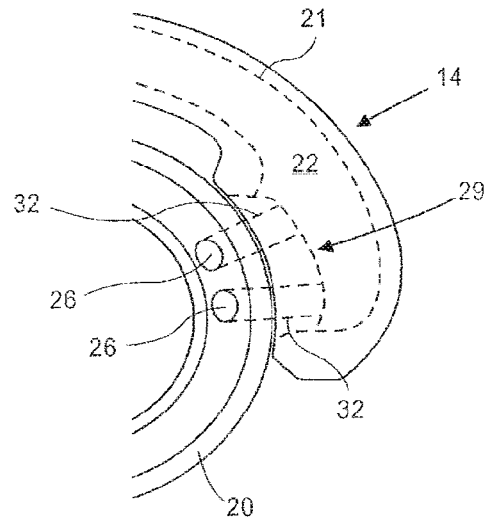
FIG. 1H illustrate an exemplary coupling between an optic portion and a haptic.

FIG. 1H is a top close up view of buttress portion 29 (in phantom) from posterior element 20 disposed within opening 15 in haptic 14 (anterior element of the optic not shown for clarity). Channels 32 are shown in phantom. Haptic 14 includes fluid chamber 22 defined by inner surface 21. Fluid moves between the optic fluid chamber and haptic fluid chamber 22 through channels 32 upon the deformation of haptic 14.

Figure 2A:
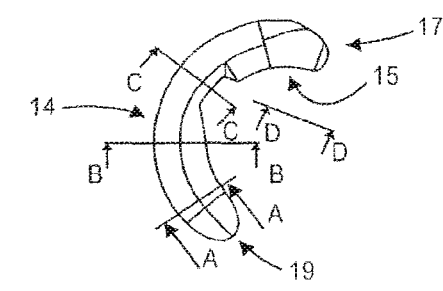
FIGS. 2A, 2B, and 2C illustrate an exemplary haptic.
Figure 2B:
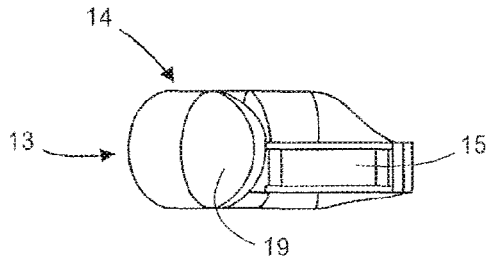
Figure 2C:
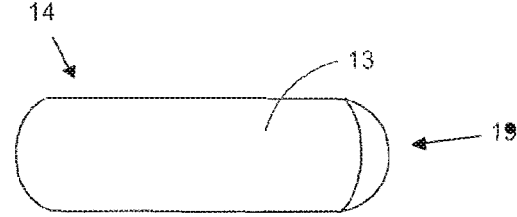

FIG. 2A is a top view showing one haptic 14 shown in FIGS. 1A-1H. The optic portion and the second haptic are not shown. Four sections A-D are identified through the haptic. FIG. 2B illustrates a side view of haptic 14, showing opening 15 and closed end 19. FIG. 2C is a side view of haptic 14 showing radially outer portion 13 and closed end 19.

Figure 2D:
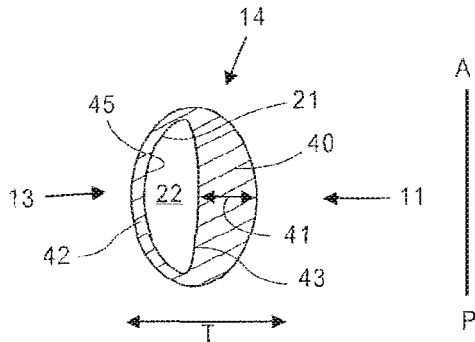

FIG. 2D is the cross sectional view through section A-A shown in FIG. 2A. Of the four sections shown in FIG. 2A, section A-A is the section closest to closed end 19. Radially inner portion 11 and radially outer portion 13 are identified. Fluid channel 22 defined by surface 21 is also shown. In this section the radially inner portion 40 is radially thicker (in the direction "T") than radially outer portion 42. Inner portion 40 provides the haptic's stiffness in the anterior-to-posterior direction that more predictably reshapes the capsule in the anterior-to-posterior direction. Radially inner portion 40 has a greatest thickness dimension 41, which is along an axis of symmetry in this cross section. The outer surface of haptic 14 has a generally elliptical configuration in which the greatest height dimension, in the anterior-to-posterior direction ("A-P"), is greater than the greatest thickness dimension (measured in the "T" dimension). The fluid chamber 22 has a general D-shaped configuration, in which the radially inner wall 43 is less curved (but not perfectly linear) than radial outer wall 45. Radially outer portion 42 engages the capsular bag where the zonules attach thereto, whereas the thicker radially portion 40 is disposed adjacent the optic.

FIG. 2E illustrates section B-B shown in FIG. 2A. Section B-B is substantially the same as section A-A, and FIG. 2E provides exemplary dimensions for both sections. Radially inner portion 40 has a greatest thickness along the midline of about 0.75 mm (in the radial direction "T"). Radially outer portion 42 has a thickness along the midline of about 0.24 mm. Fluid chamber 22 has a thickness of about 0.88 mm. Haptic 14 has a thickness along the midline of about 1.87 mm. The height of the haptic in the anterior to posterior dimension is about 2.97 mm. The height of the fluid chamber is about 2.60 mm. In this embodiment the thickness of the radially inner portion 40 is about 3 times the thickness of the radially outer portion 42. In some embodiments the thickness of the radially inner portion 40 is about 2 times the thickness of the radially outer portion 42. In some embodiments the thickness of the radially inner portion 40 is about 2 to about 3 times the thickness of the radially outer portion 42. In some embodiments the thickness of the radially inner portion 40 is about 1 to about 2 times the thickness of the radially outer portion 42.

Fluid chamber 22 is disposed in the radially outer portion of haptic 14. Substantially the entire radially inner region of haptic 14 in this section is bulk material. Since the fluid chamber 22 is defined by surfaces 43 and 45 (see FIG. 2D), the positioning and size of fluid chamber 22 depends on the thickness of the radially inner portion 40 and the radially outer portion 42.

FIG. 2F illustrates Section C-C shown in FIG. 1A. In Section C-C radially inner portion 40 is not as thick as radially inner portion 40 in sections A-A and B-B, although in Section C-C radially inner portion 40 is slightly thicker than radially outer portion 42. In this particular embodiment radially inner portion 40 is about 0.32 mm in Section C-C. Radially outer portion 42 has a thickness about the same as the radially outer thickness in Sections A-A and B-B, about 0.24 mm. The outer surface of haptic 14 does not have the same configuration as the outer surface in Sections A-A and Section B-B. In Section C-C the radially inner outer surface of haptic 51 is more linear than in Sections A-A and Section B-B, giving the outer surface of haptic in Section C-C a general D-shape. In Section C-C fluid chamber 22 has a general D-shape, as in Sections A-A and Section B-B. The haptic, in Section C-C has a fluid chamber configuration that is substantially the same as the fluid chamber configurations in Sections A-A and B-B, but has an outer surface with a configuration different than the configuration of the outer surface of haptic 14 in Sections A-A and B-B.

The thinner radially inner portion 40 in Section C-C also creates access pathways 23 that are shown in FIG. 1A. This space between optic portion 12 and haptics 14 allows a physician to insert one or more irrigation and/or aspiration devices into space 23 during the procedure and apply suction to remove viscoelastic fluid that may be used in the delivery of the intraocular lens into the eye. The pathways 23 could also be anywhere along the length of the haptic, and there could be more than one pathway 23. This application incorporates by reference the disclosure in FIGS. 23 and 24, and the textual description thereof, from U.S. Pub. No. 2008/0306588, which include a plurality of pathways in the haptics.

FIG. 2G shows a view through Section D-D from FIG. 2A. Haptic 14 includes opening 15 therein, which is adapted to receive the buttress from the optic portion as described herein. The height of opening 15 in this embodiment is about 0.92 mm. The width, or thickness, of the opening is about 2.12 mm.

Figure 3:
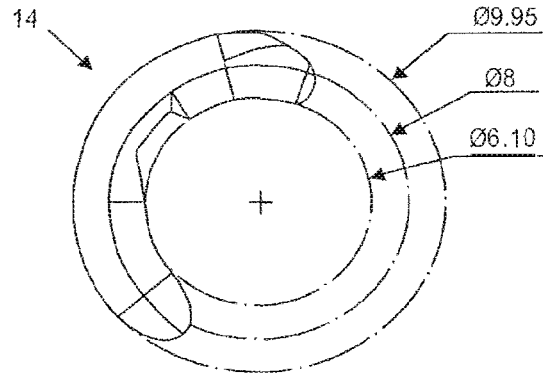
FIG. 3 illustrates exemplary diameters of an accommodating intraocular lens.

FIG. 3 illustrates relative diameters of optic portion 12 (not shown) and of the peripheral portion, which includes two haptics 14 (only one haptic is shown). In this embodiment the optic has a diameter of about 6.1 cm, while the entire accommodating intraocular lens, including the peripheral portion, has a diameter of about 9.95 cm. The dimensions provided are not intended to be strictly limiting.

Figure 4:
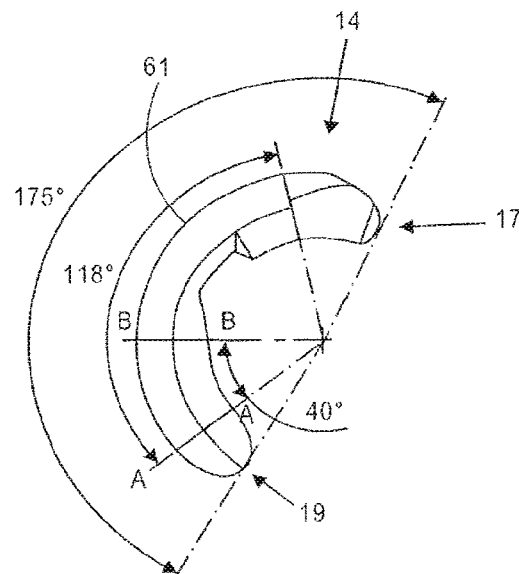
FIG. 4 illustrates an exemplary haptic.

FIG. 4 is a top view of haptic 14, showing that haptic 14 subtends an angle of about 175 degrees around optic (i.e., substantially 180 degrees). The optic portion is not shown for clarity. The two haptics therefore each subtend an angle of about 180 degrees around the optic. A first region 61 of haptic 14 is shown to subtend exemplary angle of about 118 degrees. This is the radially outermost portion of haptic 14, is adapted to engage the capsular bag, and is adapted to be most responsive to capsular shape changes. Region 61 can be thought of as the most responsive part of haptic 14.

The angle between Sections A-A and B-B, which are considered the boundaries of the stiffer radially inner portion of the haptic, is about 40 degrees. The stiff radially inner portion of haptic 14 is positioned directly adjacent the periphery of the optic. The dimensions and angles provided are not intended to be strictly limiting.

Figure 5A:
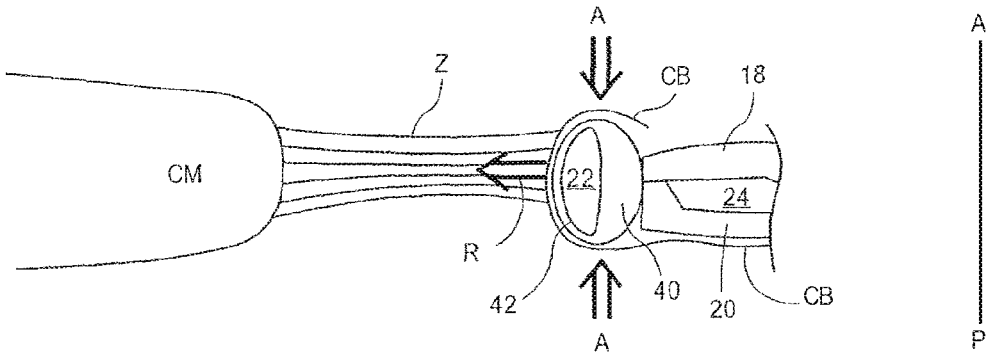
FIGS. 5A and 5B illustrate the deformation of an exemplary haptic in response to exemplary forces.
Figure 5B:
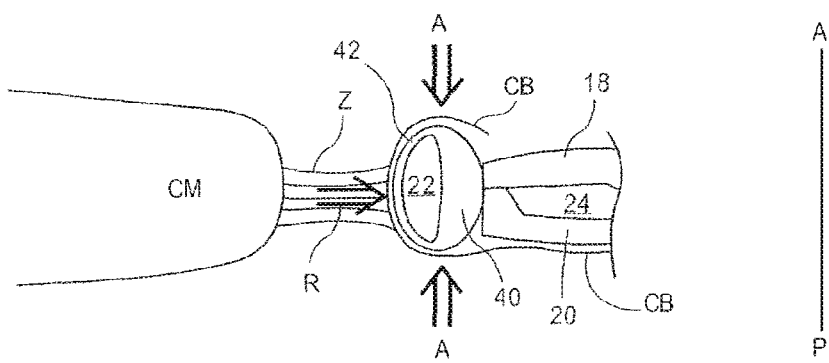

FIGS. 5A and 5B illustrate a portion of accommodating intraocular lens 10 positioned in a capsular bag ("CB") after a native lens has been removed from the CB. The anterior direction is on top and the posterior direction is on bottom in each figure. FIG. 5A shows the accommodating intraocular lens in a lower power, or dis-accommodated, configuration relative to the high power, or accommodated, configuration shown in FIG. 5B.

The elastic capsular bag "CB" is connected to zonules "Z," which are connected to ciliary muscles "CM." When the ciliary muscles relax, as shown in FIG. 5A, the zonules are stretched. This stretching pulls the capsular bag in the generally radially outward direction due to radially outward forces "R" due to the general equatorial connection location between the capsular bag and the zonules. The zonular stretching causes a general elongation and thinning of the capsular bag. When the native lens is still present in the capsular bag, the native lens becomes flatter (in the anterior-to-posterior direction) and taller in the radial direction, which gives the lens less power. Relaxation of the ciliary muscle, as shown in FIG. 5A, provides for distance vision. When the ciliary muscles contract, however, as occurs when the eye is attempting to focus on near objects, the radially inner portion of the muscles move radially inward, causing the zonules to slacken. This is illustrated in FIG. 5B. The slack in the zonules allows the capsular bag to move towards a generally more curved configuration in which the anterior surface has greater curvature than in the dis accommodated configuration, providing higher power and allowing the eye to focus on near objects. This is generally referred to as "accommodation," and the lens is said to be in an "accommodated" configuration.

In section A-A (which is the same as section B-B) of haptic 14, illustrated in FIGS. 5A and 5B, radially inner portion 40 includes thicker bulk material that provides haptic 14 with stiffness in the anterior-to-posterior direction. When capsular bag forces are applied to the haptic in the anterior-to-posterior direction, the inner portion 40, due to its stiffness, deforms in a more repeatable and predictable manner making the base state of the lens more predictable.

Additionally, the haptic, due to its stiffer inner portion, deforms the capsule in a repeatable way in the anterior-to-posterior direction. Additionally, because the haptic is less flexible along the length of the haptic, the accommodating intraocular lens's base state is more predictable because bending along the length of the haptic is one way in which fluid can be moved into the optic (and thereby changing the power of the lens). Additional advantages realized with the stiffer inner portion are that the haptics are stiffer to other forces such as torqueing and splaying because of the extra bulk in the inner portion.

The radially outer portion 42 is the portion of the haptic that directly engages the portion of the capsular bag that is connected to the zonules. Outer portion 42 of the haptics is adapted to respond to capsular reshaping forces "R" that are applied generally radially when the zonules relax and stretch. This allows the haptic to deform in response to ciliary muscle related forces (i.e., capsular contraction and relaxation) so that fluid will flow between the haptic and the optic in response to ciliary muscle relaxation and contraction. This is illustrated in FIG. 5B. When the ciliary muscles contract (FIG. 5B), the peripheral region of the elastic capsular bag reshapes and applies radially inward forces "R" on radially outer portion 42 of haptic 14. The radially outer portion 42 is adapted to deform in response to this capsular reshaping. The deformation decreases the volume of fluid channel 22, which forces fluid from haptic chamber 22 into optic chamber 24. This increases the fluid pressure in optic chamber 42. The increase in fluid pressure causes flexible anterior element 18 and flexible posterior element 20 to deform, increasing in curvature, and thus increasing the power of the intraocular lens.

The haptic is adapted to be stiffer in the anterior-to-posterior direction than in the radial direction. In this embodiment the radially outer portion 42 of haptic 14 is more flexible (i.e., less stiff) in the radial direction than the stiffer inner portion 40 is in the anterior-to-posterior direction. This is due to the relative thicknesses of outer portion 42 and inner portion 40. The haptic is thus adapted to deform less in response to forces in the anterior-to-posterior direction than to forces in the radial direction. This also causes less fluid to be moved from the haptic into the optic in response to forces in the anterior-to-posterior direction than is moved into the optic in response to forces in the radial direction. The haptic will also deform in a more predictable and repeatable manner due to its stiffer radially inner portion.

The peripheral portion is thus more sensitive to capsular bag reshaping in the radial direction than to capsular bag reshaping in the anterior-to-posterior direction. The haptics are adapted to deform to a greater extent radially than they are in the anterior-to-posterior direction. The disclosure herein therefore includes a peripheral portion that is less sensitive to capsular forces along a first axis, but is more sensitive to forces along a second axis. In the example above, the peripheral portion is less sensitive along the posterior-to-anterior axis, and is more sensitive in the radial axis.

An exemplary benefit of the peripheral portions described above is that they deform the capsular bag in a repeatable way and yet maintain a high degree of sensitivity to radial forces during accommodation. The peripheral portions described above are stiffer in the anterior-to-posterior direction than in the radial direction.

An additional example of capsular forces in the anterior-to-posterior direction is capsular forces on the peripheral portion after the accommodating intraocular lens is positioned in the capsular bag, and after the capsular bag generally undergoes a healing response. The healing response generally causes contraction forces on the haptic in the anterior-to-posterior direction, identified in FIG. 5A by forces "A." These and other post-implant, such as non-accommodating-related, capsular bag reshaping forces are described in U.S. application Ser. No. 12/685,531, filed Jan. 11, 2010, which is incorporated herein by reference. For example, there is some patient to patient variation in capsular bag size, as is also described in detail in U.S. application Ser. No. 12/685,531, filed Jan. 11, 2010. When an intraocular lens is positioned within a capsular bag, size differences between the capsule and intraocular lens may cause forces to be exerted on one or more portions of the intraocular lens in the anterior-to-posterior direction.

In the example of capsular healing forces in the anterior-to-posterior direction, the forces may be able to deform a deformable haptic before any accommodation occurs. This deformation changes the volume of the haptic fluid chamber, causing fluid to flow between the optic fluid chamber and the haptic fluid chambers. This can, in some instances undesirably, shift the base power of the lens. For example, fluid can be forced into the optic upon capsular healing, increasing the power of the accommodating intraocular lens, and creating a permanent myopic shift for the accommodating intraocular lens. Fluid could also be forced out of the optic and into the haptics, decreasing the power of the accommodating intraocular lens.

As used herein, "radial" need not be limited to exactly orthogonal to the anterior-to-posterior plane, but includes planes that are 45 degrees from the anterior-to-posterior plane.

Exemplary fluids are described in U.S. application Ser. No. 12/685,531, filed Jan. 11, 2010, and in U.S. application Ser. No. 13/033,474, filed Feb. 23, 2011, both of which are incorporated herein by reference. For example, the fluid can be a silicone oil that is or is not index-matched with the polymeric materials of the anterior and posterior elements. When using a fluid that is index matched with the bulk material of the optic portion, the entire optic portion acts a single lens whose outer curvature changes with increases and decreases in fluid pressure in the optic portion.

In the embodiment in FIGS. 2A-2G above the haptic is a deformable polymeric material that has a substantially uniform composition in Sections A-A, B-B, and C-C. The stiffer radially inner body portion 40 is attributed to its thickness. In alternative embodiments the radially inner body portion has a different composition that the outer body portion, wherein the radially inner body portion material is stiffer than the material of the radially outer body portion. In these alternative embodiments the thicknesses of the radially inner and outer portions can be the same.

Figure 6:
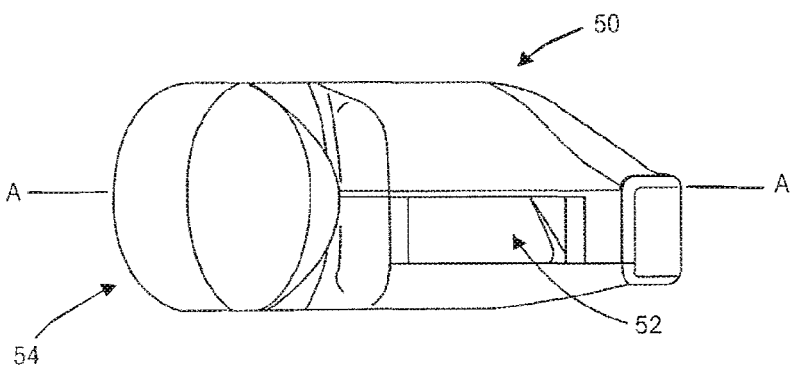
FIG. 6 illustrates an exemplary fluid opening in an exemplary haptic.

FIG. 6 illustrates haptic 50, which is the same haptic configuration as in shown in FIG. 2B. The radially outer portion 54 is identified. The haptic has axis "A" halfway through the height of the haptic, or alternatively stated, axis A passes through the midpoint of the height of the haptic in the anterior-to-posterior direction. Opening 52, in which the optic buttress is disposed, is on the posterior side of axis A. In this embodiment the optic sits slightly closer to the posterior-most portion of the haptics than the anterior-most portion of the haptics. That is, in this embodiment the optic is not centered with the haptics in the anterior-to-posterior direction.

Figure 7:
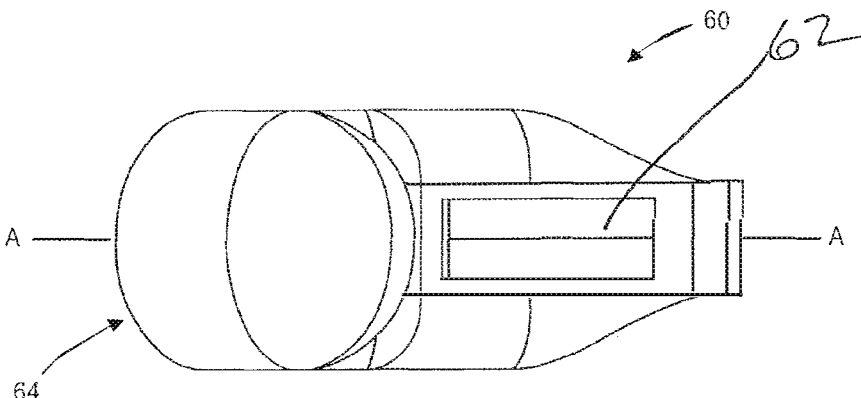
FIG. 7 illustrates an exemplary fluid opening in an exemplary haptic.
Figure 8:
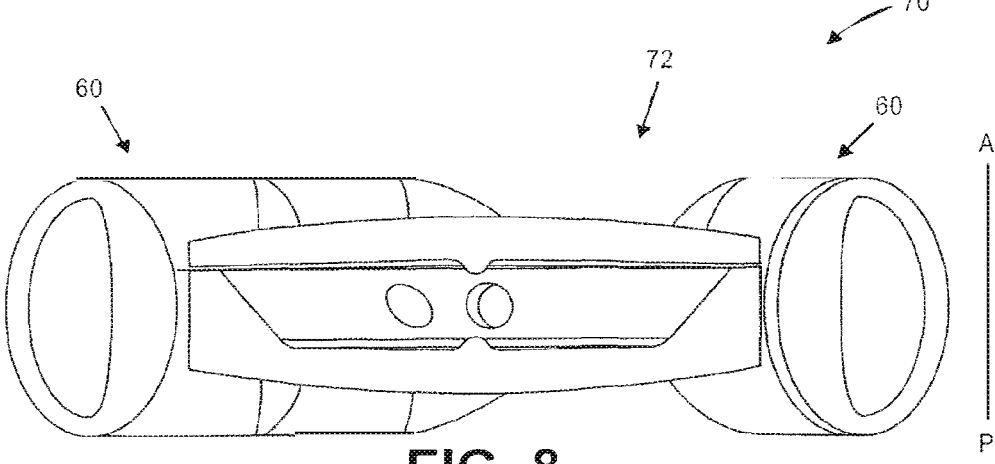
FIG. 8 illustrates a sectional view of an exemplary accommodating intraocular lens.

FIG. 7 illustrates an alternative haptic 60 (optic not shown), wherein the radially outer portion 64 is identified. Haptic 60 includes axis "A" halfway through the thickness of the haptic, or alternatively stated, axis A passes through the midpoint of the height of the haptic in the anterior-to-posterior direction. Opening 62 is symmetrical about the axis A, and an axis passing through the midpoint of opening 62 is aligned with axis A. Additionally, axis A is an axis of symmetry for haptic 60. The symmetry of the haptic along axis A can improve the ability to mold low relatively low stress components. FIG. 8 shows an embodiment of intraocular lens 70 in which the optic 72 is coupled to two haptics 60, which are the haptics shown in FIG. 7. The optic sits further in the anterior direction that in the embodiment in which the opening is not along the midline of the haptic. In this embodiment, optic 72 is centered, in the anterior-to-posterior direction, with the haptics. The cross sections A-A, B-B, and C-C of haptic 60 are the same as those shown in other embodiments shown above, but the haptics can have any alternative configuration as well.

Figure 9:
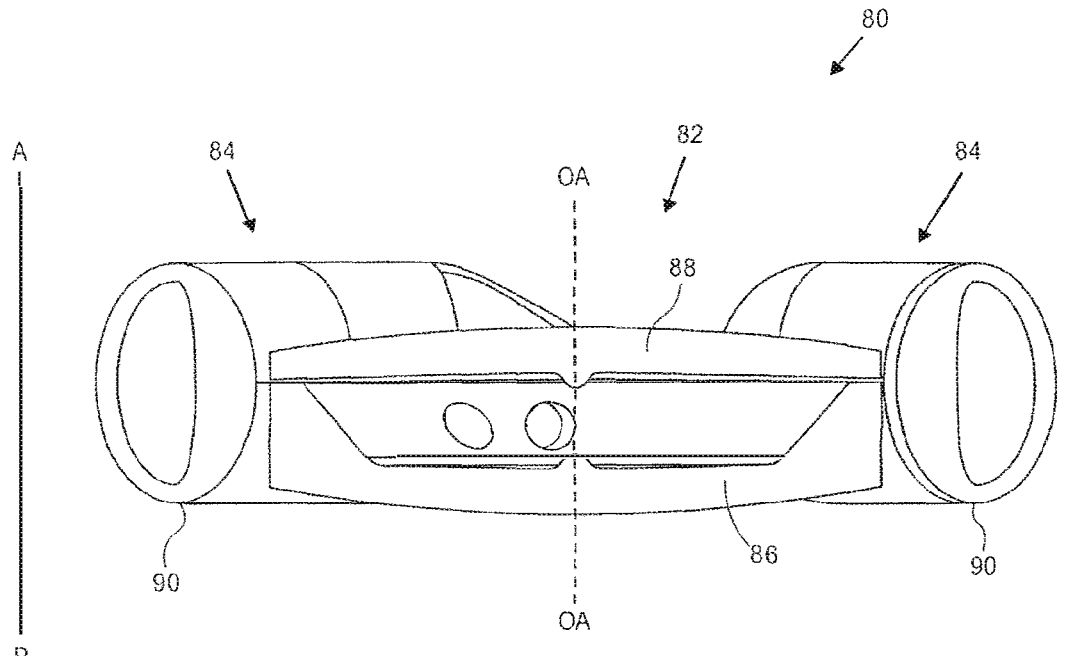
FIG. 9 illustrates a sectional view of an exemplary accommodating intraocular lens with relatively short haptics.

FIG. 9 illustrates intraocular lens 80 including optic 82 and two haptics 84. The optic is the same as the optic portions described herein. Haptics 84 are not as tall, measured in the anterior-to-posterior direction, as haptic 60, haptic 50, or haptic 14. In exemplary embodiments haptics 84 are between about 2.0 mm and about 3.5 mm tall, and in some embodiments they are about 2.8 mm tall. Intraocular lens 80 can be considered a size "small" accommodating intraocular lens for patients with a capsular bag that is below a certain threshold size. The posterior surface of posterior element 86 is disposed slightly further in the posterior direction than the posterior-most portions 90 of haptics 84.

Figure 10:
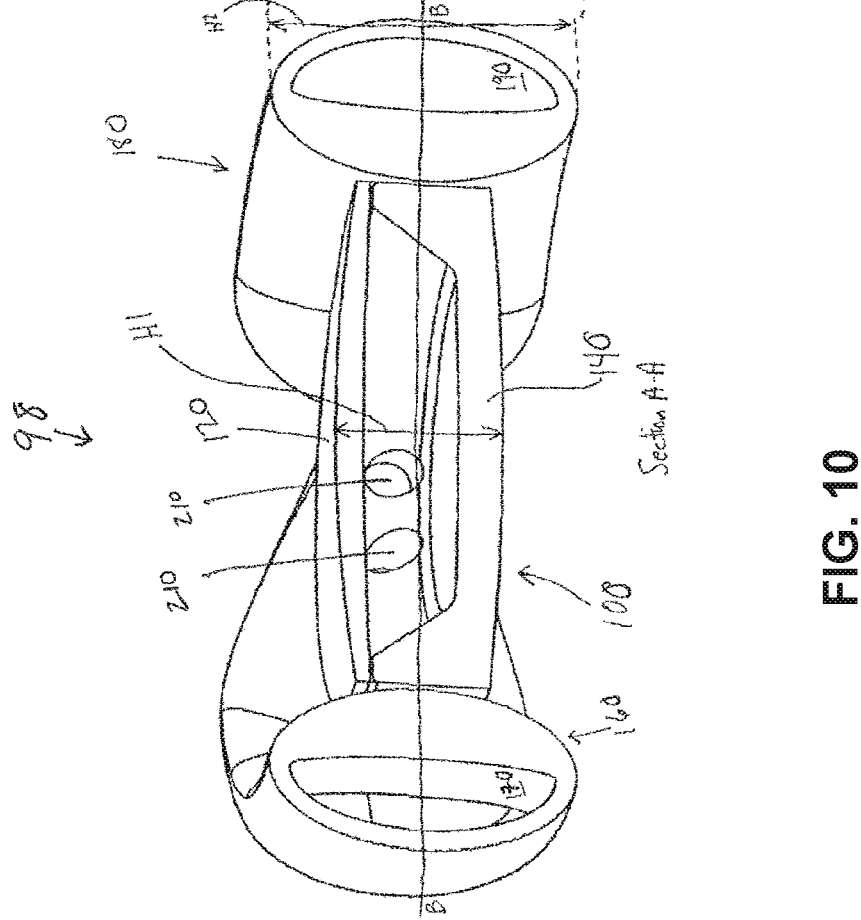
FIG. 10 illustrate a sectional view of an exemplary accommodating intraocular lens with an optic centered with a peripheral portion.

FIG. 10 illustrates an accommodating intraocular lens 98 that includes an optic body 100 and a peripheral non-optic body, which in this embodiment includes haptics 160 and 180. Optic body 100 can be in fluid communication with one or both haptics 160 and 180, and fluid movement between the optic and haptics in response to ciliary muscle movement can change the power of the intraocular lens. This general process of fluid-driven accommodation in response to deformation of the haptics can be found herein. Optic 100 includes anterior element 120 secured to posterior element 140, together defining an optic fluid chamber in communication with haptic fluid chambers 170 and 190 in the haptics. The "height" of the components in this disclosure is measured in the anterior-to-posterior direction. Optic 100 has a greatest height "H1" dimension measured in the anterior to posterior direction along the optic axis. Haptics 160 and 180 have greatest height "H2" dimensions measured in the anterior to posterior direction parallel to the optical axis. The optic body has a centerline B, measured perpendicular to the optical axis and passing through the midpoint of H1. The haptics also have centerlines, B, measured perpendicular to the optical axis and passing through the midpoint of H2. In this embodiment the centerlines coincide and are the same centerline B. Stated alternatively, the anterior-most surface or point of anterior element 120 is spaced from the anterior-most point or surface of the haptics the same distance as is the posterior-most surface or point of posterior element 140 from the posterior-most point or surface of the haptics. They can be considered substantially the same lines in some embodiments even if they do not coincide, but are near in space to one another (e.g., a few millimeters away). An optic centered with the haptics is also shown in FIG. 8.

In this embodiment the position of the optic 100 relative to the haptics can provide some benefits. For example, during folding and/or insertion, the centered (or substantially centered) optic, measured in the anterior-to-posterior direction, can prevent or reduce the likelihood of one or more haptics from folding over the anterior element 120 or posterior element 140, which may happen when the optic body is not substantially centered relative to the haptics. For example, an optic that is much closer to the posterior side of the lens may increase the likelihood that a haptic (e.g., a haptic free end) can fold over the anterior surface of the optic during deformation, loading, or implantation.

An additional benefit to having the optic body 100 centered or substantially centered relative to the peripheral body is that is it easier for the optic to pass through the capsulorhexis when placed in the eye. When the optic is closer to the posterior side of the lens, it may be more difficult for it to rotate into the capsular bag.

An additional benefit is that, compared to optics that are further in the posterior direction, glare from the intraocular lens is reduced. By moving the optic in the anterior direction (it will be closer to the iris once implanted), less light can reflect off of the radially outer peripheral edge of the optic (i.e., the edge surface adjacent the haptics), thus reducing glare from edge effect.

In some embodiments of the intraocular lens in FIG. 10, anterior element 120 can have a height between 0.2 mm and 0.35 mm, such as between 0.25 mm and 0.30 mm, such as about 0.28 mm, and the posterior element 140 can have a height between 0.36 mm and 0.50 mm, such as between 0.40 mm and 0.45 mm, such as about 0.43 mm.

Prior to insertion, such as during manufacturing, the intraocular lens shown in FIG. 10 can be filled with fluid. In some embodiments the intraocular lens has a base state (at zero fluid pressure in the optic; or no fluid inside it) less than 15 D, such as about 13 D. About 13 D, as used herein, refers to base states about 10 D to about 15 D. By having a base state of about 13 D, it may be possible to generally only have to change the fluid pressure in one direction—higher. When the base state of an intraocular lens is higher, such as about 20 D, it may be necessary to change the fluid pressure either higher or lower, depending on the desired vision correction and the intended use of the intraocular lens. By having a lower base state, the changes to the state of the lens become more predictable by only having to change the base state in one direction.

One aspect of this disclosure is an accommodating intraocular lens, optionally fluid-filled and fluid-driven, that has an aspheric optical surface after manufacture and prior to implantation. That is, the intraocular lens is manufactured with an aspheric optical surface. An aspheric optical surface can avoid spherical aberration when the pupil is fully dilated. There can be challenges in manufacturing an intraocular lens, particularly an accommodating, fluid-driven intraocular lens, with aspheric optical surfaces.

In some embodiments the accommodating intraocular lens is manufactured with an aspheric anterior surface and/or an aspheric posterior surface. One exemplary manner in which a fluid-filled accommodating intraocular lens can have an anterior or posterior optical surface with built-in asphericity is to, during manufacturing, create the optical surface with a spherical configuration prior to fluid filling, then create the asphericity in the optical surface during the fill process. For example, during manufacture, one or both of the anterior surface and the posterior surface can be manufactured to have spherical outer optical surfaces. The anterior surface can then be secured to the posterior surface. One or more haptics can then be secured to the optic. In some embodiments the optic is manufactured, but prior to filling, to have a base state (at zero fluid pressure in the optic; or no fluid inside it) less than 15 D, such as about 13 D. About 13 D, as used herein, refers to base states about 10 D to about 15 D. When a fluid is injected into the accommodating intraocular lens (e.g., via a septum), the fluid filling step can increase the fluid pressure in the optic and cause the anterior surface and/or the posterior surface of the optic to have an aspherical configuration. One aspect of this disclosure is thus a method of manufacturing an accommodating intraocular lens that includes creating an optic with a fluid-filled state prior to insertion, which has asphericity built into one or more optical surfaces, such as an anterior optic surface. The method of manufacturing can include manufacturing the optic wherein the optical surface is spherical prior to fluid filling.

It may be desirable to maintain good optical quality in at least one surface of the central portion of the optic as it is deformed, either throughout disaccommodation or through-out accommodation. One of the aspects of the disclosure is an optic that has a very controlled and somewhat stable amount of asphericity in a central region of the optic, across the whole range of powers. This may be referred to herein as "beneficial asphericity" in a central region of the optic. The beneficial asphericity includes lens surfaces with surface aberrations that are configured to compensate for the spherical aberrations in the optical system of the eye, and contribute to maintaining optical quality. The beneficial asphericity is maintained across all or substantially all of the range of powers during accommodation and disaccommodation. In some instances the asphericity can be controlled such that the spherical aberration of the whole lens systems can remain low (or zero) across all range of power. The optic region outside of the central region may have larger, more uncontrolled amount of asphericity.

In some embodiments the central region of the optic, or the region of beneficial asphericity, has a diameter of less than 6.5 mm, less than 6.0 mm, less than 5.5 mm, less than 5.0 mm, less than 4.5 mm, less than 4.0 mm, less than 3.5 mm, or even less than 3.0 mm. In some embodiments the central region has a diameter between 3.5 mm and 5.5 mm. In some embodiments the central region of the optic with beneficial asphericity has a diameter less than 90% of the diameter of the optic body, less than 85%, less than 80%, or less than 75%. The diameter of the optic can be between 4 mm and 8 mm, such as between 5 mm and 7 mm. In some embodiments the central region is between 4 mm and 5 mm, and the optic diameter is between 5 mm and 7 mm. In some embodiments the central region is between 4.25 mm and 4.75 mm, and the optic diameter is between 5.75 mm and 6.25 mm.

The configuration of the anterior element and the posterior element can influence the configurations that they assume throughout deformation, either throughout accommodation or disaccommodation. In some embodiments, one or both of the anterior element and the posterior element is contoured, or configured, such that the central region of the optic has the beneficial asphericity that is controlled and beneficial to the overall system of the eye. In this embodiment anterior element 120, and to a lesser extent posterior element 140, are configured so that an anterior surface of anterior element 120 and a posterior surface of posterior element 140 maintain the controlled, beneficial asphericity in a central region of the optic during accommodation. In this embodiment one aspect of the configuration that contributes to the central portion maintaining beneficial asphericity is that anterior element 120, and optionally the posterior element 140, has a thickness (also referred to as "height" herein) that is greater in the center (such as at the apex of the anterior element 120) than at the periphery of the anterior element 120. An additional aspect of the configuration that contributes to beneficial asphericity is that the anterior element is flatter on the inner surface (posterior surface) than on the outer surface (anterior surface). During accommodation, the central region of the anterior element 120 steepens in the center (which increases power of the AIOL), but the optic body maintains its beneficial aspheric-ity, due at least in part to the relatively larger thickness of the anterior element central region. It may also be aspherical prior to accommodating in the exemplary embodiments in which asphericity is built into the anterior element, described below.

The thickness contours of the anterior and posterior elements can contribute to the optic maintaining the benefi-cial asphericity across all powers, an example of which is the thickness of the anterior and posterior elements.

Figure 11:
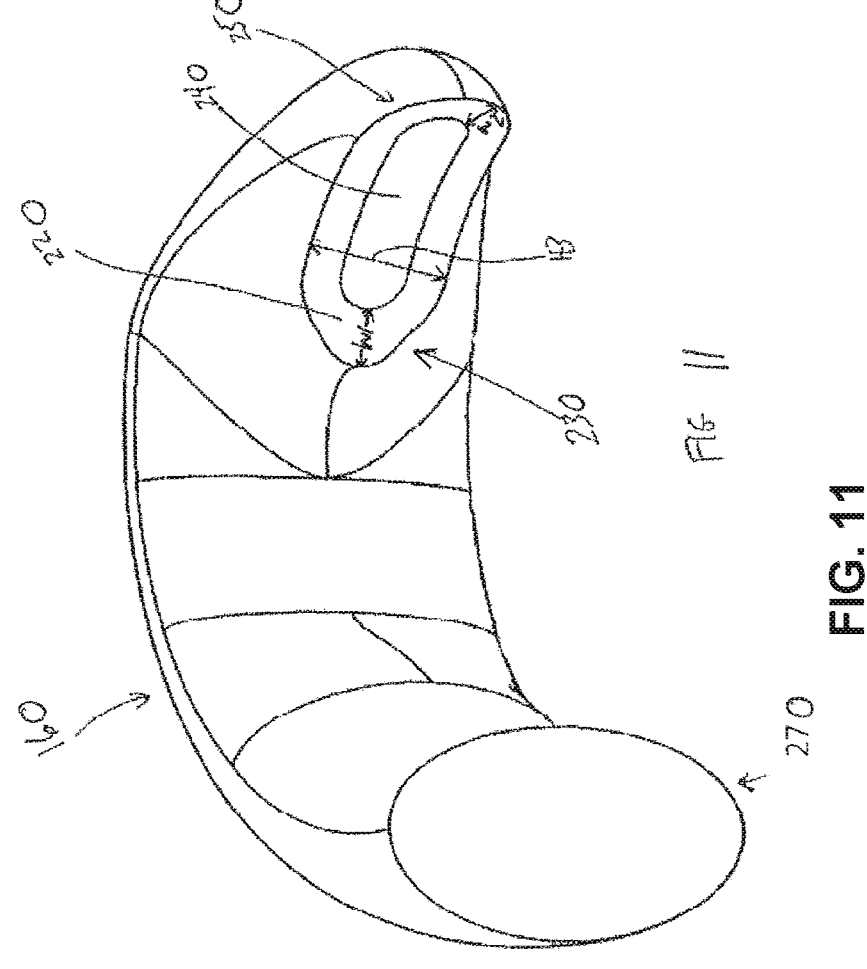
FIG. 11 is an exemplary haptic.

FIG. 11 illustrates an exemplary haptic that can be part of any of the accommodating intraocular lenses herein or other suitable IOLs not described herein. One or both haptics can be configured as shown in FIG. 11. The haptic in FIG. 11 is labeled as "160," but it is understood that the haptic in FIG. 11 can be a part of intraocular lenses other than that shown in FIG. 10. The haptic includes a surface 220 that is secured to an outer edge of the optic body. Surface 220 is a radially inner surface of the haptic, and is configured with a slight curve to it (along the length of the haptic) that is substan-tially the same curve as the outer edge of the optic so that the entire surface 220 interfaces the optic body outer edge surface(s). Surface 220 has a configuration relative to the optic such that an extension of the surface does not pass through an optic axis of the optic. An adhesive can be used to secure surface 220 to the optic outer edge surface(s). In this embodiment the coupling between the haptic and the optic body does not include one of the haptic and optic being disposed within a channel, bore, or aperture in the other, as can be used for some haptic/optic coupling designs, such as in the embodiment shown in FIGS. 1A-9. Some exemplary advantages of this type of design are described below.

Figure 12:
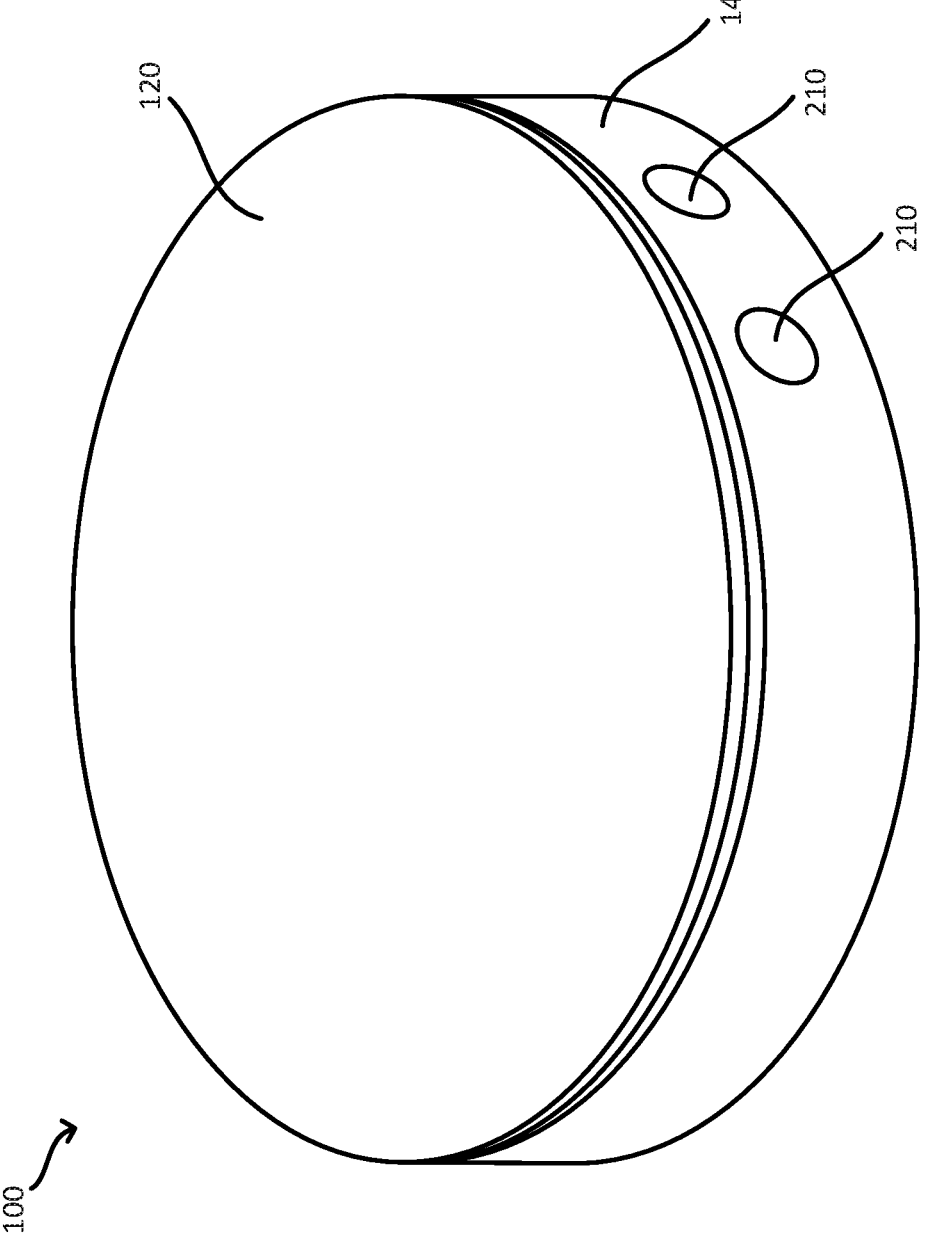
FIG. 12 shows an exemplary optic portion.

FIG. 12 shows a perspective view of optic 100, with the haptics excluded for clarity. Surface 220 of the haptic (not shown) is secured to both anterior element 120 and posterior element 140 of the optic body 100. Most of surface 220 interfaces posterior portion 140, but a portion of surface 220 interfaces anterior element 120. This is because the outer edge of the optic body is largely comprised of the posterior element 140. With different optic configurations, surface 220 could be secured to more of the anterior element than the posterior element. It is also noted that the height H3 of surface 220 (see FIG. 11) is substantially the same as the height of the outer edge of the optic body.

Figure 13:
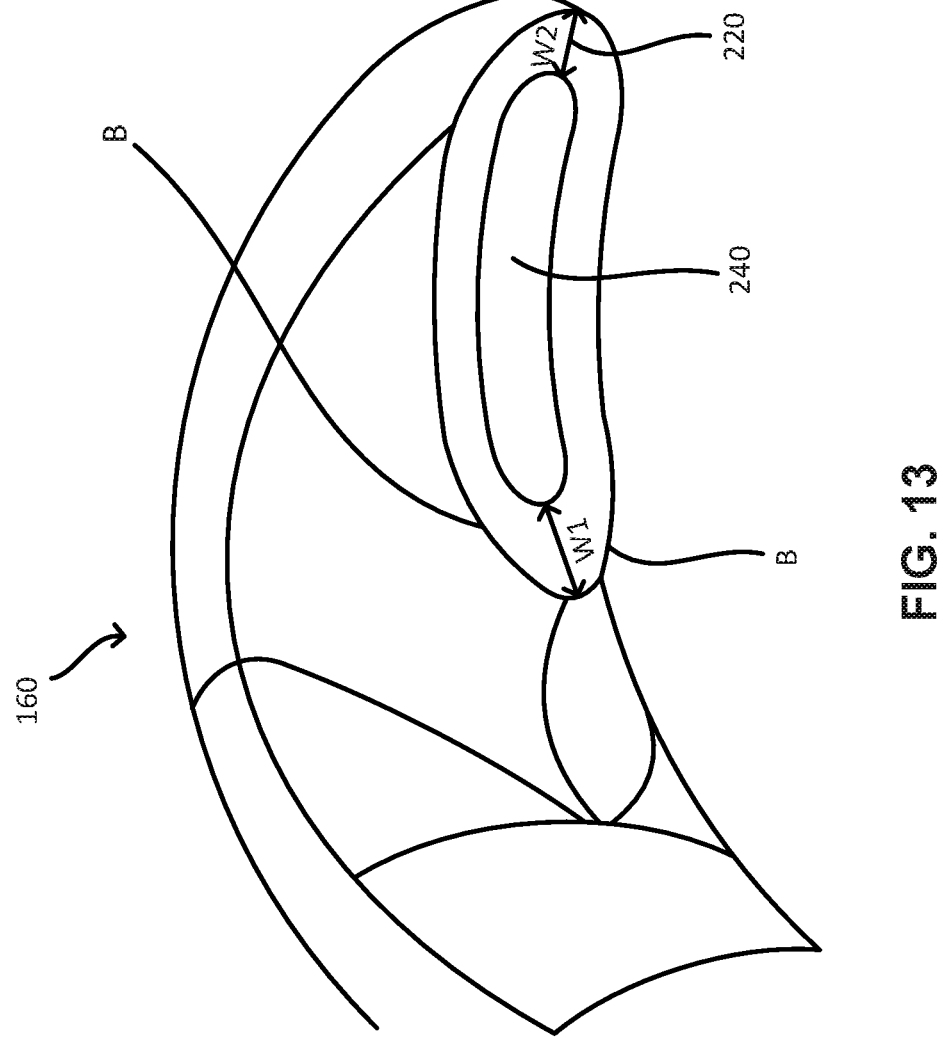
FIG. 13 shows a portion of an exemplary haptic.

Haptic 160 surface 220 has a first end region 230 (see FIG. 11) that has a configuration with a larger surface than second end region 250. End region 230 of surface 220 has a larger surface area than end region 250 of surface 220, and includes at least partially beveled surfaces B, as shown in FIG. 13. The width W1 of end region 230 is greater than width W2 of end region 250. The configuration of end region 230 can provide exemplary benefits. For example, as part of a process of loading the intraocular lens into a delivery device and/or into an eye of a patient, one or both of haptics 160 and 180 may be "splayed" relative to optic. That is, one or both haptics can be reconfigured from the natural at rest configuration shown in FIGS. 10-14 by moving free end 170 of haptic away from the optic body. The extent to which the free end (and a large portion of the haptic) is moved away from the optic during splaying can vary. In some methods of loading, one or both haptics can be splayed substantially, such that the haptic is oriented behind or in front of the optic. In some instances the haptic free end (i.e., the end of the haptic not coupled directly to the optic) is "pointing" sub-stantially 180 degrees from where it is pointing in the at-rest configuration. In general, splaying the haptic(s) causes stresses at the coupling interface between the haptic and optic. The coupling interface between the optic and haptic must be able to withstand these forces so that the haptic does not disengage from the optic. When splaying haptics, there can be a high stress location at the optic/haptic coupling at the end of the interface 230, which is closer to the free end. End region 230 is thus the location where the haptic/optic interface is most likely to fail. End region 230, with its larger surface area and tapering and beveled configuration, acts to distribute the applying stresses (or stresses anytime haptic is reoriented relative to the optic) and prevent the haptic from disengaging from the optic.

The configuration of surface 220 can be modified in many ways to provide the desired joinery between the haptic and the optic. Joining the haptic and the optic in this manner (as opposed to having one component fit within the other) thus allows for many more interface configurations, which pro-vides more flexibility in design.

In the embodiment of the haptic in FIG. 11, fluid aperture 240 is centered along the midline of the haptic. The center-line is defined in the same manner as described in FIG. 10. The centerline passes through the midpoint of the haptic height (measured in an anterior-to-posterior direction) in a side view of the haptic.

Other aspects of the haptic can be the same as described herein, such as a thicker radially inner wall thickness along a portion of the haptic, and one or both haptics that follows the curvature of the periphery of the optic from the coupled end to the free end, and the anterior most aspect of the haptic extending further anteriorly than the anterior-most aspect of the optic.

The posterior element 140 has two fluid channels 210 therein that are in fluid communication with the haptic fluid chambers 170 and 190. The outer edge of the posterior element 140 includes two apertures therein that define ends of the fluid channels 210. The haptic/optic interface (which can be a glue joint) surrounds the two fluid apertures in the posterior element 140. In some alternatives the optic only has one fluid channel instead of two.

FIG. 13 is another view of haptic 160, showing the slight curvature of optic interface surface 220 and fluid aperture 240 therein.

Figure 14:
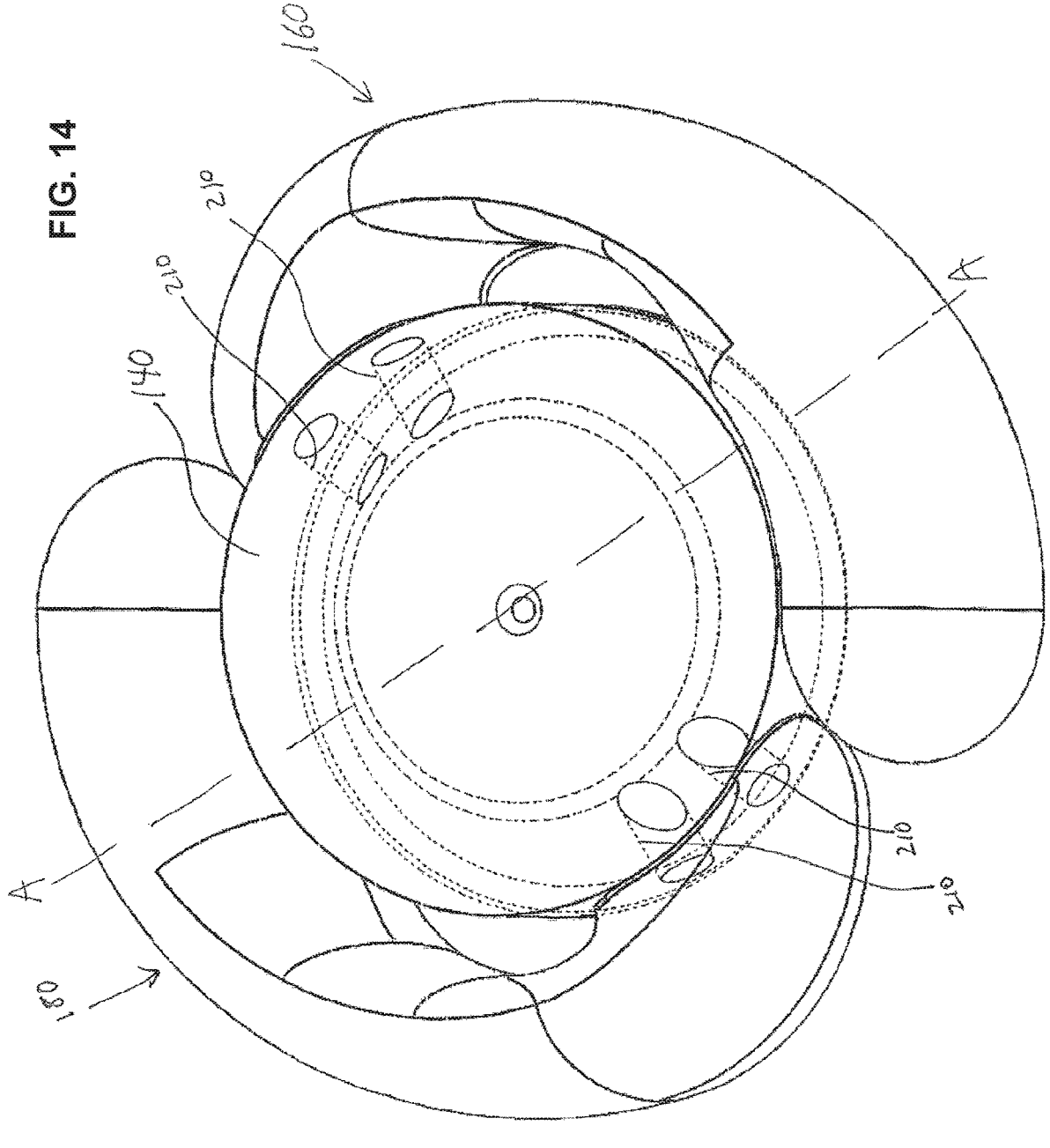
FIG. 14 shows an exemplary IOL.

FIG. 14 is a perspective view of the intraocular lens from FIG. 10, viewed from the posterior side. Fluid channels 210 can be seen in the posterior element 140, two of which are associated with each haptic. The interface between the haptics and optic can also be seen. FIG. 14 shows section A-A that is shown in FIG. 10.

Figure 15:
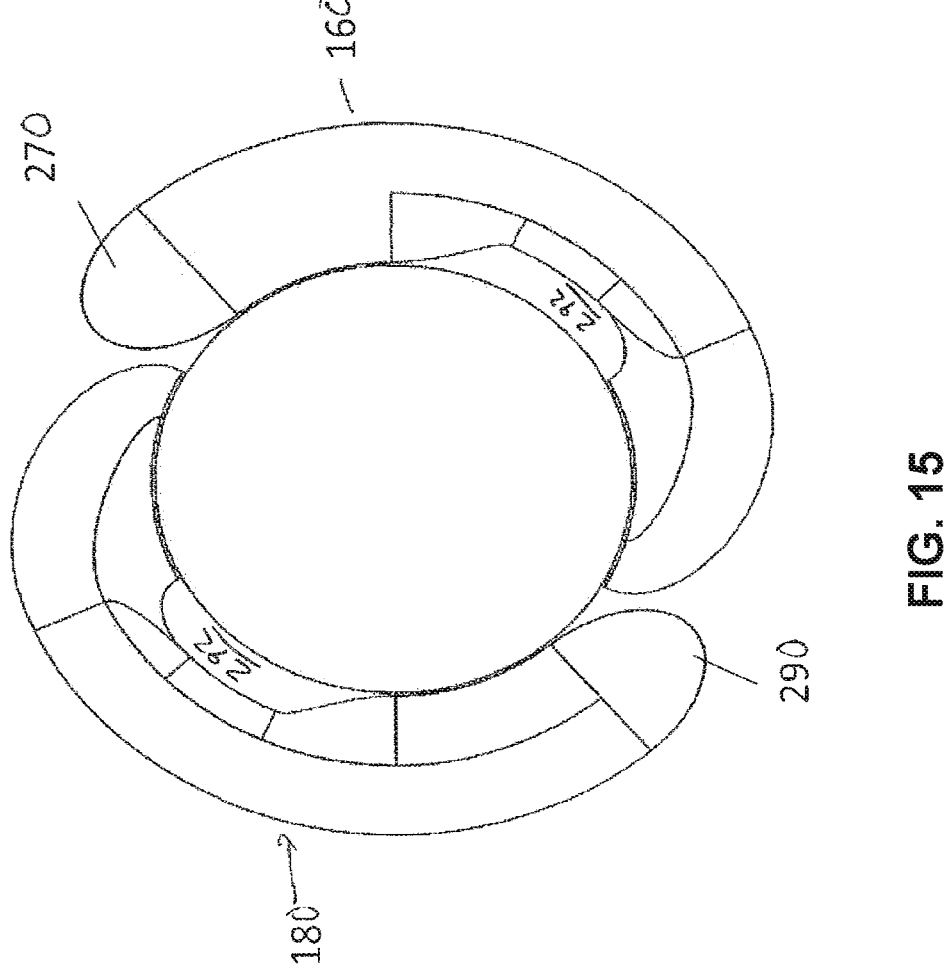
FIG. 15 shows an exemplary IOL.

FIG. 15 shows an additional view of the intraocular lens from FIG. 10, in which spacings 292 between the outer edge of optic and haptics can be seen, as well as the coupling between the optic and haptics.

Figure 16:
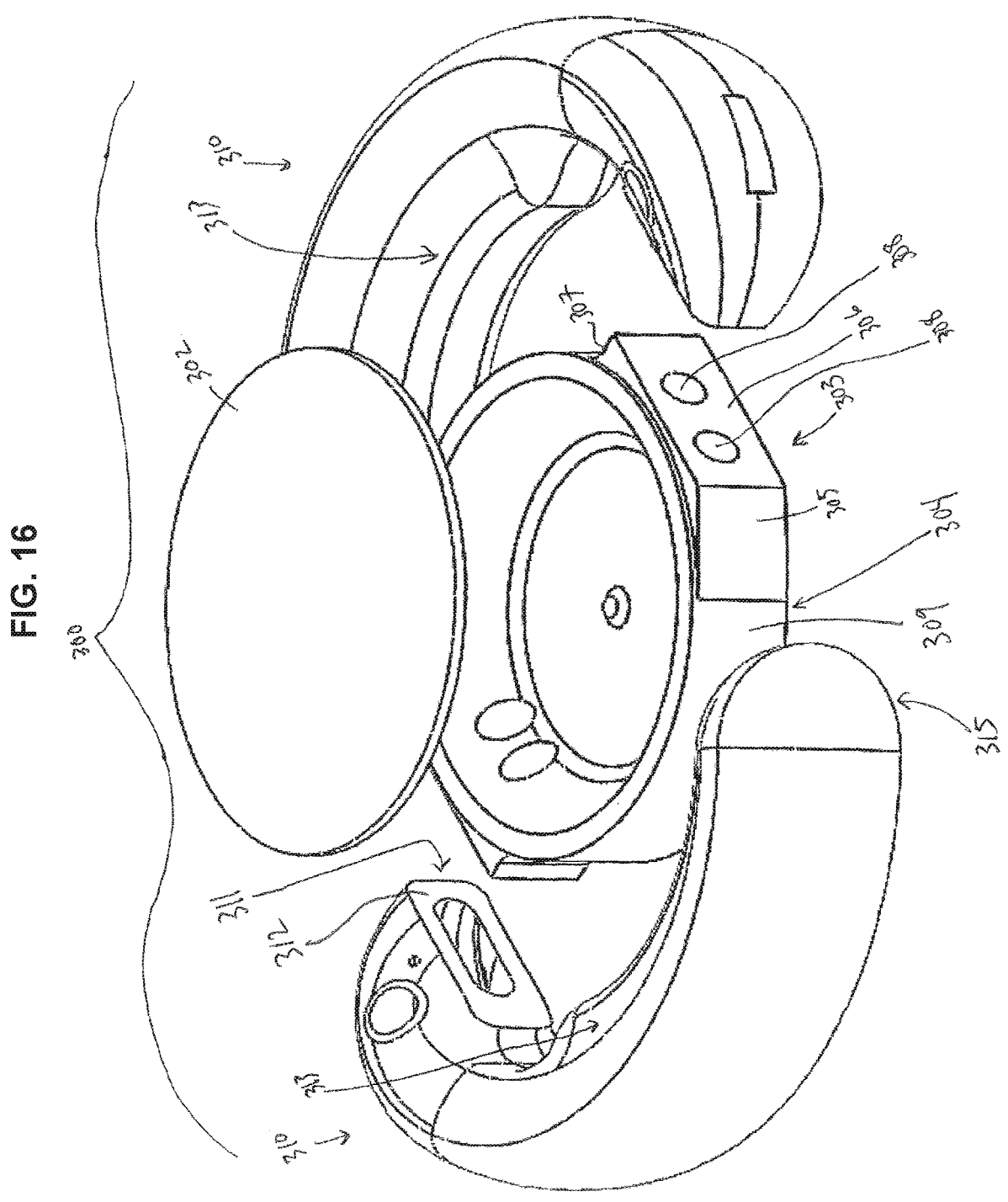
FIG. 16 shows an exemplary IOL.
Figure 17:
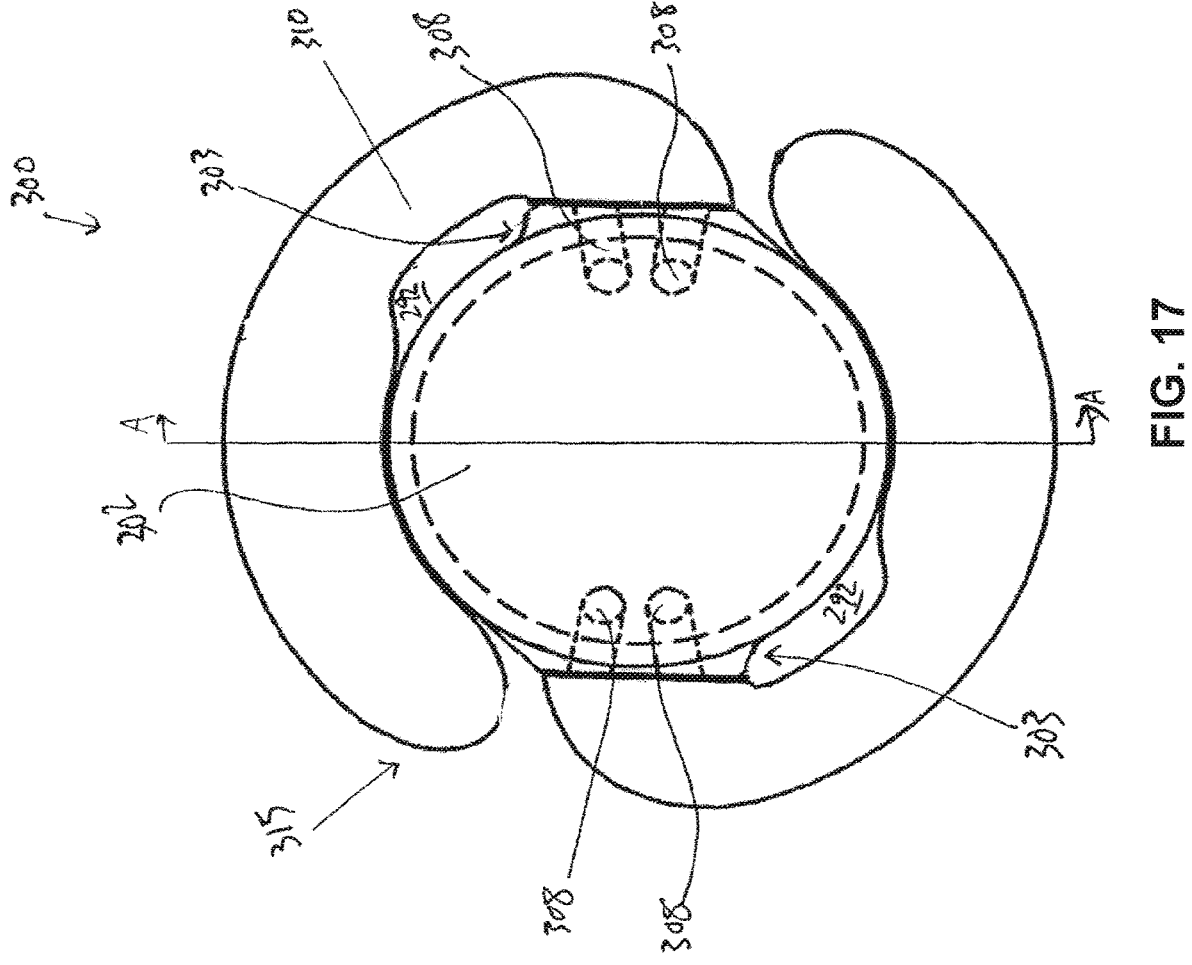
FIG. 17 shows a top view of an exemplary IOL.

In some embodiments in which one or more haptics are adhered to the optic body at discrete locations, rather than 180 degrees around the optic, a curing step that cures an adhesive that secures the haptic to the optic body may cause shrinkage of the material at the location where the two components are adhered. This shrinkage at the discrete locations can cause distortions in the lens, such as astigma-tism. It can be beneficial, or necessary, to prevent or reduce the extent of the distortions. FIG. 16 illustrates an exploded perspective view of alternative accommodating intraocular lens 300. FIG. 17 illustrates a top view of AIOL 300. FIG.

Figure 19:
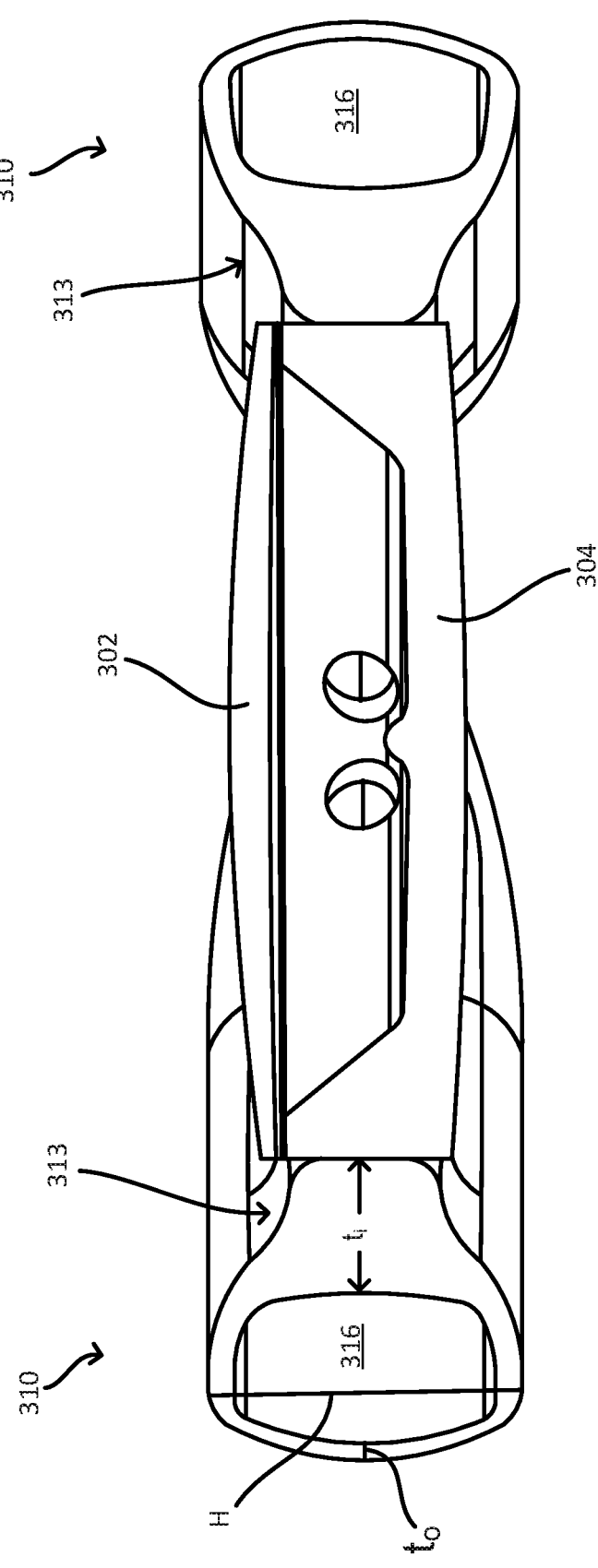
FIG. 19 shows a sectional view of an exemplary IOL.

18 illustrates a perspective view of option 301 of AIOL 300. FIG. 19 is a view of section A-A shown in FIGS. 17.

Figure 18:
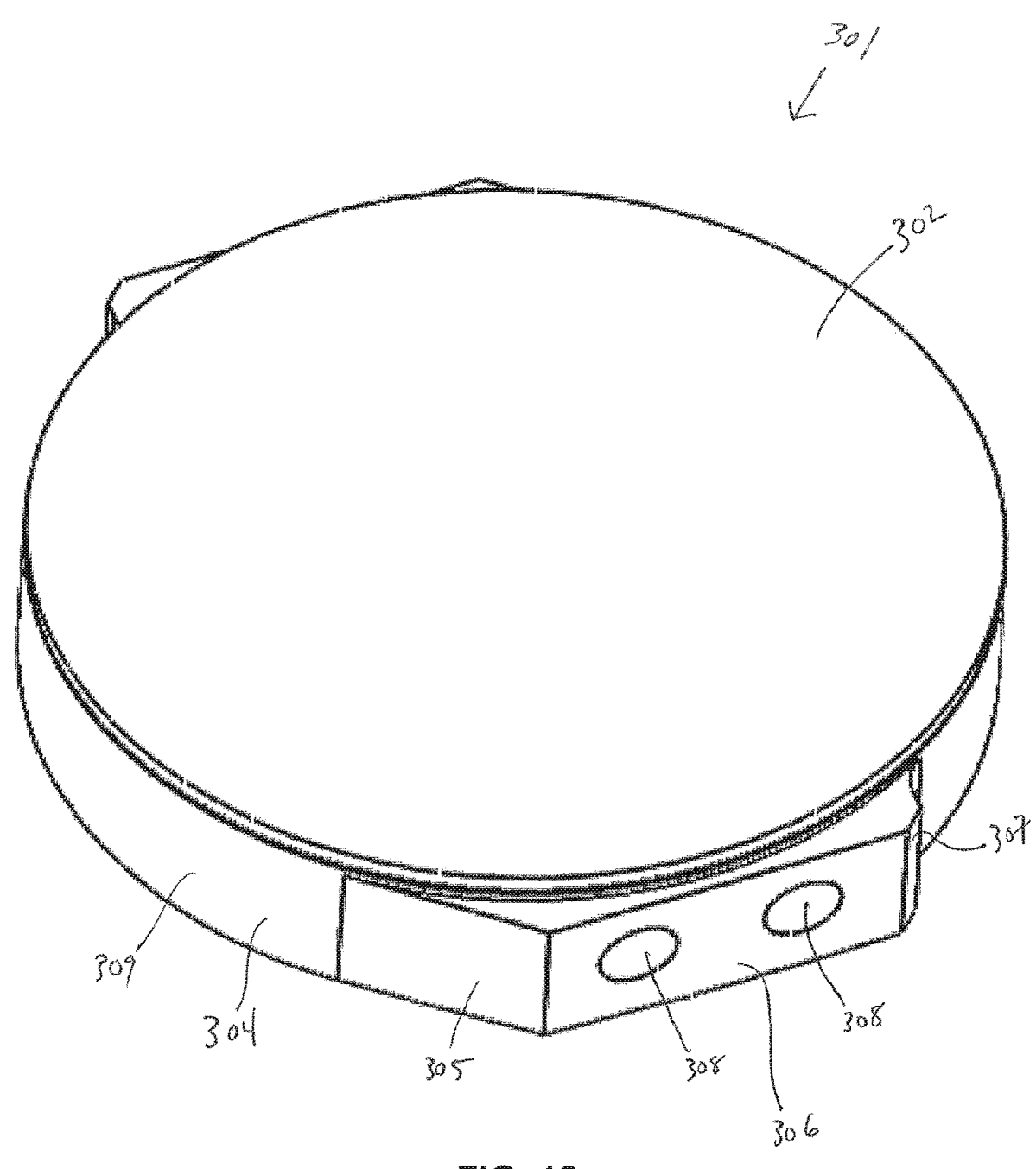
FIG. 18 shows an exemplary optic portion.

FIGS. 16-18 illustrate an exemplary interface between an exemplary optic body 301 (see FIG. 18) and haptics 310 that may help alleviate distortions due to shrinkage at the location where the optic body and haptics are secured. The interface between the optic body 301 and the haptics 310 is relocated radially away from the optic body 301, and specifically the optical surfaces, compared to other embodiments such as in FIGS. 10-15. By moving the interface, and thus the location of potential shrinkage, away from the optical surfaces, the amount of distortion caused to the optical surfaces by the curing step can be reduced. A coupling region 311 of haptics 310 each interface with an optic projection 303, such that the interface between the haptics and the projection 303 is radially away from the optical surface of the optic. This type of interface can be used with non-accommodating or accommodating intraocular lenses, but in this embodiment the lens is an accommodating intraocular lens.

For example, the accommodating intraocular lens 300 can comprise the optic body 301 (see FIG. 18), and haptics 310. Is this embodiment, haptics 310 are manufactured separately from the optic 310, and then secured to the optic 310. The haptics 310 each include a radially inner flat surface 312 (only one labeled in FIG. 16) that is secured to a radially peripheral surface 306 of the optic 310. In this embodiment surface 312 is a radially inner surface of the coupling region 311 of haptic 310. For example, an adhesive can be used to secure surface 312 to the radially peripheral surface 306 of the optic 310. The process of securing the haptic to the optic may affect the optical performance of the optic 70, as discussed above. For example, the curing process of the adhesive may cause shrinkage of the optic 301 at two discrete locations, thus possibly resulting in distortion and aberration such as astigmatism of the intraocular lens.

In this embodiment, the intraocular lens comprises two projections 303 extending radially outwards away from a peripheral surface 309 of the posterior element 304 of optic 301. The projections 303 can be thought of as projections from the general curved periphery of the optic, as defined by outer edge surface 309. The haptics 310 can each have a first portion 311 secured to the projection 303 and a free second portion 315 disposed away from the first portion 311, wherein a radially inner surface of each of the haptics follows a radially outer peripheral surface of the optic. Projection 303 may also be referred to herein as a "landing" or "land" in this disclosure.

Projections 303 can be raised areas extending between 10 microns and 1 mm, optionally between 10 microns and 500 microns, radially outward from the periphery surface 309 of the optic. The radially peripheral surface 306 of the projections 303 can be between 10 microns and 1 mm, optionally between 10 microns and 500 microns, farther away radially from a center of the optic than the peripheral surface 309 of the optic. For example, projections 303 can be a raised area extending between 100 microns and 200 microns radially outward from the periphery surface 309 of the optic. The radially outer peripheral surface 305 of projection 303 may be between 100 microns and 200 microns farther away radially from a center of the optic than the peripheral surface 309 of the optic. Values outside the above range are also possible. Projections 303 can move the securing surfaces or coupling surfaces away from the optic to prevent optic disruption due to shrinkage when curing the adhesive between the optic and the haptic.

In some embodiments the optic has a circular shape, in a top view, and the radially outer peripheral edge 309 of the optic is generally circular. When the projections are described herein as extending radially away from the optic body, the projections may be extending away from the general curve of the radially outer peripheral edge of the optic.

In some embodiments, the optic and the projections 303 of the intraocular lens can be a single integral body. For example, projections 303 can be molded as part of the optic. In some other embodiments, projections 303 can be attached to the optic, such as by gluing.

In some embodiments the optic 301 comprises a posterior element and an anterior element, optionally defining a fluid chamber therebetween, such as in embodiments above. For example, projections 303 can be part of the posterior element because the posterior has a thicker periphery. The projections may also be part of the anterior element. For yet another example, the projections can be part of the posterior element and anterior element of the optic.

Outer surfaces 306 of projections 303 and inner surfaces 312 of haptics 310 can all be flat, such that they interface at a butt joint. For example, the radially outer peripheral surface 306 of projections 303 can comprise a flat surface, optionally entirely flat. The radially inner surface 312 of haptics 310 can comprise a flat surface as well, optionally entirely flat. For another example, the radially outer peripheral surface 306 of projections 303 can comprise a curved surface, optionally entirely curved. The radially inner surface 312 of haptics 310 can comprise a curved surface as well, optionally entirely curved. A curvature of radially outer peripheral surface 306 can be the same as the curvature of the periphery surface 309 of the optic body, and in some embodiments can be larger or smaller than the curvature of the periphery surface 309 of the optic body.

Haptics 310 can comprise a peripheral fluid chamber as described herein. The projections 303 can comprise at least one fluid channel 308, and optionally at least two channels, in fluid communication with the peripheral fluid chamber in the haptics. The raised projections 303 may provide more stability to the fluid channel because there is more optic material at the locations of the projections.

In general, the projection can be disposed on a non-accommodating (fixed power) intraocular lens that is manufactured by coupling haptics and optic as well. For example, a fixed power intraocular lens, where the intraocular lens is a non-fluid filled optic body with a single power (e.g., PMMA material) and two haptics, can comprise a projection extending radially outwards from a peripheral surface of the optic body as well.

The embodiment in FIGS. 16-19 also illustrate an alternative haptic cross sectional configuration (see FIG. 19 for the cross section) that can be incorporated into any of the suitable optics herein, such as optic 100 shown in FIG. 10. The height H (measured in anterior to posterior direction) of haptics 310 can be from 2 mm-2.5 mm, and may be 2.1 mm to 2.4 mm. This may be smaller than other haptic heights for other intraocular lenses, such as heights above 3 mm. It may be advantageous, but not necessarily necessary, to have heights between 2 and 2.5 mm for the haptics. There is some patient to patient variability in the size of the anatomy in the eye. There is variability in capsular size, for example, or distance between capsule and the posterior side of the iris. With some haptics, there may be some rubbing between the haptic and the posterior side of the iris. And even if there is, it may not raise any concerns. It may thus be advantageous, merely in an abundance of caution, to have haptics heights that minimize the chance of such rubbing.

Haptics 310 also include a radially inner wall portion 313 on the radially inner side of fluid chamber 316, which has a thickness "ti" that is greater than a thickness "to" of the haptic wall on the radially outer side of chamber 316. In some embodiments "ti" is between four and nine times greater than "to." Radially inner wall portion 313 may be referred to herein as a "spacer." As shown in FIG. 16, the spacer extends along almost the entire length of haptic, but does not exist where the spacing exists between the optic and haptic. The fluid chamber 316 radially inner wall is, as shown, flatter than fluid chamber 316 radially outer wall. Haptics 310 are examples of haptics that have a cross section, in a plane passing through an optical axis of the optic portion, in which the haptic fluid chamber is disposed in a radially outer portion of the haptic, and wherein a radially inner portion of the haptic is non-fluid. Haptics 310 are examples of haptics that, in a cross section of a plane passing through an optical axis of the optic portion, and in a direction orthogonal to an optical axis of the optic portion through a midpoint of the haptic, have a radially inner fluid chamber wall thickness that is between four and 10 times the thickness of a radially outer fluid chamber wall thickness. Haptics 310 are examples of haptics that, in a cross section of a plane passing through an optical axis of the optic portion, has an outer surface that is not symmetrical about any axis passing through the peripheral portion and parallel to an optical axis of the optic portion, and wherein the haptic has, in a direction orthogonal to an optical axis of the optic portion through a midpoint of the haptic has a radially inner fluid chamber wall thickness greater than a radially outer fluid chamber wall thickness. Haptics 310 are examples of haptics that, in a cross section of a plane passing through an optical axis of the optic portion, having a height dimension measured in an anterior to posterior direction, wherein the greatest height of the peripheral portion in a radially outer half of the peripheral portion is greater than the greatest height of the peripheral portion in a radially inner half of the peripheral portion.

In some embodiments one or more aspects of the optic body have a refractive index that is between about 1.48 and 1.55, such as between 1.50 and 1.53. In some embodiments the refractive index of one or components is about 1.48, about 1.49, about 1.50, about 1.51, about 1.52, about 1.53, about 1.54, or about 1.55. There may be a designed mismatch in refractive index between any of the anterior element, fluid, and posterior element, but in some embodiments there is a designed index matching between at least two of the components, and optionally all three. When all components of the optic are designed to have the same or substantially the same index of refraction, they are said to be index-matched. Any of the properties of the intraocular lenses (e.g., refractive index, fluid, monomer compositions) described in U.S. Prov. App. No. 62/173,877, filed Jun. 10, 2015 can be implemented in any of the intraocular lens designs herein.

Exemplary materials that can be used to make any of the IOLs, including fluid, herein, can be found in PCT/US2016/037055, fully incorporated by reference herein.

As described in some embodiments above, the accommodating intraocular lens can include first and second haptics that are adhered to the optic, and optionally about 180 degrees from one another around the optic. During lens formation, the haptics are adhered, or glued, to the optic, with an adhesive. The haptic/optic adhesion is important for a variety of reasons. The haptics are deformed away from the optic, or splayed, during loading and delivery. It may be beneficial to have a relatively softer adhesion joint between the optic and haptic to help with the deformation of the haptic. If the haptic/optic joint is too rigid, it may be difficult to deform the haptic or the haptic/optic joint during loading and/or delivery. Secondly, the haptics are joined to the optic at two discrete locations around the optic. That is, the joint between the haptic and optic does not extend all the way around the optic. This creates an opportunity for the haptic/optic coupling to interfere with the desired optical quality of the optic. For example, during curing of an adhesive used to adhere the optic to the haptic, the adhesive can shrink and disrupt optical quality of the optic, such as by creating an astigmatism in the optic. To the contrary, it may not be as important to use a low modulus adhesive for adhering the anterior element and the posterior element in the optic, since that joint is annular, and shrinkage will not occur at discrete locations, like with the haptic/optic coupling. In fact, it has been shown that optical quality of the optic can be improved as a consequence of having a relatively rigid adhesion ring joining the anterior and posterior elements of the optic. For at least these two reasons, in some embodiments the adhesive for the haptic/optic joint may be a relatively low modulus adhesive.

As set forth above, the adhesives used can include a CLP as a first primary component and a reactive acrylic monomer diluent (e.g., ADMA) as a second primary component, and can also include a third component. In general, as the CLP percentage goes up, the amount of shrinkage during curing goes down. It can thus be beneficial to increase the amount of the CLP in an adhesive when used for securing at least components together in which it is desirable to reduce the amount of shrinkage that occurs, such as with a haptic/optic joint. In some of the embodiments above the second primary component (e.g., ADMA) is present in amount of about 18% to about 43%. While the adhesives in those examples could be used for the haptic/optic adhesive, some adhesive on the higher end of that range may be better suited for the optic joint between the anterior and posterior elements, which there is less concern for the shrinkage occurring all the way around the optic rather than at discrete locations.

In some embodiments, the adhesive for a haptic/optic coupling has a greater percentage of a CLP than the optic adhesive (between the anterior and posterior elements). Similarly, in some embodiments the adhesive for the haptic/optic coupling has less of a reactive acrylic monomer diluent (e.g., ADMA) than the optic adhesive. In some embodiments the adhesive for the haptic/optic coupling has about 5-35%, such as 10-30%, or 15-25%, of the reactive acrylic monomer diluent (e.g., ADMA). The CLP can be about 50-85% of the adhesive. A third component, such as laurel methacrylate, can also be included to increase strength, flexibility, and provide low shrinkage. Laurel methacrylate is an example of a material with a low modulus, low shrinkage, and has similarly low diffusion characteristics as the reactive acrylic monomer diluent (e.g., ADMA). This helps make the bonds between the haptic and optic softer. In some embodiments securing the haptics to the optic creates no more than a +/−0.3 D change in the optic during manufacturing.

Table 1 lists some exemplary adhesives that can be used, for example, as adhesives for the haptic/optic coupling. Each example also includes 2.3% of a photoinitiator, such as Darocur 4265. SR 313 is lauryl methacrylate, and provides water resistance, weatherability, impact strength, flexibility, and low shrinkage, and other advantage described herein. Exemplary shrinkages are provided for some examples.

TABLE 1

| Adhesive | CLP-1.5% F | ADMA | SR 313 | DMA @ 35° C. | | DMA @ 20° C. | | Viscosity 40° C. | E' at 20 C. (MPa) | E' at 35 C. (MPa) | Shrinkage % |
|---|---|---|---|---|---|---|---|---|---|---|---|
| | | | | 0.1 Hz | 1.0 Hz | 0.1 Hz | 1.0 Hz | | | | |
| Gen 0-(65:35) (1:0) | 63.50 | 34.20 | 0.00 | 229 | 400 | 347 | 750 | 28000 | 495.7 | 245.2 | 1.84 |
| SH11743-B-(70:30) (1:0) | 68.39 | 29.31 | 0.00 | n/a | 140 | n/a | 380 | | | | |
| X8-(63.5:36.5) (2:1) | 63.51 | 22.80 | 11.40 | 37 | 75 | 61 | 200 | | | | |
| X5-(68.4:31.6) (3:1) | 68.39 | 22.00 | 7.31 | 52 | 90 | 85 | 220 | | | | |
| X4-(67.5:32.5) (2:1) | 67.50 | 20.13 | 10.07 | 29 | 55 | 53 | 180 | 21233 | 120.8 | 45.7 | 1.52 |
| X7-(73.3:26.7) (2:1) | 73.28 | 16.28 | 8.14 | 14 | 30 | 26 | 100 | | | | |
| X2-(67.5:32.5) (1:1) | 67.50 | 15.10 | 15.10 | 4 | 9 | 7 | 55 | 16471 | 16.6 | 3.1 | |
| X6-(78.2:21.8) (2:1) | 78.16 | 13.03 | 6.51 | 5 | 15 | 10 | 55 | | | | |
| X3-(67.5:32.5) (1:2) | 67.50 | 10.07 | 20.13 | 1 | 3 | n/a | 11 | 13011 | 4.0 | 45.7 | |

In some alternative to the some embodiments above, the optic adhesive includes, in addition the CLP, HEA rather than HEMA.

The disclosure now includes a description of exemplary intraocular lenses that may help reduce posterior capsule opacification ("PCO"). Posterior capsule opacification (PCO) may be a major long-term complication of successful cataract surgery with some intraocular lens (TOL) implantation. The residual lens epithelial cells (LECs) can proliferate and migrate from the peripheral posterior capsular bag into the space between the capsule and the optic of the intraocular ocular lens (TOL). This phenomenon can lead to PCO and decreased visual acuity.

Some accommodating intraocular lenses, for example, the accommodating intraocular lenses described above, have been demonstrated to have the ability to reduce or delay PCO. For example, haptics described above can fill the peripheral capsular bag and likely reduce LECs proliferation by tight contact with the capsule bag. However, this contact may not occur for the entire 360° around the capsule, and there may be gaps between the distal end tip of one haptic and the other haptic, or there may be gaps between the optic and the interior of the haptic adjacent the optic/haptic coupling location.

There may be, in some situations, advantages for peripheral portions of intraocular lenses to be configured and adapted to further reduce the PCO effect to increase visual acuity.

FIG. 17 shows a top view of an exemplary intraocular lens, in which the spacing between the optic and haptics can be seen, as well as the coupling between the optic and haptics.

As shown in FIG. 17, though the haptics 310 can substantially fill the peripheral capsular bag and likely reduce or prevent cellular proliferation by tight contact with the capsular bag, this contact is not entire 360° around the capsule. There are small gaps between the distal end tips 315 of the haptics and the proximal ends of the optic haptic. The residual LECs can proliferate and migrate from the peripheral capsular bag, such as from the equatorial region, into the space between the capsule and the optic of IOL. LECs growth through the gap can be observed, which can lead to PCO and decreased visual acuity. In addition, LECs have been observed in the space between the optic and the interior haptic adjacent to the location wherein the haptic couples to the optic.

Figure 20:
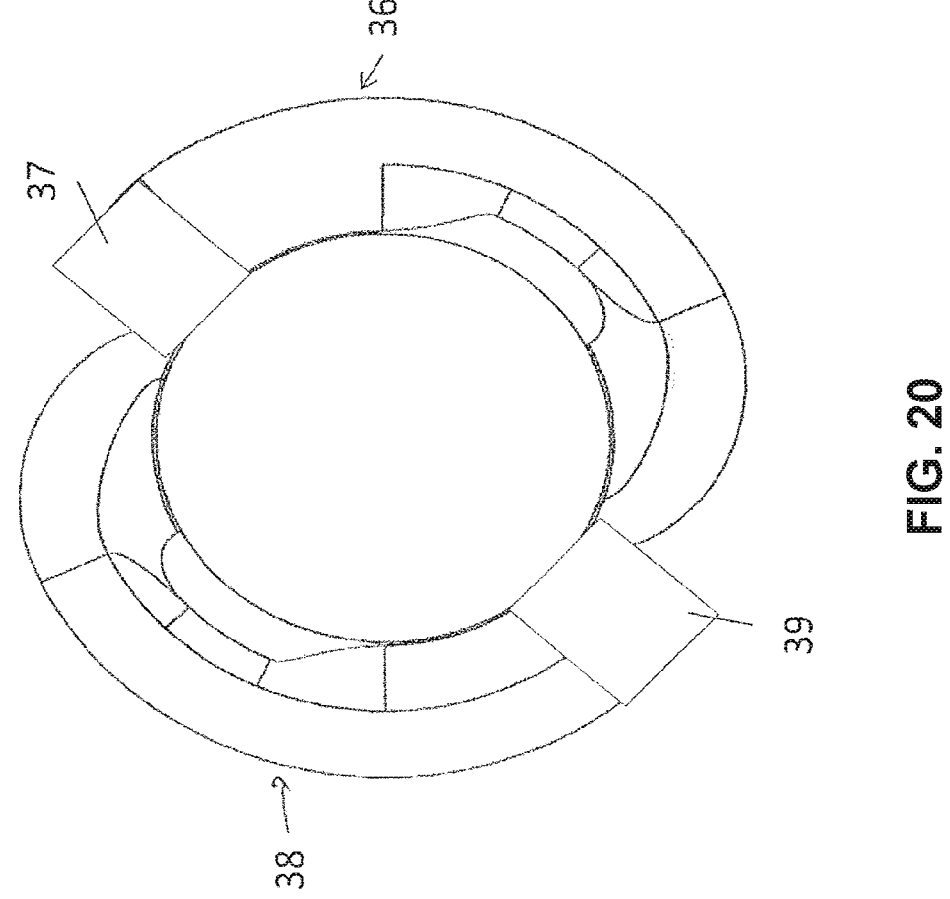
FIG. 20 shows a top view of an exemplary IOL.

FIG. 20 is a top view illustrating an exemplary IOL comprising one or more blunt tips 37 and 39 of the haptics. One or both of the tip of a first haptic and the proximal end of the second haptic can be configured to more closely fit together and reduce or eliminate the gap between the free end tip 37 of first haptic 36 and the proximal end of the second haptic 38, and the gap between the free end tip 39 of second haptic 38 and the proximal end of the first haptic 36. The blunt 90° tips 37, 39 can reduce the gaps and reduce PCO effect by preventing or reducing cell migration and proliferation.

In some embodiments the distal tip of a first haptic can overlay, or overlap (in a top view), the proximal portion of the second haptic to reduce or eliminate the gap. For example, the distal tip of a first haptic can be tapered to overlay the second haptic. The free end of the second haptic can also be overlay (e.g., tapered) to overlay the first haptic to reduce or eliminate the gap. The proximal ends of these exemplary haptics are tapered towards the coupling location with the optic, so the distal ends of the adjacent haptic can similarly be tapered (such as with a complimentary taper) to form the overlapping regions of first and second haptics. Since the IOL is dialed clockwise, the proximal end can be configured to have a taper while the distal tip can be configured with a variety of shapes. In some other embodiments the distal tips can further comprise a radial barrier to prevent circular migration of LECs which can contribute to LECs growth in the gap.

Figure 21:
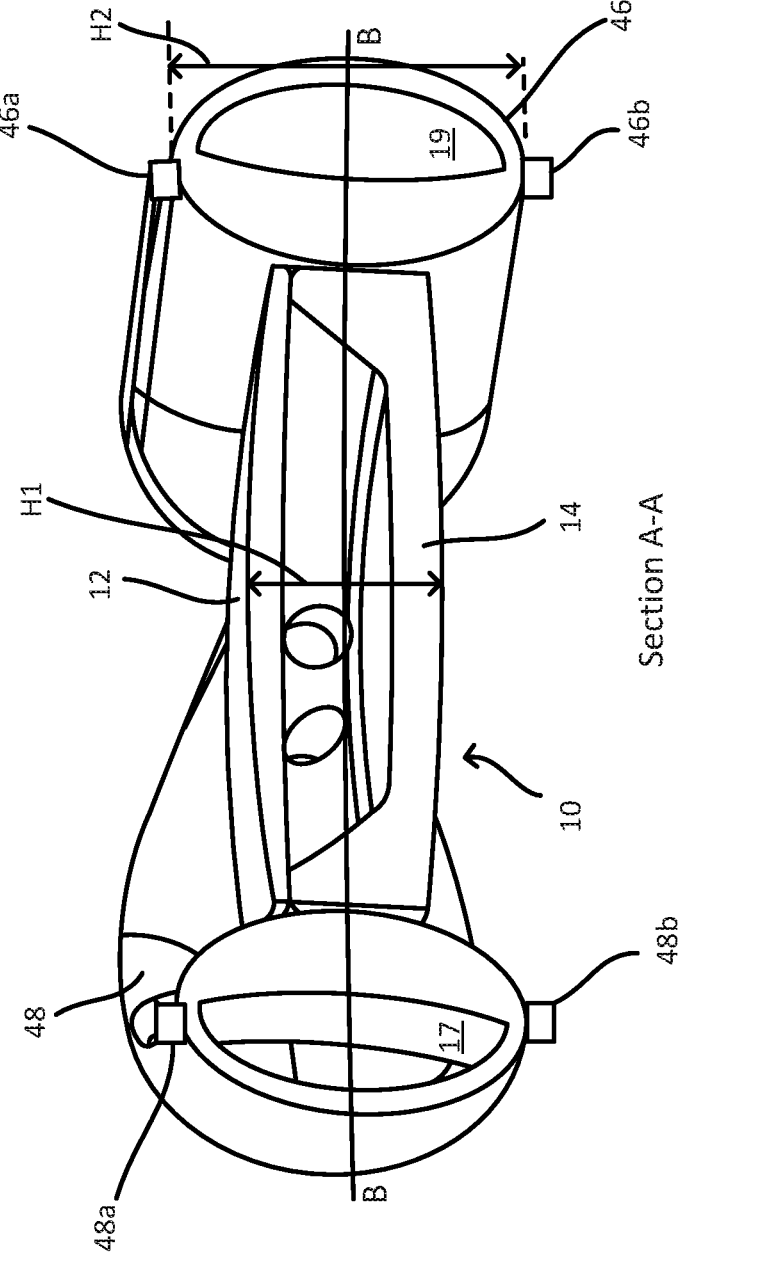
FIG. 21 shows a sectional view of an exemplary IOL.

FIG. 21 illustrates a section view of an exemplary IOL with one or more circumferential ridges (e.g., 46a, 46b, 48a, and 48b) on the haptics 46 and 48. Only a section of the ridges are shown, but the ridges extend along at least a portion of the length of the haptics. The haptic/bag contact can be improved with the one or more circumferential ridges (e.g., 46a, 46b, 48a, and 48b) having sharp edges (i.e., not smooth). For example, the one or more ridges 46a, 46b with sharp edges can extend along at least a portion of the length of and on an outer surface of the haptics 46. The ridge 46a can be disposed on a top surface of the haptic 46 while the ridge 46b can be disposed on a bottom surface of the haptic 46. Similarly, the one or more ridges 48a, 48b with sharp edges can extend along at least a portion of the length of and on an outer surface of the haptics 48. The ridge 48a can be disposed on a top surface of the haptic 48 while the ridge 48b can be disposed on a bottom surface of the haptic 48. In this exemplary embodiment, the "top" is considered the anterior portion and the "bottom" is the posterior portion. Axis (or plane) B-B is considered to divide the IOL between anterior and posterior sides, and axis or plane B can be considered to pass through the "equator" of the haptics (which are generally aligned with the equator of the capsular bag). For example, ridges 48a and 46a are disposed on the anterior side of the haptics, and ridges 46b and 48b are disposed on the posterior side of the haptics. As shown in FIG. 21, each of the ridges 46a and 48a protrude from a rounded anterior outer surface of the haptic 48 and each of the ridges 46b and 46b protrude from a rounded posterior outer surface of the haptic 48. Each of the haptics 48 can comprise a haptic fluid chamber in fluid communication with the optic fluid chamber. The haptic fluid chamber is surrounded by an anterior chamber wall, a posterior chamber wall, and lateral chamber walls. The rounded anterior outer surface of the haptic 48 is an outer surface of the anterior chamber wall and the rounded posterior outer surface of the haptic 48 is an outer surface of the posterior chamber wall.

The ridges (e.g., 46a, 46b, 48a, and 48b) on the haptics 46, 48 can have cross sections with sharp edges, such as square edges. It has been found that square-edged optics can reduce the incidence of PCO effect following cataract surgery. It has been shown in earlier attempts, dating back to the early 1990s, that square-edged optics have reduced PCO development. Discontinuous capsular bend may be an important factor for the PCO prevention effect. In general, the proliferating LECs start from the equator and divide and migrate toward the center. The ridges (e.g., 46a, 46b, 48a, and 48b) on the haptics 46 or 48 can create barriers to LECs movement by creating capsular bends, thus creating a square edge effect. Therefore, LECs migration can be significantly reduced or eliminated by one or more of the ridges.

Figure 22:
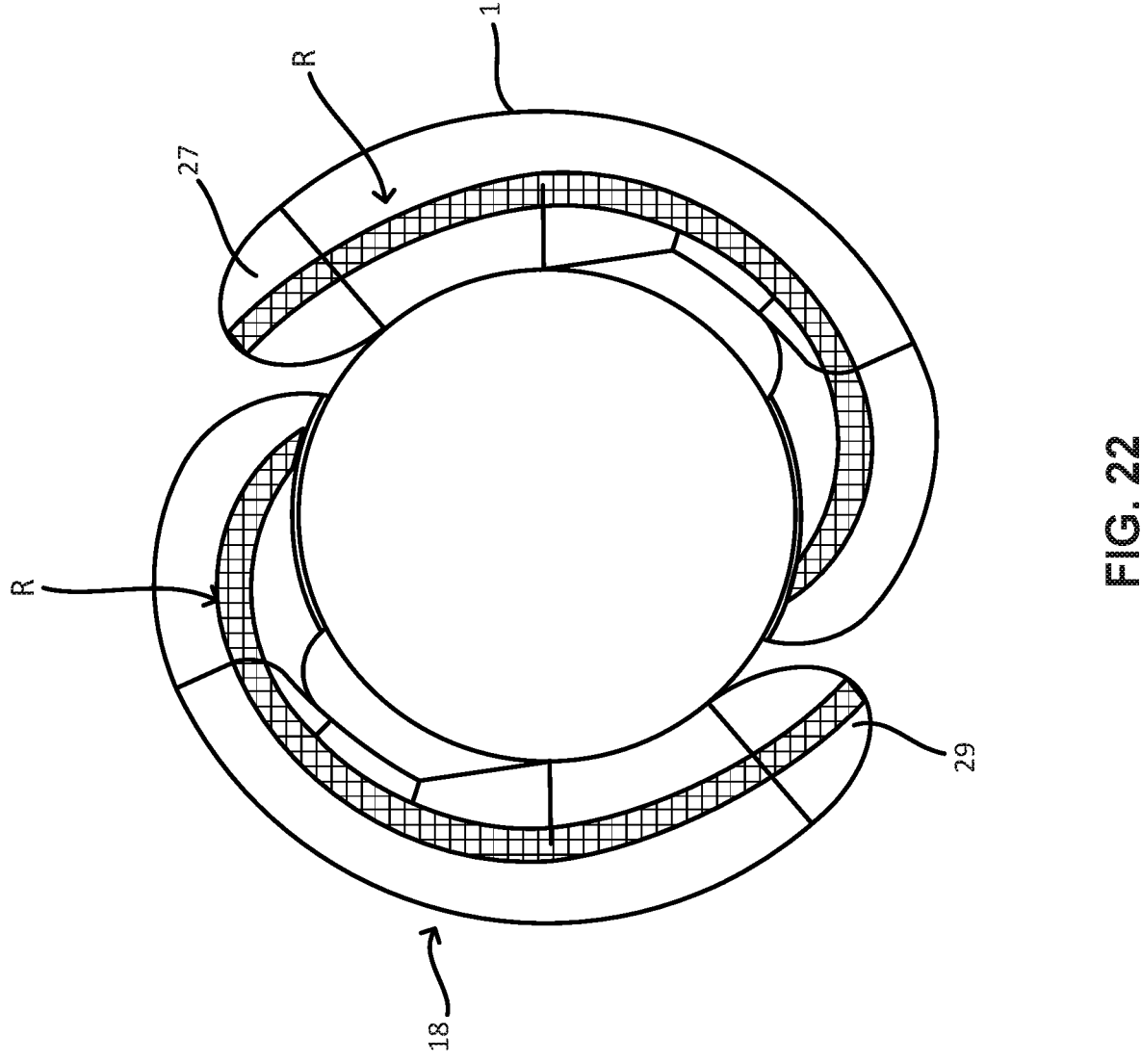
FIG. 22 shows a top view of an exemplary IOL.

FIG. 22 is a bottom (posterior) view of an exemplary IOL, illustrating ridges 46b and 48b of the two haptics (from FIG. 21), both ridges labeled "R" in FIG. 22. In FIG. 22, the ridges extend along the entire length of both haptics, but in some embodiments they do not extend along the entire length. For example, in some embodiments the ridges may extend along at least 75%, 80%, 85%, 90%, or 95% of the length of the haptic. The length of the haptic is measured along an equator of the haptic, from the coupling location with the optic, to the distal free end. The length of the haptic is thus generally measured along a curved line. The length of the haptic, may be, in some cases, considered a straight line measured as the shortest distance from the optic coupling location to the distal free end.

The ridges (e.g., 46a, 46b, 48a, and 48b) can extend along at least a portion of the length of the peripheral portion of the IOL. The peripheral portion can include one or more haptics, for example, 46 and 48, but the IOL may include more or less that two haptics. For example, the IOL may have a single annular peripheral portion with one or more ridges. The IOL could also have, for example, four haptics each its own coupling to the optic, wherein one or more of the four haptics includes one or more ridges The ridges (e.g., 46a, 46b, 48a, and 48b) can create "square edge effect" although the ridges may not need to be square. A triangular ridge may suffice. However, other shapes with at least one sharp edge can work as well. The phrase "sharp edge" as used herein refers to an edge that is not a rounded edge. In some embodiments the ridges can have at least one 90 degrees edge, in a cross section. In some embodiments the ridges can have at least one edge less than 100 degrees, in a cross section. In some embodiments the ridges can have at least one edge less than 120 degrees, in a cross section. In some other embodiments the ridge does not have a 90 degree edge in a cross section, for example, the ridge can have a 60 degrees triangle edge. In some embodiments at least two ridges (e.g., 46a and 46b) have the same configuration. In some other embodiments a first ridge has a different configuration than a second ridge (not shown). One or all of the ridges can have the same configuration, or some may have one configuration while others have a different configuration. For example, ridges on one side (e.g., anterior) may have a triangular configuration while ridges on the other side (e.g., posterior) may have a square configuration.

The height of the ridges (measured in the anterior-to-posterior direction) can be about 50 µm to about 500 µm in some embodiments, such as about 100 µm to about 300 µm. When the ridges have a square edge cross section, the width (measured radially) can be can be about 50 to about 500 µm in some embodiments, such as about 100 µm to about 300 µm. The ridges can be configured to be wide enough to prevent the ridge from folding over when implanting. The square edge cross section is defined herein as a cross section includes at least one edge less than 100 degrees. When the ridges have a triangle cross section, the base of the ridge can be similar in size, for example, about 50 µm to about 500 µm in some embodiments, such as about 100 µm to about 300 µm. The ridges do not need to be the same size (for example, one or more ridges can have different height and width values). Values outside the above ranges are also possible.

The haptic (e.g., 46, 48) can comprise a ridge (e.g., 46b, 48b) disposed on a posterior side (a bottom surface) in some embodiments. The haptic (e.g., 46, 48) can comprise a ridge (e.g., 46a, 48a) disposed on an anterior side (a top surface) in some other embodiments. In some embodiments the haptic (e.g., 46, 48) can comprise one or more ridges (e.g., 46a, 48a) disposed on an anterior side and one or more ridges (e.g., 46b, 48b) disposed on a posterior side to block LECs from both sides. The second ridge can further reduce the PCO effect, but in some instances the second ridge may not be required. One or both haptics can have more than one ridge on an anterior side, or more than one ridge on a posterior side. For example, haptic 48 can include two ridges 48b spaced apart from one another on haptic, but both being disposed on the posterior side of haptic.

In some additional embodiments the haptic (e.g., 46, 48) can comprise one ridge (not shown) disposed on the equator of the peripheral portion. For example, in FIG. 21, one or both haptics can include a ridge symmetric about axis or plane B-B, extending radially outward to the left or right in the figure. However, ridges on the equator of the haptic can be optional. The numbers of the ridges on a haptic can be, for example, 1, 2, 3, 4, 6, 8, 12, 20 or any numbers therebetween or any other numbers. For example, two ridges can be disposed circumferentially on an anterior portion (top) and on a posterior portion (bottom), 180° apart and optionally with one or more additional ridges between the anterior portion (top) and the posterior portion (bottom). In FIG. 21, ridge 48a and 48b are 180 degrees part, but they need not be. For example, ridge 48a could be moved 45 degrees toward the equator of haptic 48 while ridge 48b could be in the same position as shown. The ridges can be, but do not need to be symmetrically placed around the haptic.

The ridges described herein can be thought of generally as extensions that extend away from the natural curvature of the haptic. For example, when a square edge is used, the transition between the haptic curvature and the ridge can be a region where the haptic has a sharp bend, or tight curve, as the ridge extends away from the surface of the haptic. The ridge can be described in this manner at both transition regions with the general curvature of the haptic.

The ridges can be formed in a number of ways. The haptic can be molded with the one or more ridges formed therein (considered integral with the haptic material). Alternatively, separate sections of material can be adhered to the outer surface of the haptic after the haptic is molded (considered non-integral with the haptic material). Any of the ridges can be the same or different material as the haptic material. For example, one or more ridges can be a material that is stiffer than the haptic material that can be adhered (e.g., glued) or co-molded onto the haptic.

Figure 23A:
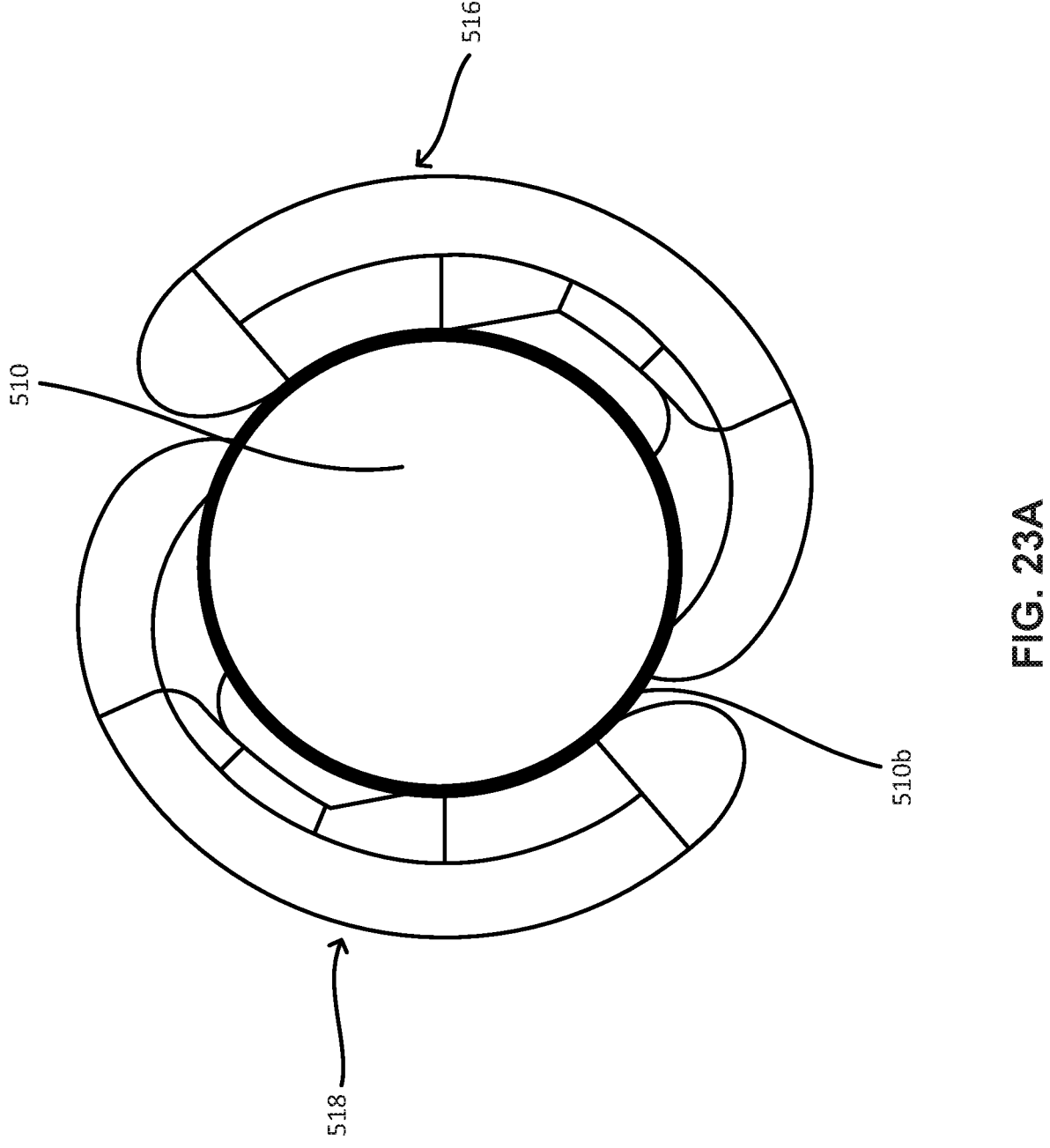
FIG. 23A shows a top view of an exemplary IOL.
Figure 23B:
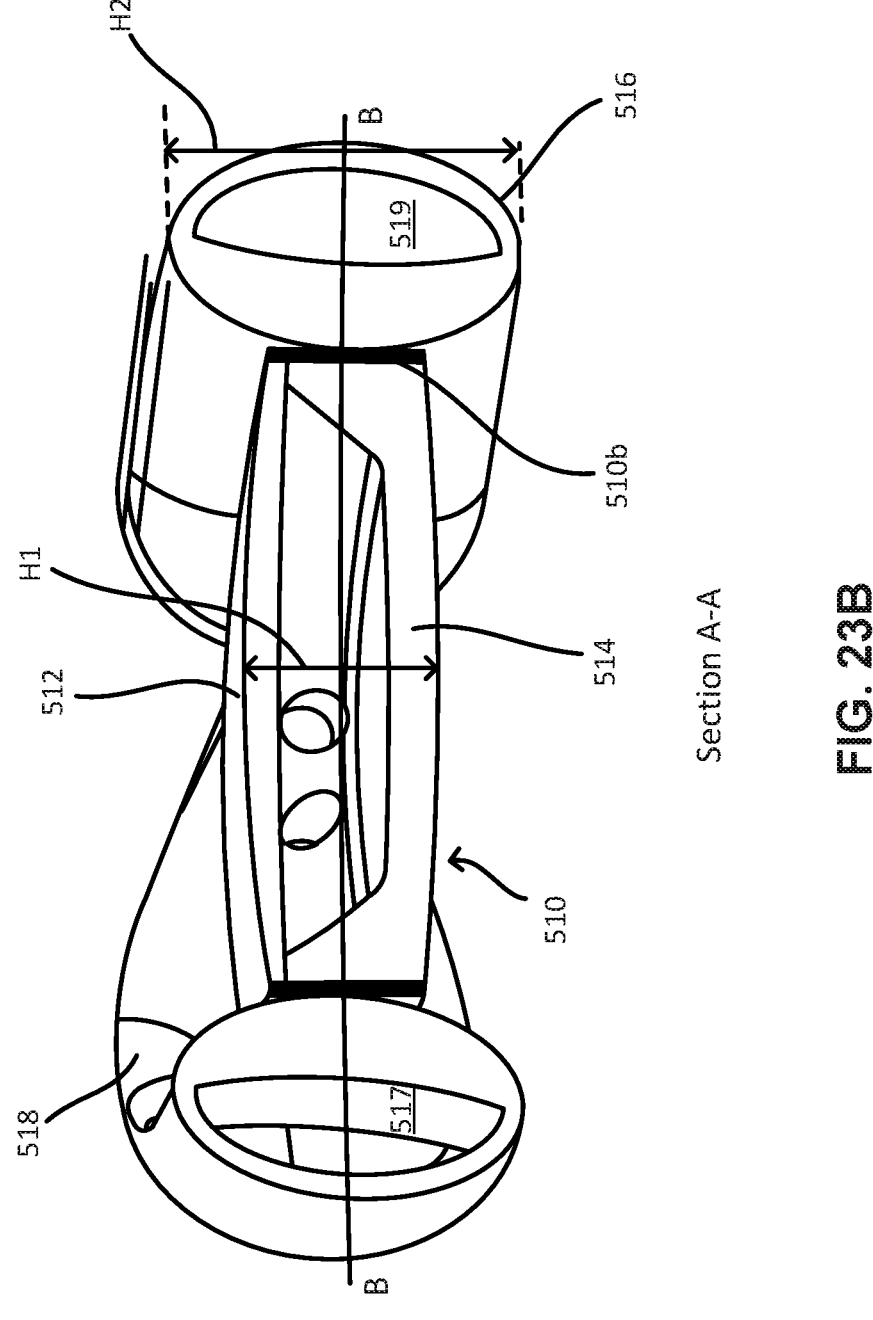
FIG. 23B shows a sectional view of an exemplary IOL.

For some intraocular lenses, scattering from the periphery of the optic portion of the intraocular lenses can reduce the optical quality of the intraocular lens. It may be beneficial, but not necessary, for the intraocular lens to be further adapted and configured to reduce peripheral scattering. FIG. 23A illustrates a top view of an exemplary IOL comprising an opaque periphery. FIG. 23B illustrates a perspective section view of the IOL comprising an opaque periphery from FIG. 23A. Referring to FIGS. 23A-B, an intraocular lens (IOL), for example, an accommodating intraocular lens, can comprise an optic portion 510, an opaque periphery 510b around the optic portion 510, and a peripheral portion optionally including at least two haptics 516 and 518 coupled to the optic portion 510. The opaque periphery 510b can be adapted to absorb the scattered light, thus limit light scattering. As shown in FIGS. 23A and 23B, the opaque periphery 510b can be disposed only on a peripheral-most lateral surface of the optic portion 510.

In some embodiments the opaque periphery 510b comprises a layer of opaque material, optionally a polymer, disposed on a peripheral edge of the optic portion. A layer of opaque polymer may need to meet the requirements for implantable materials. A layer of opaque polymer may also need to be bio-compatible and have stable properties. In some embodiments an opaque polymer can co-molded with the optic portion 10 during the IOL manufacturing process. In some embodiments an opaque polymer can be deposited on a peripheral edge or peripheral-most lateral surface of the optic portion 10 after the IOL has already been manufactured.

In some embodiments the opaque periphery 510b can comprise a layer of black glue disposed on a peripheral edge or peripheral-most lateral surface of the optic, which could also be used as a glue to adhere the optic and haptics.

In some embodiments the opaque periphery 510b comprises a layer of black paint disposed on the optic edge or peripheral-most lateral surface of the optic portion.

In some embodiments the opaque periphery 510b comprises a cylindrical structure, such as a black cylindrical structure, attached to an edge or the peripheral-most lateral surface of the optic portion 510. This approach can reduce the complexity in the IOL manufacturing. A variety of methods can be used to attach a cylindrical structure to the IOL.

FIGS. 24-26C, which will now be described, are related to the full disclosure in WO2014/145562A1, which is incorporated by reference herein. A variety of intraocular lens ("IOL") loading and delivery devices, systems, and methods of use have been described in recent years. However, the issues related to residual air have not been adequately addressed yet. For example, residual air around the IOL and in the fluid chambers of the injector system can lead to issues during IOL delivery. For example, air in a viscoelastic stream before and around the IOL during delivery can obscure the visualization of the IOL and eye during delivery and after delivery during the manipulation and final placement of the IOL in the eye, such as in the capsule. Additionally, compressed residual air behind the IOL during the highest pressure of the IOL body delivery can lead to uncontrolled delivery of the IOL into the eye. This can occur as the IOL body passes the most constricted portion of the delivery device, and allows the compressed air proximal of the IOL to expand and push the IOL forward without user input. While this could theoretically be used as an advantage in some types of delivery, uncontrolled IOL delivery is generally undesirable.

Loading and delivery devices, systems, and method of use are needed that can effectively perform air management, including residual air removal in loading and pre-delivery.

Figure 24:
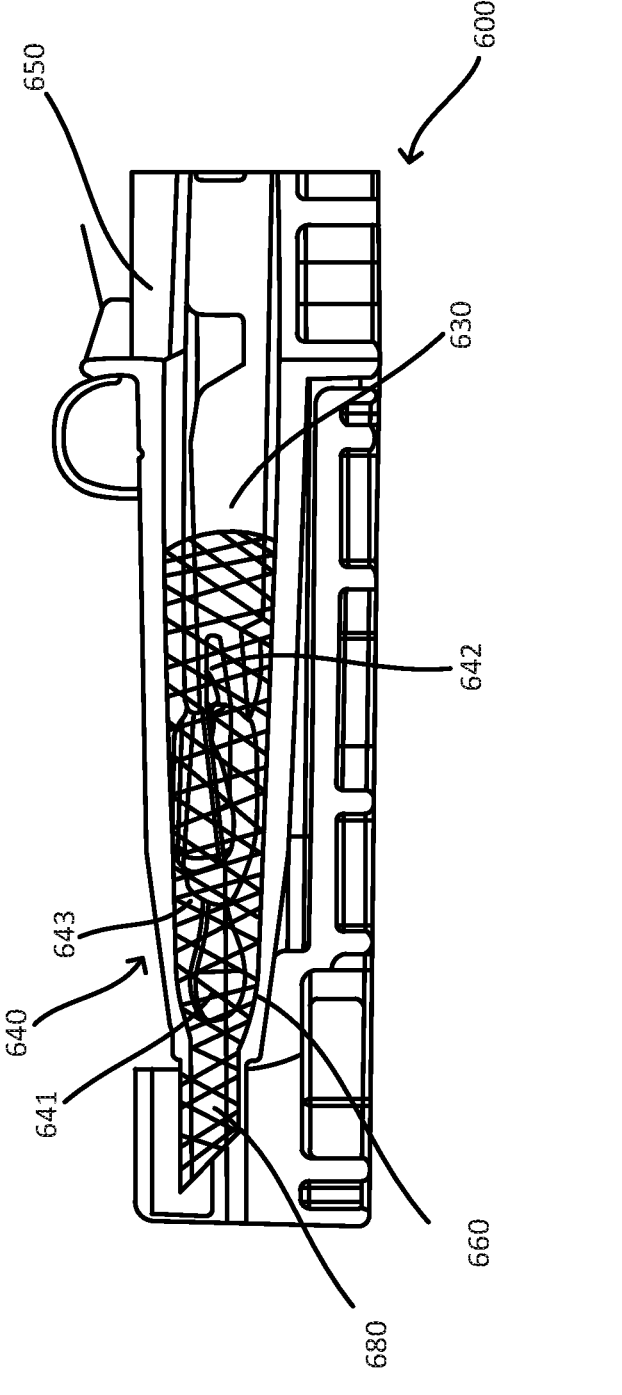
FIG. 24 is a section view of a cartridge with an IOL loaded inside.

FIG. 24 is a section view of a cartridge 660 with an IOL 640 loaded inside by a push member 630 according to one embodiment of the disclosure. The IOL 640 can be any of the IOLs described above, or may in some embodiments be an IOL not described herein. For example, the IOL 640 can be the same or similar to the IOL 340 in FIG. 22 in WO2014/145562A1. The IOL 640 can comprise optic portion 643, leading haptic 641 and trailing haptic 642 as shown in FIG. 24. Leading haptic 641 is disposed distally to optic 643, and trailing haptic 642 is generally proximal to optic 643. The cartridge 660 can be any type of cartridge, such as those described herein or even other cartridges not described herein. For example, the cartridge 660 can be the same as or similar to the exemplary cartridge 360 in FIG. 18. The carrier 600 can be any type of carrier, shown herein or not. For example, the carrier 600 can be the same as or similar to the cartridge 400 in FIGS. 16, 17 and 18 in WO2014/145562A1. The cartridge 660 can be secured to the distal cartridge receiving area of carrier 600.

Prior to use, the loading carrier 600 can be sterilized and shipped with the IOL 640 disposed therein. Optionally, the cartridge 660 can be attached before sterilization, or the cartridge 660 can be attached at the time of loading. A viscoelastic material 680 can be introduced to the carrier 600 through a port in the side of the loading carrier 600 that has a communicating port adjacent to the IOL 640. For example, the viscoelastic port (not shown) can be the same as or similar to the side port 319 in FIGS. 16 and 17 in WO2014/145562A1. The viscoelastic port can be designed to mate with standard syringes, and has a pathway that leads to the proximity of the IOL 640. The port conveys viscoelastic from a syringe or other viscoelastic delivery aid to the area around the IOL 640 prior to the splaying and loading steps.

The push member 630 can be any type of push member or loading member, shown herein or otherwise. The push member or loading member 630 can move distally to engage with and advance the IOL 640 into the cartridge 660 (or other delivery device or delivery lumen) and placing it at a predefined position in the cartridge 660 to be ready for further assembly of a delivery device, such as a plunger. In some embodiments, the push member 630 can be the same as or similar to the push member 330 in FIGS. 17 and 20 in WO2014/145562A1. The push member or loading member 630 can comprise an elongate body, a first extension extending distally and in an upward direction relative to a top portion of elongate body at a hinge and a second extension extending distally and in a generally linear orientation with respect to the proximal portions of load body, similar to the loading member in FIG. 20 in WO2014/145562A1. In some other embodiments, the push member 630 can be the same as or similar to the push member 40 in FIG. 14 in WO2014/145562A1.

The carrier 600 can comprise a carrier cover, or lid 650, and can be any of the lids herein. Lid 650 can cover the portion of base 610 where the IOL 640 is positioned.

As shown in FIG. 24, loading the IOL 640 from the loading carrier 600 and into the cartridge can result in the IOL 640 being disposed in the cartridge 660, surrounded by the viscoelastic material 680, but with localized air bubbles over the anterior portion of the IOL 640 and near the proximal haptic 642. If this air is not removed, it can move forward of the IOL 640 during delivery and obscure visibility during the surgery, as mentioned above.

The disclosure includes exemplary methods of air management in an IOL loading and delivery system. The methods will be described generally without reference to specific parts of the devices herein, although examples will be given in the context of certain embodiments. Not all steps need necessarily be performed, and the order may vary.

Figure 25A:
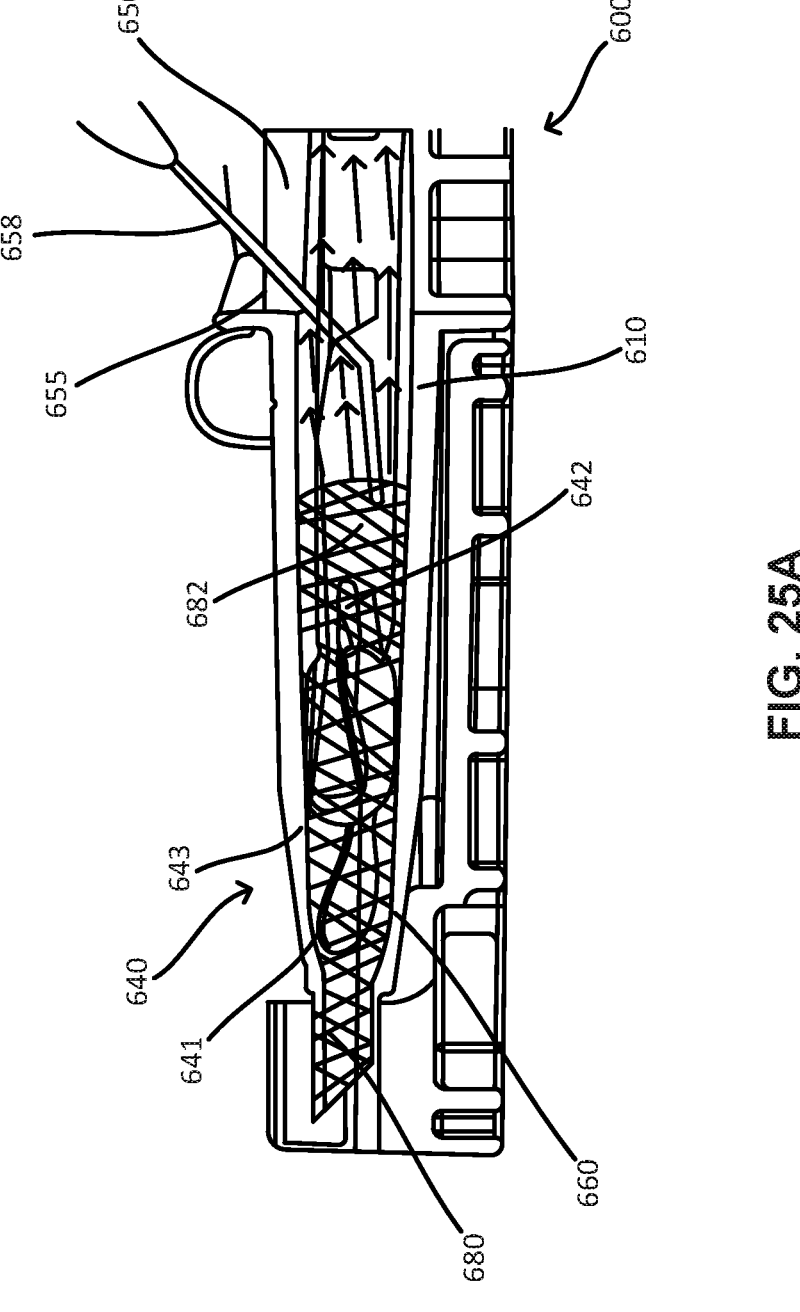
FIGS. 25A, 25B, 25C illustrate a method of air venting during the delivery process.
Figure 25B:
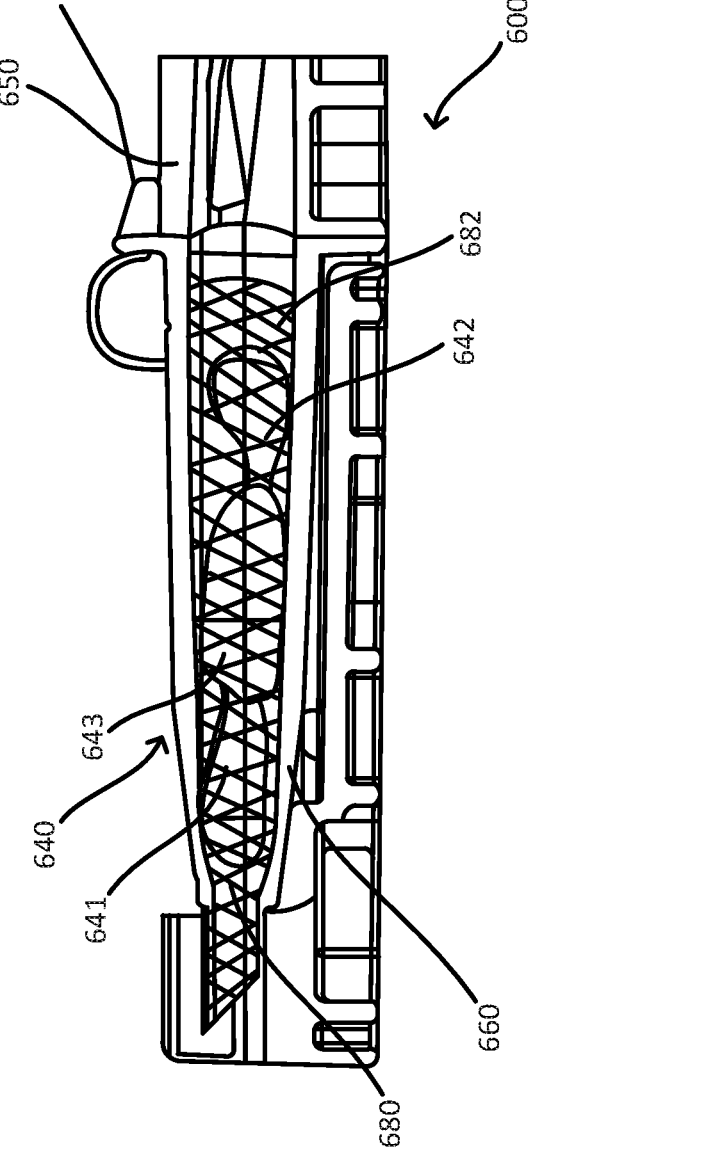
Figure 25C:
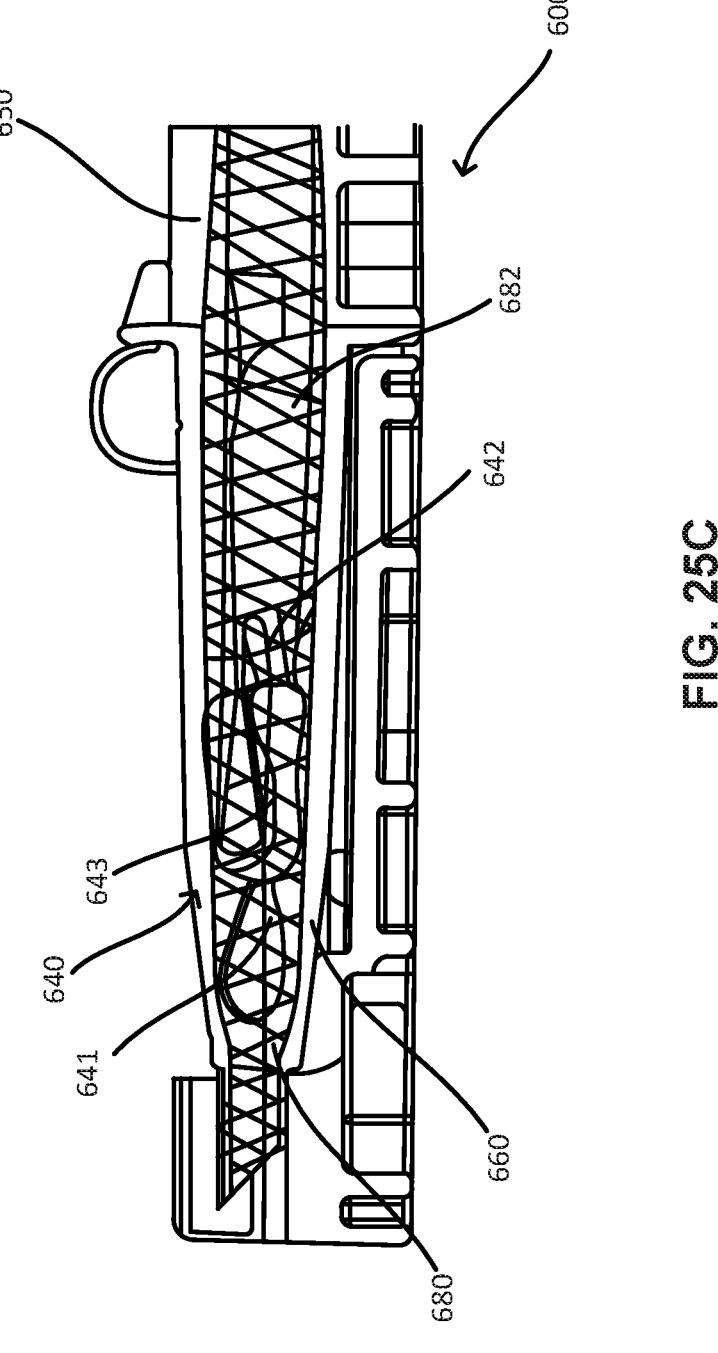

FIGS. 25A-C illustrate a method of removing air (or "de-bubbling") from around the IOL 640 during loading, and before connecting a delivery device to the cartridge 660. In general, the air over the anterior portion of the IOL 640 and near the proximal haptic 642 can be removed or displaced away from the IOL 640 before mounting the delivery device, for example, a plunger assembly, to the cartridge 660.

In some embodiments, the method can comprise removing the cartridge from the carrier, and passing a syringe with cannula over the top of the IOL, wherein the syringe can be filled with a viscoelastic material. The viscoelastic material can be used to displace the air towards the proximal side of the IOL. The syringe can pass the top of the IOL from the distal end in some embodiments. In some other embodiments, the syringe can pass the top of the IOL from the proximal end. The cannula may be in close proximity to the optic 643 of the IOL 640. Care needs to be taken to avoid damage to the optic 643 of the IOL 640.

In some embodiments, the air over the anterior portion of the IOL 640 and near the proximal haptic 642 can be removed when the loading member or push member 630 is retracted, as shown in FIGS. 25A-C. The carrier lid 650 can comprise an opening 655 to insert the syringe 658 with the cannula as shown in FIG. 25A. The cannula of the syringe 658 can be inserted through the opening 655 while the push member 630 is still advanced at the last step of the loading and over the anterior portion of the IOL 640. The cannula can be advanced to a position over the anterior portion of the IOL 640. The syringe 658 can insert a viscoelastic material 682 to displace the air over the anterior portion of the IOL 640, or air at any other location within the cartridge. The viscoelastic material 682 can be the same or different than the viscoelastic material 680 inserted from the side port of the carrier 600. In some other embodiments, the base of the carrier 600 can comprise an opening to insert a syringe with a cannula to displace the air adjacent the IOL. In some alternative embodiments, the side of the carrier 600 can comprise an opening to insert a syringe with a cannula to displace the air over the anterior portion of the IOL or other areas adjacent the IOL.

The method of removing air from the IOL 640 during loading can comprise placing a cannula of a viscoelastic syringe over the anterior portion of the IOL 640 while the push member 630 is still advanced at the last step of the loading, and inserting a viscoelastic material over the anterior portion of the IOL 640 while the push member 630 is retracting.

FIG. 25B illustrates a section view when the push member is being retracted. The volume around the push member can be filled with the viscoelastic material 682 so that after the push member is retracted, the volume that is displaced is replaced with the viscoelastic material 682 instead of air. After the push member is completely retracted, the proximal channel can be left full of the viscoelastic material 682. This method has the advantages of reducing the need for a cannula to be in close proximity to the IOL optic 643. In some embodiments, the method can further comprise making a mark on the loading carrier 600 to where the viscoelastic material 682 needs to be filled to be effective in a predetermined volume.

FIGS. 25A-C illustrate a method of air venting of IOL during the delivery process. The cartridge 660 with the IOL 640 loaded inside can be connected to a delivery system, which can deliver the IOL 640 into an eye of a patient. For example, the delivery system of the IOL 640 can be the delivery system described in U.S. Pat. No. 8,968,396, titled: "Intraocular Lens Delivery Systems and Methods of Use", filed Mar. 15, 2013, which is herein incorporated by reference in its entirety. The delivery system can comprise a plunger assembly 690 as shown in FIG. 25A. The plunger assembly 690 can include a lumen extending from a proximal end to a distal end. This allows the viscoelastic fluid, or other material, to be delivered from the proximal end of the plunger 690 into the cartridge 660, pushing the loaded IOL 640 from within the cartridge 660 out the distal tip (shown with a bevel) and into the patient's eye. Plunger 690 has a proximal portion that is adapted to interact with a fluid delivery device, such as a syringe, so that fluid can be advanced from the fluid delivery device and into the inner lumen within plunger 690. Distal end of plunger 690 is disposed within the cartridge 660, and thus the fluid is delivered to a location that is radially and axially within the lumen, even if it does not exit the plunger 690.

When the IOL 640 is loaded into the cartridge 660 from the carrier, the cartridge 660 is removed from the carrier and the plunger assembly 690 can be mounted to the cartridge 660 proximal to the IOL 640. The IOL 640 in the cartridge 660 at this point is encapsulated in the viscoelastic material. At this point the plunger 690 is not full of a viscoelastic material but only air in the open fluid pathways. There is a void of viscoelastic proximal to the IOL 640.

Figure 26A:
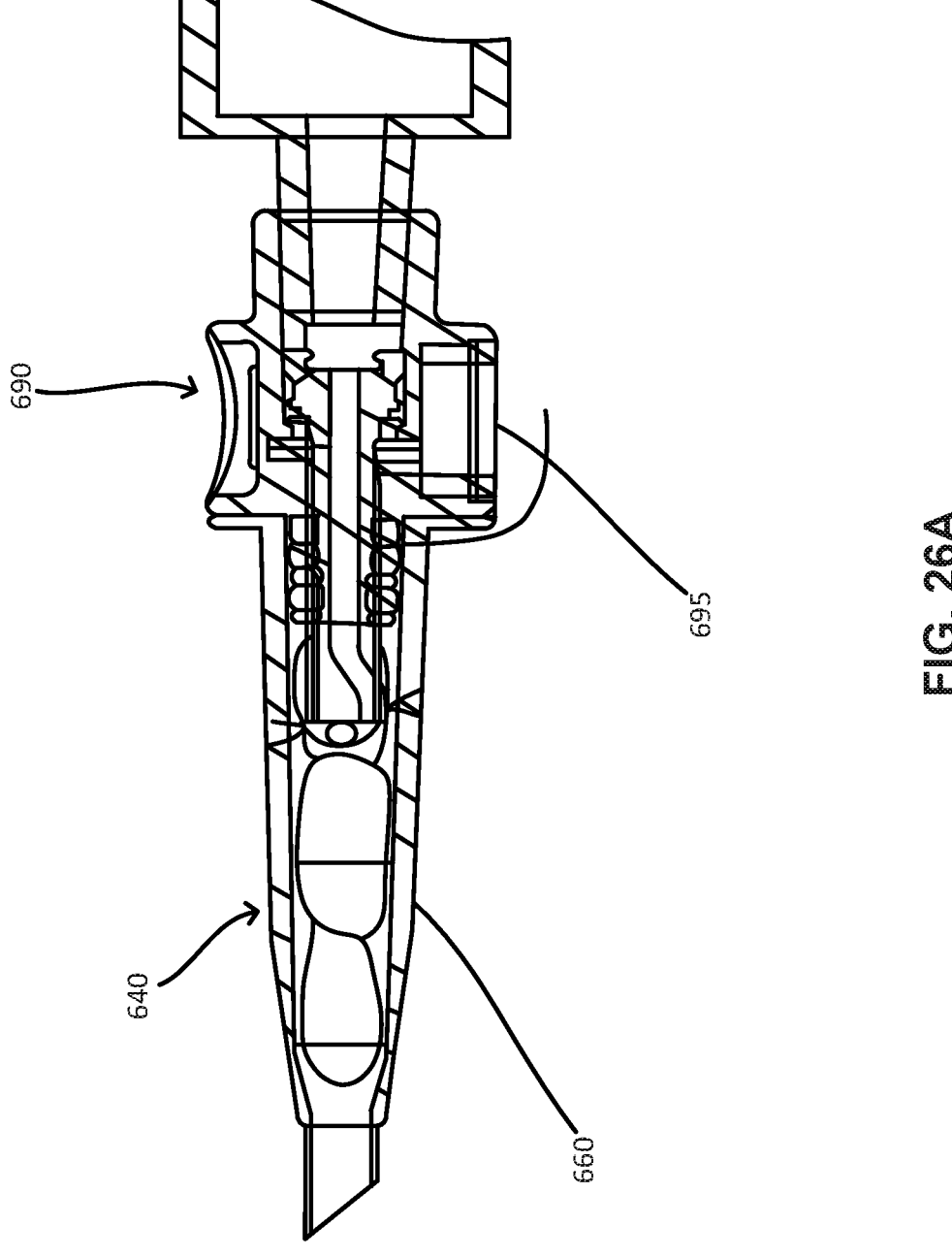
FIGS. 26A, 26B, and 26C show viscoelastic fluid traveling from a syringe through a support tube.
Figure 26B:
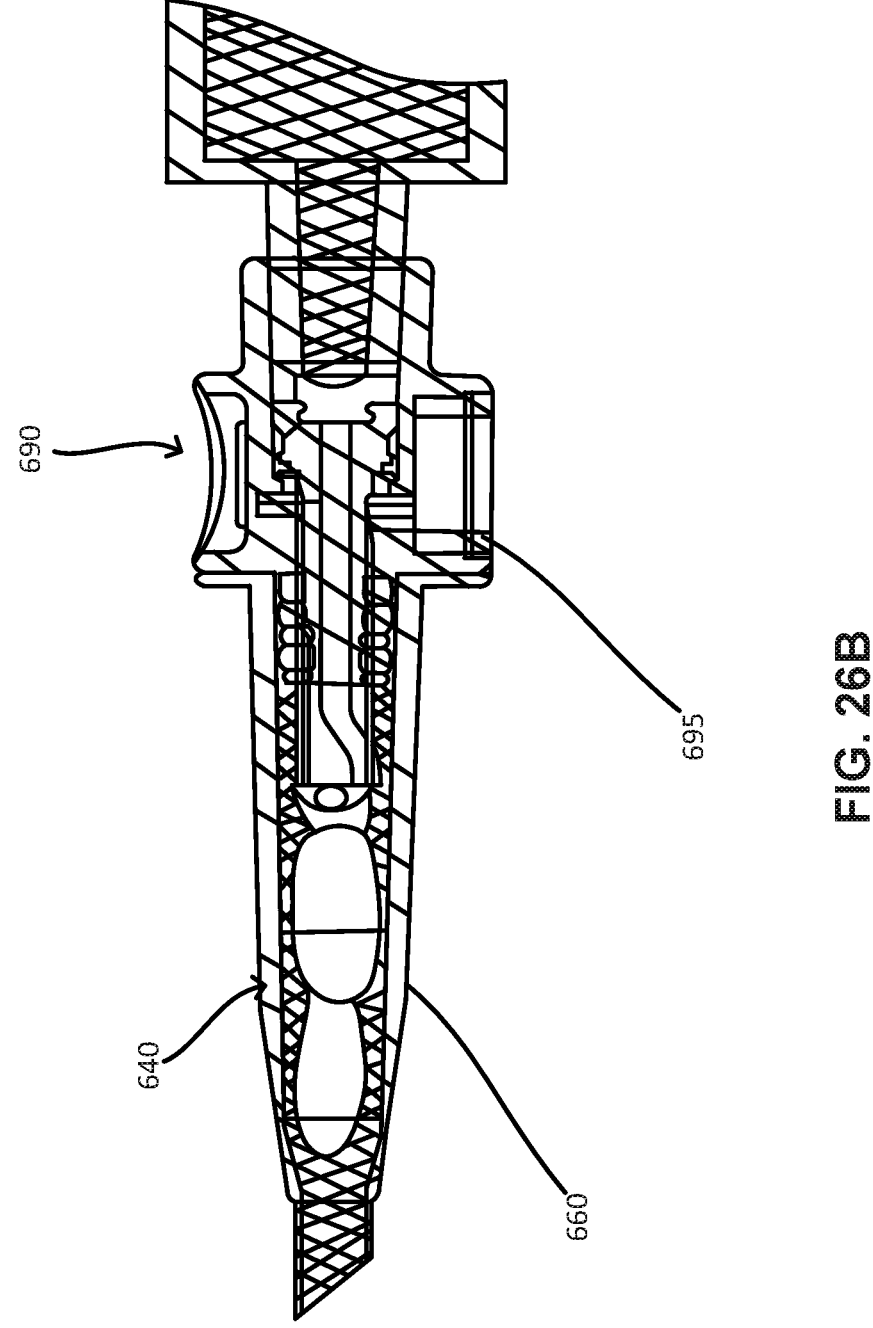

After the IOL 640 is loaded into the cartridge 660 as shown in FIG. 26A, a viscoelastic fluid, or other type of fluid, can delivered from a syringe and into lumen of plunger 690 (see FIG. 26B). The viscoelastic fluid can delivered from the distal port of plunger 690 and into contact with the IOL 640, forcing the IOL 640 distally within cartridge 660 and out the distal end of the cartridge 660. In general, the delivery of the IOL 640 from the cartridge 660 relies on development of pressure differential in the viscoelastic over the IOL 640 to move it down the reducing section of the cartridge 660 and into the eye.

The compressed residual air behind the IOL 640 during the highest pressure of the IOL 640 delivery can lead to uncontrolled delivery of the IOL 640 into the eye as the IOL body passes the most constricted portion of the cartridge 660. The compressed air proximal of the IOL 640 can be expanded and push the IOL forward without user input, which can possibly damage the IOL 640 or the capsule in the eye, or even cause the IOL 640 to be delivered outside of the capsule. The purging of air is important for a smooth, controlled delivery of the IOL 640.

When the cartridge tip is placed in the eye and the screw drive is beginning to be advanced, the viscoelastic fluid of the plunger 690 displaces air forward out of the plunger 690 by filling the luer fitting, support tube, through the semi porous expanded PTFE tubing and then being redirected back around the support tube and down through the exhaust vent 695. The forward direction is towards the tip of the carrier 660. The air is followed by the viscoelastic fluid to the vent 695 due to this being the lowest pressure path since the IOL 640 is fully or partially sealing against the cartridge 660 wall. The forward path to the tip is blocked by the IOL 640 and loading viscoelastic material. When the vent 695 seals with viscoelastic fluid, the system is able to develop pressure to move the IOL 640 forward to the tip of the cartridge 660 without a significant amount of air behind the IOL 640 as shown in FIG. 26C.

Figure 26C:
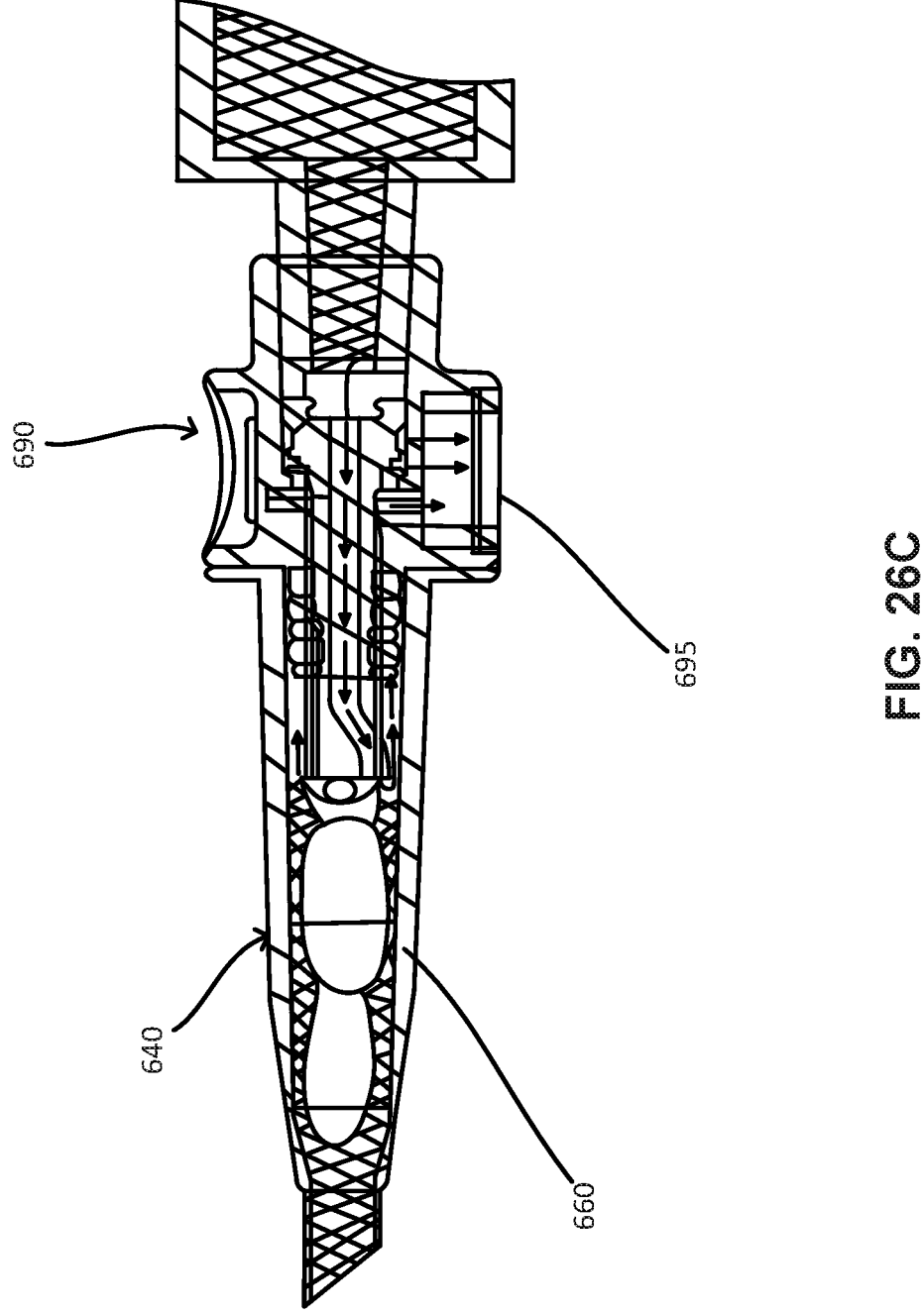

As shown in FIGS. 26A-C, the viscoelastic fluid travels from a syringe through support tube and exits in proximity of the trailing haptic of the IOL 640 within a plug element, for example, an EPTFE membrane. The fluid front travels both distally filling the plug element, and rearward evacuating the volume within vent 695. The vent 695 will not pass viscoelastic so is able to maintain pressure when fully evacuated. This effect purges the air from the back of the system to reduce spring effects of trapped air during the release of the IOL 640 during delivery.

In some embodiments the delivery system includes a vent and does not include a plug, or sealing element. In these embodiments fluid such as viscoelastic is delivered towards the IOL 640 as part of the delivery process. Air venting to increase control during delivery while decreasing the volume of air bubbles that are moved forward through the tip into the eye provides a significant advantage even in the absence of a plug element.

Figure 27:
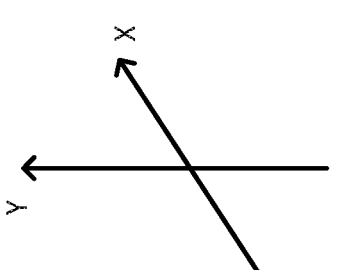
FIG. 27 is a top view of an exemplary cartridge, which can be used to deliver an intraocular lens into an eye.
Figure 27:
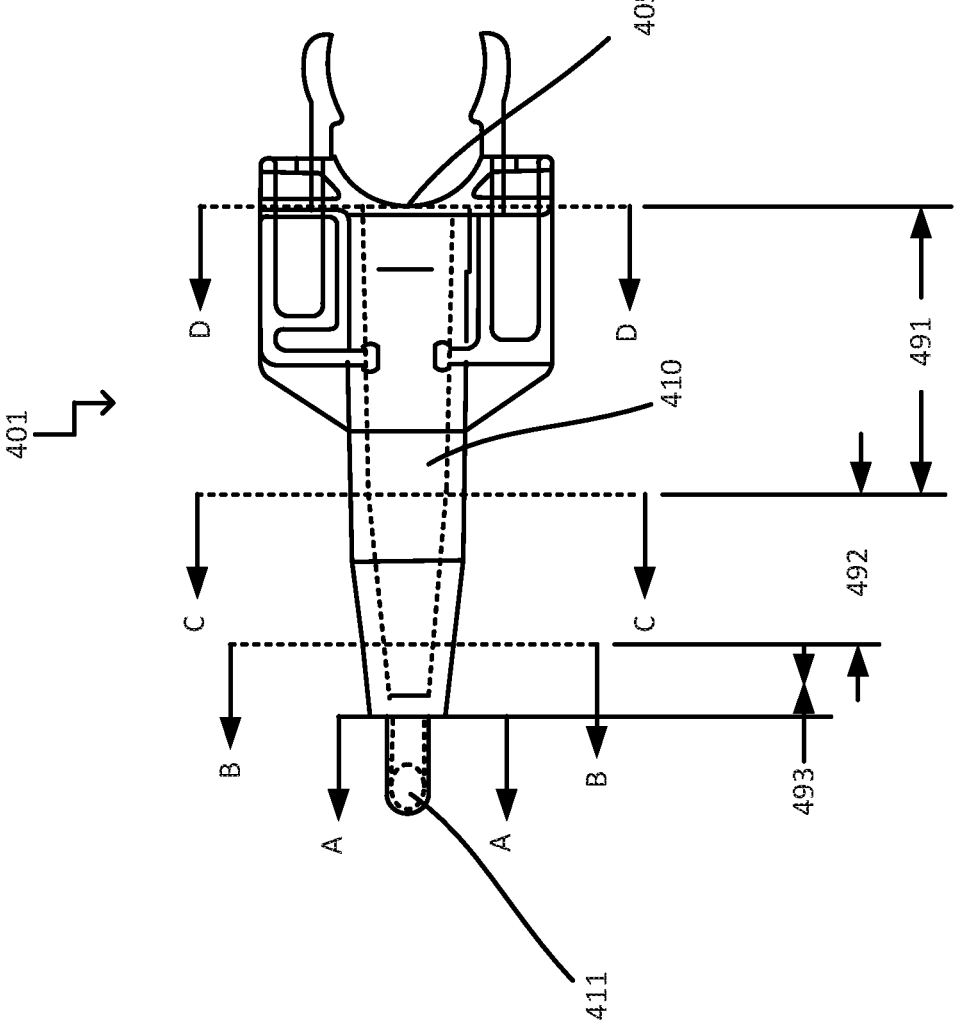

The following disclosure of FIGS. 27-28D is related to the full disclosure of WO2013/142323, which is fully incorporated by reference herein. Intraocular lenses are positioned within a patient's eye, such as in the anterior chamber or posterior chamber. After making a small incision in the eye, a physician typically positions a distal opening of a delivery device within or adjacent to the opening. The physician then delivers the intraocular lens out of the delivery device, through the opening, and into the target location within the eye. In some procedures, but not all, an intraocular lens is delivered into a native capsule after the native lens has been removed.

Some intraocular lenses, because of their size and/or their configuration, and possibly the desired incision size, need to be reconfigured and/or have at least a first portion reoriented with respect to a second portion to be delivered into an eye. When some intraocular lenses are advanced through a delivery device and/or delivered out of the delivery device, forces on the intraocular lens can damage the intraocular lens.

What are needed are delivery systems and methods of use that can deliver an intraocular lens without damaging the intraocular lens.

FIG. 27 is a top view of an exemplary cartridge 401, which can be used to deliver an intraocular lens into an eye. Cartridge 401 is an example of any of the cartridges described herein. The cartridge 401 can comprise a proximal opening 405 disposed to be engaged with a loading carrier to accept the intraocular lens (not shown), and a distal tip 411 adapted to deliver the intraocular lens into an eye. The cartridge 401 can comprise a lumen 410 extending from the proximal opening 405 to the distal tip 411. The lumen 410 can comprise a cross section having a first axis X and a second axis Y of an internal ellipse. The lumen 410 can further comprise a first portion 491 adapted to engage with the loading carrier and, without limitation, begin to fold the intraocular lens without stretching the intraocular lens out, a second portion 492 adapted to, without limitation, form a seal (or at least substantial seal) between an inner wall and the intraocular lens, and a third portion 493 adapted to, without limitation, compress the intraocular lens to extend the intraocular lens in length.

The intraocular lens can be disposed within lumen 410 and positioned to be deployed out of the distal tip 411 of the cartridge 401. The distal end of a plunger, such as any of the plungers herein, can be disposed within the proximal opening 405 in the cartridge 401 when assembled. The cartridge 401 can be adapted to accept the intraocular lens from the loading carrier into the cartridge 401, and have a tapered distal end to deform, compress, and optionally stretch out the intraocular lens in to deliver the intraocular lens into the eye.

FIGS. 28A-C illustrate exemplary internal cross sections DD, CC, BB and AA of the cartridge 401 in FIG. 27. Section DD represents the proximal opening 405. Section CC represents the intersection of the first portion 491 and the second portion 492. Section BB represents the intersection of the second portion 492 and the third portion 493. Section AA represents the distal end of the third portion 493, and shows the cross section of the distal-most region of cartridge 401. Referring to FIGS. 27 and FIGS. 28A-C, as the intraocular lens is pushed through the cartridge 401 (right to left as shown in FIG. 27), the cartridge 401 internal cross-section transitions from a lumen 410 large enough to hold the lens without compressing it (assuming the haptics are splayed out away from the lens body) at section DD all the way down to the final, compressing lumen 410 shown in section AA.

In some embodiments the transition from section DD to CC is that both a first radius 410a along the first axis X and a second radius 410b along the second axis Y on the cross section shrinks from the proximal opening 405 to section CC, which serves to interface with the lens carrier, accept the lens into the cartridge 401, and fold the lens body without stretching it out. In some embodiments, both the first radius 410a and the second radius 410b on the cross section decrease from the proximal opening 405 to the section CC. In some embodiments, the first radius 410a on the cross section at the proximal opening 405 is from about 2 mm to about 7 mm. For example, the first radius 410a on the cross section at the proximal opening 405 can be from about 4.6 mm to about 5.6 mm. Values outside the above range are also possible. In some embodiments a second radius 410b on the cross section at the proximal opening 405 is from about 1 mm to about 6 mm. For example, the second radius 410b on the cross section at the proximal opening 405 can be from about 3.5 mm to about 4.5 mm. Values outside the above range are also possible.

In some embodiments the first radius 410a is larger than the second radius 410b on the cross section from the proximal opening 405 to the intersection of the first portion and the second portion CC. In some embodiments the first radius 410a on the cross section at an intersection CC of the first portion 491 and the second portion 492 is from about 1.5 mm to about 6.5 mm. For example, the first radius 410a on the cross section at section CC can be from about 4.0 mm to about 5.0 mm. Values outside the above range are also possible. In some embodiments the second radius 410b on the cross section at the intersection CC is from about 0.5 mm to about 5.5 mm. For example, the second radius 410*b* on the cross section at section CC can be from about 2.6 mm to about 3.6 mm. Values outside the above range are also possible.

Between sections CC and BB the lens is forming a substantial seal against the inner wall of the lumen 410. In some embodiments the first radius 410*a* and the second radius 410*b* on the cross section decrease from the intersection CC of the first portion 491 and the second portion 492 to the intersection BB of the second portion 492 and the third portion 493.

In some other embodiments the first radius 410*a* decrease but the second radius 410*b* remains the same on the cross section from the intersection CC to the intersection BB. In some embodiments the first radius 410*a* is larger than the second radius 410*b* on the cross section at the intersection CC, and the first radius 410*a* is smaller than the second radius 410*b* on the cross section at the intersection BB. In some embodiments the first radius 410*a* on the cross section at the intersection BB of the second portion 492 and the third portion 493 is from about 0.5 mm to about 5 mm. For example, the first radius 410*a* on the cross section at intersection BB can be about 2.6 mm to about 3.6 mm. In some embodiments the second radius 410*b* on the cross section at the intersection BB is from about 0.5 mm to about 5.5 mm. For example, the second radius 410*b* on the cross section at intersection BB can be about 2.2 mm to about 3.2 mm. Values outside the above range are also possible.

Between sections BB and AA the lens is being stretched out by the rapid reduction of cross sectional area (to below the minimum cross sectional area of the lens itself). This causes the lens to extend in length. In some embodiments both the first radius 410*a* and the second radius 410*b* on the cross section decrease from the intersection BB of the second portion 492 and the third portion 493 to a distal end AA of the third portion 493. In some embodiments the first radius 410*a* is different than the second radius 410*b* on the cross section at the intersection BB, and the first radius 410*a* is the same as the second radius 410*b* on the cross section at the distal end AA. In some embodiments the cross section changes from an elliptical shape to a circular shape in the third portion.

In some embodiments the first radius 410*a* and the second radius 410*b* on the cross section decrease at a first average rate from the proximal opening 405 to the intersection CC, the first radius 410*a* and the second radius 410*b* on the cross section decrease at a second average rate from the intersection BB to the distal end AA, and the second average rate is larger than the first average rate. In some embodiments the first radius 410*a* is the same as the second radius 410*b* on the cross section at the distal end AA. In some embodiments a radius of a cross section at a distal end AA of the third portion is from about 0.1 mm to about 4 mm. For example, the radius 410*c* on the cross section at intersection AA can be about 1.5 mm to about 2.5 mm. Values outside the above range are also possible.

From section AA to the tip there is no change in cross-sectional area. In some embodiments, the apparatus can further comprise a fourth portion extending from the distal end AA of the third portion 493 to the distal tip 411. In some embodiments the cross section remains the same from the distal end AA of the third portion 493 to the distal tip 411.

One aspect of the disclosure is a method of delivering an intraocular lens into an eye. The method can comprise engaging a delivery device to a loading carrier to accept the intraocular lens. The method can comprise folding the intraocular lens without stretching the intraocular lens out. The method can comprise forming a seal between an inner wall of the delivery device and the intraocular lens. The method can comprise compressing the intraocular lens to extend the intraocular lens in length and delivering the intraocular lens into the eye.

In some embodiments the step of folding the intraocular lens comprises decreasing a first radius along a first axis and a second radius along a second axis of an internal ellipse of a cross section of the delivery device at a first average rate. In some embodiments compressing the intraocular lens comprises decreasing a first radius along a first axis and a second radius along a second axis of an internal ellipse of a cross section of the delivery device at a second average rate. In some embodiments the second average rate during the step of compressing the intraocular lens is larger than the first average rate during the step of folding.

Characteristics of the intraocular lenses described herein can similarly be applied to non-fluid driven accommodating intraocular lenses. For example, a non-accommodating intraocular lens can include a peripheral portion with a first stiffer region that provides a region of the peripheral portion with an insensitivity in a first direction. For example, in an intraocular lens with two lenses adapted to be moved apart from one another to change the power of the lens, the peripheral portion of the lens can be adapted such that a first type of capsular reshaping does not cause the distance between the lenses to change, and thus the power of the intraocular lens stays the same.

Additionally, the accommodating intraocular lenses herein can also be adapted to be positioned outside of a native capsular bag. For example, the accommodating intraocular lenses can be adapted to be positioned in front of, or anterior to, the capsular bag after the native lens has been removed or while the native lens is still in the capsular bag, wherein the peripheral portion of the lens is adapted to respond directly with ciliary muscle rather than rely on capsular reshaping.

We claim:

1. An intraocular lens, comprising:
an optic portion comprising a posterior element; and
a haptic comprising one or more ridges located posterior to the posterior element and protruding, in a posterior direction, from a rounded posterior outer surface of the haptic, wherein the rounded posterior outer surface is located posterior to the posterior element, and wherein at least one of the ridges is a square-shaped ridge, wherein the haptic comprises a proximal portion coupled to the optic portion and a distal free end not coupled to the optic portion, and wherein the one or more ridges extend along a length of the haptic from the proximal portion to the distal free end.

2. The intraocular lens of claim 1, wherein the optic portion comprises an optic fluid chamber, wherein the haptic comprises a haptic fluid chamber, wherein the haptic fluid chamber is surrounded by an anterior chamber wall, a posterior chamber wall, and lateral chamber walls, and wherein the rounded posterior outer surface of the haptic is an outer surface of the posterior chamber wall.

3. The intraocular lens of claim 1, wherein at least one of the ridges extend along an entire length of the haptic.

4. The intraocular lens of claim 1, wherein at least one of the ridges extend along at least 75% of the length of the haptic.

5. The intraocular lens of claim 1, wherein at least one of the ridges has a ridge height of between about 50 μm to about 500 μm.

6. The intraocular lens of claim 1, wherein the square-shaped ridge has a ridge width of between about 50 μm to about 500 μm.

\* \* \* \* \*